US006818215B2

(12) United States Patent
Smith et al.

(10) Patent No.: US 6,818,215 B2
(45) Date of Patent: Nov. 16, 2004

(54) ANTIBODIES TO SENESCENT CELL-DERIVED INHIBITERS OF DNA SYNTHESIS

(76) Inventors: James R. Smith, 10311 Cliffwood, Houston, TX (US) 77035; Asao Noda, Oguradai 2-10-52, Kita-ku, Kobe 651 (JP); Guy Adami, 826 S. Bishop St., Chicago, IL (US) 60607

(*) Notice: Subject to any disclaimer, the term of this patent is extended or adjusted under 35 U.S.C. 154(b) by 301 days.

(21) Appl. No.: 10/008,960

(22) Filed: Dec. 7, 2001

(65) Prior Publication Data

US 2003/0133971 A1 Jul. 17, 2003

Related U.S. Application Data

(63) Continuation of application No. 08/327,874, filed on Oct. 24, 1994, now Pat. No. 6,372,249, which is a continuation-in-part of application No. PCT/US94/09700, filed on Aug. 26, 1994, now abandoned, which is a continuation-in-part of application No. 08/274,535, filed on Jul. 13, 1994, now abandoned, and a division of application No. 08/268,439, filed on Jun. 30, 1994, now abandoned, which is a continuation-in-part of application No. 08/229,420, filed on Apr. 15, 1994, now abandoned, which is a continuation-in-part of application No. 08/203,535, filed on Feb. 25, 1994, now abandoned, and a division of application No. 08/160,814, filed on Jan. 3, 1994, now Pat. No. 5,424,400, which is a continuation-in-part of application No. 08/153,564, filed on Nov. 17, 1993, now abandoned, which is a continuation-in-part of application No. 08/113,372, filed on Aug. 30, 1993, now abandoned, which is a continuation-in-part of application No. 07/970,462, filed on Nov. 2, 1992, now Pat. No. 5,302,706, which is a continuation-in-part of application No. 07/808,523, filed on Dec. 16, 1991, now abandoned.

(51) Int. Cl.[7] .................. A61K 39/395; G01N 33/53; G01N 33/577; C12N 5/12
(52) U.S. Cl. .................. 424/139.1; 424/141.1; 424/172.1; 435/7.1; 435/331; 435/346
(58) Field of Search .................. 424/139.1, 141.1, 424/172.1; 435/7.1, 331, 346

(56) References Cited

U.S. PATENT DOCUMENTS

| | | | |
|---|---|---|---|
| 4,247,411 A | 1/1981 | Vanlerberghe et al. |
| 4,837,380 A | 6/1989 | Deftos et al. |
| 4,897,355 A | 1/1990 | Eppstein et al. |
| 5,077,211 A | 12/1991 | Yarosh |
| 5,164,488 A | 11/1992 | Vanlerberghe et al. |
| 5,190,762 A | 3/1993 | Yarosh |
| 5,204,112 A | 4/1993 | Hope et al. |
| 5,296,231 A | 3/1994 | Yarosh |
| 5,302,706 A | 4/1994 | Smith |
| 5,424,400 A | 6/1995 | Smith |
| 5,449,755 A | 9/1995 | Roberts et al. |

FOREIGN PATENT DOCUMENTS

| | | |
|---|---|---|
| EP | 0 293 249 | 5/1988 |
| WO | WO 91/01719 | 2/1991 |
| WO | WO 92/20796 | 11/1992 |
| WO | WO 93/06123 | 4/1993 |
| WO | WO 93/10242 | 5/1993 |
| WO | WO 93/19091 | 9/1993 |
| WO | WO 94/09135 | 4/1994 |

OTHER PUBLICATIONS

Biesinger et al. *Virology*, 176, pp. 505–514, 1990.*
Gennaro. A.R. et al., "Sustained–Release Drug Delivery Systems, *Philadephia College of Pharmacy and Science*", pp. 1691–1693 (1990).
Drescher–Lincoln, C.K. et al., "Inhibition of DNA Synthesis in Proliferating Human Diploid Fibroblasts by Fusion with Senescent Cells," *Exp. Cell Res. 144:* 455–462 (1983).
Drescher–Lincoln, C.K. et al., "Inhibition of DNA Synthesis in Senescent–Proliferating Human Cybrids is Mediated by Endogenous Proteins," *Exp. Cell Res. 153:*208–217 (1984).
Lumpkin, C.K. et al., "Existence of High Abundance Antiproliferative mRNA's in Senescent Human Diploid Fibroblasts," *Science* 232:393–395 (1986).
West, M.D. et al., "Replicative Senescence of Human Skin Fibroblasts Correlates with a Loss of Regulation and Overexpression of Collagenase Activity," *Exp. Cell Res. 184:*138–147 (1989).
Giordano, T. et al., "Identification of a Highly Abundant cDNA Isolated from Senescent WI–38 Cells," *Exp. Cell Res. 185:*399–406 (1989).
Sierra, F. et al., "T–Kininogen Gene Expression Is Induced during Aging," *Molec. Cell. Biol.* 9:5610–5616 (1989).
Maier, J.A.M. et al., "Extension of the Life–Span of Human Endothelial Cells by an Interleukin–1a Antisense Oligomer," *Science* 249:1570–1574 (1981).
Smith, J.R., "A Hypothesis for in vitro Cellular Senescence Based on the Population Dynamics of Human Diploid Fibroblasts and Somatic Cell Hybrids,", In: *Monographs in Developmental Biology*; Sauer, H. W. (Ed.), S. Karger, New York, N.Y. 17:193–207 (1984).
Smith, J.R. et al., "Further Studies on the Genetic and Biochemical Basis of Cellular Senescence," *Exper. Gerontol.* 24:377–381 (1989).
Spiering, A.L. et al., "A Potent DNA Synthesis Inhibitor Expressed by the Immortal Cell Line SUSM–1," *Exper. Cell Res.* 179:159–167 (1988).
Pereira–Smith, O.M. et al., "Senescent and Quiescent Cell Inhibitors of DNA Synthesis *Membrane–Associated Proteins.*" Exper. Cell Res. 160:297–306 (1985).
Kleinsek, D.A., "Selection of mRNAs Expressed During Cellular Senescene In Vitro." *Age* 12:55–60 (1989).

(List continued on next page.)

*Primary Examiner*—Gary Kunz
*Assistant Examiner*—Stephen Gucker
(74) *Attorney, Agent, or Firm*—Clifford Chance LLP US; Margaret Kelley

(57) ABSTRACT

Polyclonal and monoclonal antibodies that specifically bind senescent cell derived inhibitor protein (SDI-1), cell lines that produce such monoclonal antibodies, and the use of such antibodies are disclosed.

18 Claims, 9 Drawing Sheets

OTHER PUBLICATIONS

Pereira–Smith. O.M. et al., "Negative Growth Control in Cellular Senescence," *J Cell. Biochem* (Suppl9 (12 part A) 193, 1988).

Kleinsek, D.A. et al., "Isolation of cDNA Sequences Specific to Senescent Human Diploid Fibroblast Cells In Vitro", *Age 10*:125 (1987).

Spiering, A.L. et al., "Correlation between Complementation Group for Immortality and DNA Synthesis inhibitors," *Exper. Cell Res. 195*:541–545 (1991).

Murano, S. et al., "Diverse Gene Sequences Are Overexpressed in Werner Syndrome Fibroblasts Undergoing Premature Replicative Senescence," *Molec. Cell. Biol. 11*:3905–3914 (Aug. 1991).

Pereira–Smith, O.M. et al., "Genetic Analysis of Infinite Division in Human Cells: Identification of Four Complementation Groups," *Proc. Natl. Acad. Sci. (U.S.A.) 85*:6042–6046 (1988).

Ning, Y. et al., "Genetic Analysis of Indefinite Division in Human Cells: Evidence for a Cell Senescence–Related Gene(s) on Human Chomosome 4," *Proc. Natl. Acad. Sci. (U.S.A.) 88*:5635–5639 (1991).

Smith, J.R., "Expression of Antiproliferative Genes in Senescent Cells," *J.A.G.S. 35*:894 (1987).

Smith, J.R. et al., "Negative Growth Control in Cellular Senescence," *J. Cell Biochem Suppl. (13 part C)* 147 (1989).

Takebe, Y. et al., "SRa Promoter: An Efficient and Versatile Mammalian cDNA Expression System Composed of the Simian Virus 40 Early Promoter and the R–U5 Segment of Human T–Cell Leukemia Virus Type 1 Long Terminal Repeat," *Mol. Cell Biol. 8*:466–472 (1988).

Xiong, H. et al., "D Type Cyclins Associate with Multiple Protein Kinases and the DNA Replication and Repair Factor PCNA." *Cell 71*:505–514 (1992).

Sherr, C.J.. "Mammalian G1 Cyclins," *Cell 73*:1059–1065 (1993).

Lew, D.J. et al., "Isolation of Three Novel Human Cyclins by Rescue of G1 Cyclin (Cln) Function in Yeast," *Cell 66*:1197–1206 (1991).

Hunter, T. et al., "Cyclins and Cancer." *Cell 66*:1071–1074 (1991).

Norbury, C. et al., "Animal Cell Cycles and Their Controls," *Ann. Rev. Biochem. 61*:441–470 (1992).

Koff, A. et al., "Human Cyclin E, a New Cyclin That Interacts With Two Members of the CDC2 Gene Family," *Cell 66*:1217–1228 (1991).

El–Deiry, W.S. et al., "WAF1, A Potent Mediator of p53 Tumor Suppression," *Cell 75*:817–825 (1993).

Harper. J.W. et al., "The p21 Cdk–Interacting Protein Cip1 Is A Potent Inhibitor of G1 Cyclin–Dependent Kinases," *Cell 75*:805–816 (1993).

Jiang, H., et al., "Use of a Sensitive and Efficient Substraction Hybridization Protocol for the Identification of Genes Differentially Regulated During the Induction of Differentiation in Human Melanoma Cells," *Molec. Cell Differentiation 1(3)*:285–299 (1993).

Tenenbaum, L., et al., "The Cell Cycle and Cancer Chemotherapy," In: "Cancer Chemotherapy and Biotherapy A Reference Guide," W.B. Saunders Company, Philadelphia, pp. 3–13 (1994).

Xiong, Y., et al., "p21 is a Universal Inhibitor of Cyclin Kinases," *Nature 366*:701–704 (1993).

Dulic, V., et al., "p53–Dependent Inhibition of Cyclin–Dependent Kinase Activities in Human Fibroblasts During Radiation–Induced G1 Arrest," *Cell 76*:1013–1023 (1994).

Pines, J.. "p21 Inhibits Cyclin Shock," *Nature 369*:520–578 (1994).

Noda, A., et al., "Cloning of Senescent Cell–Derived Inhibitors of DNA Synthesis Using an Expression Screen," *Exper. Cell. Res. 211*:90–98 (1994).

Xiong, Y., et al., "Subunit Rearrangement of the Cyclin Dependent Kinases is Associated with Cellular Transformation." *Genes Devel. 7*:1572–1583 (1993).

Egbaria, K., et al., "Topical Delivery of Liposomally Encapsulated Interferon Evaluated by In Vitro Diffusion Studies," *Antimicrob. Agents Chemother*. 34:107–110 (1990).

Cevc, G. et al., "Lipid Vesicles Penetrate into Intact Skin Owing to the Transdermal Osmotic Gradients and Hydration Force, " *Biochem Biophys. Acta 1104*:226–232 (1992).

Blume, G., et al., "Molecular Mechanism of the Lipid Vescicle Longevity in vivo," *Biochim Biophys. Acta 1146*:157–168 (1993).

Blume, G., et al., "Specific Targeting with Poly (theylene glycol)–Modified Liposomes: Coupling of Homing Devices to the Ends of the Polymeric Chains Combines Effective Target Binding with Long Circulation Times," *Biochim Biophys. Acta 1149*:180–184 (1993).

* cited by examiner

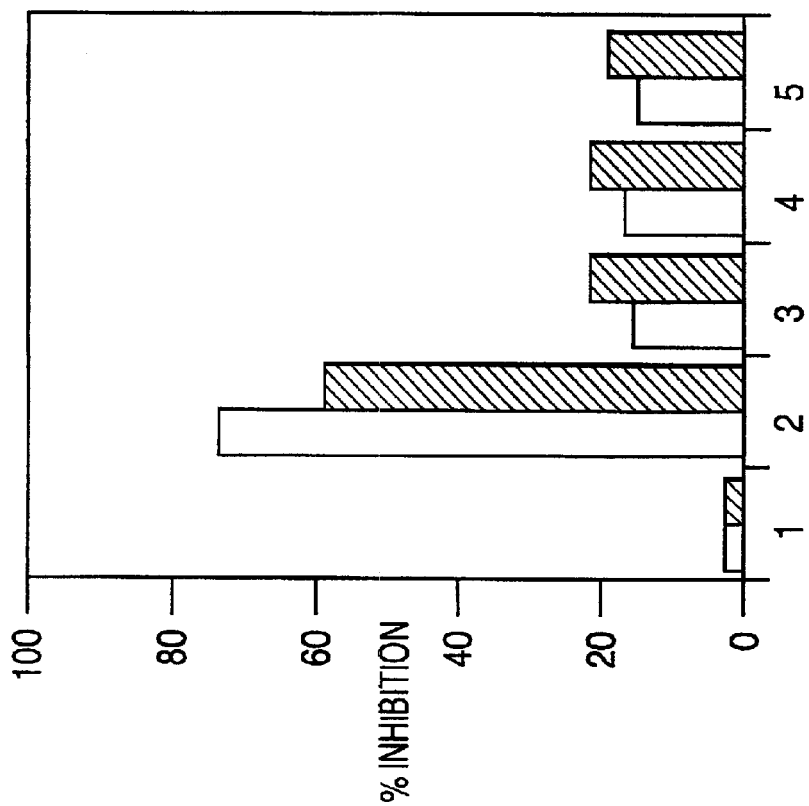
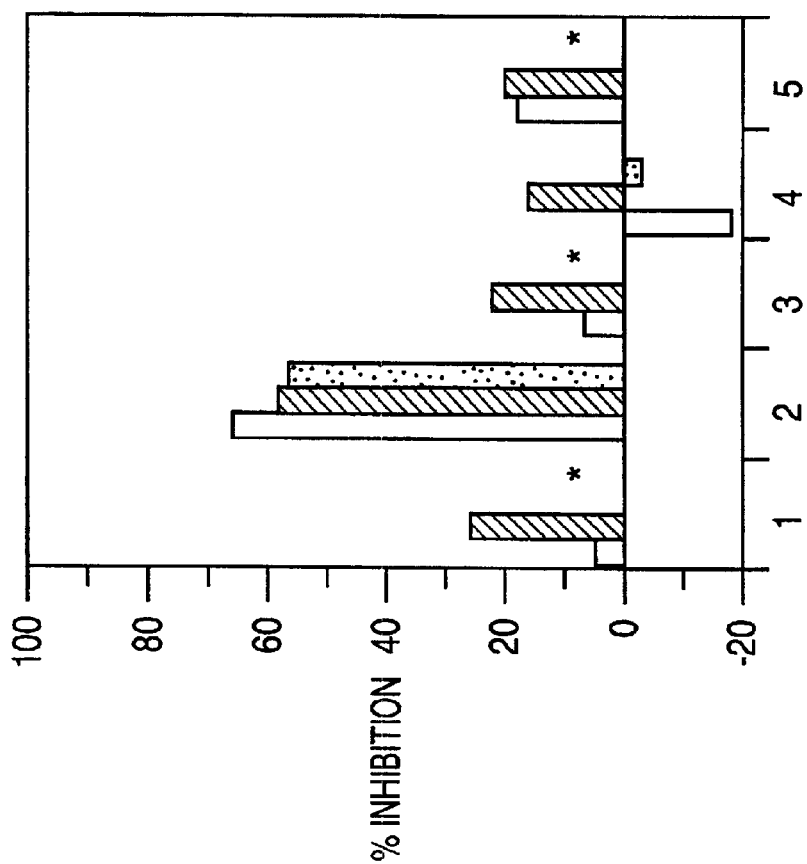
FIG. 2A
FIG. 2B

```
  1:  cct gcc gaa gtc agt tcc ttg tgg agc cgg agc tgg gcg cgg att

46:  cgc cga ggc acc gag gca ctc aga gga ggc gcc atg tca gaa ccg
                                                  M   S   E   P 91:  gct ggg gat gtc cgt cag aac cca tgc ggc agc aag gcc tgc cgc
  1:   A   G   D   V   R   Q   N   P   C   G   S   K   A   S   R 136:  cgc ctc ttc ggc cca gtg gac acc gag cag ctg agc cgc gac tgt
  1:   R   L   F   G   P   V   D   S   E   Q   L   S   R   D   C 181:  gat gcg cta atg gcg ggc tgc atc cag gag gcc cgt gag cga tgg
  1:   D   A   L   M   A   G   C   I   Q   E   A   R   E   R   W 226:  aac ttc gac ttt gtc acc gag aca cca ctg gag ggt gac ttc gcc
  1:   N   F   D   F   V   T   E   T   P   L   E   G   D   F   A 271:  tgg gag cgt gtg cgg ggc ctt ggc ctg ccc aag ctc tac ctt ccc
  1:   W   E   R   V   R   G   L   G   L   P   K   L   Y   L   P 316:  acg ggg ccc cgg cga ggc cgg gat gag ttg gga gga ggc agg cgg
  1:   T   G   P   R   R   G   R   D   E   L   G   G   G   R   R 361:  cct ggc acc tca cct gct ctg ctg cag ggg aca gca gag gaa gac
  1:   P   G   T   S   P   A   L   L   Q   G   T   A   E   E   D 406:  cat gtg gac ctg tca ctg tct tgt acc ctt gtg cct cgc tca ggg
  1:   H   V   D   L   S   L   S   C   T   L   V   P   R   S   G
```

FIG. 5A

```
451:  gag cag gct gaa ggg tcc cca ggt gga cct gga gac tct cag ggt
  1:   E   Q   A   E   G   S   P   G   G   P   G   D   S   Q   G 496:  cga aaa cgg cgg cag acc agc atg aca gat ttc tac cac tcc aaa
  1:   R   K   R   R   Q   T   S   M   T   D   F   Y   H   S   K 541:  cgc cgg ctg atc ttc tcc aag agg aag ccc taa tcc gcc cac agg
  1:   R   R   L   I   F   S   K   R   K   P 586:  aag cct gca gtc ctg gaa gcg cga ggg cct caa agg ccc gct cta 631:  cat ctt ctg cct tag tct cag ttt gtg tgt ctt aat tat tat ttg 676:  tgt ttt aat tta aac acc tcc tca tgt aca tac cct ggc cgc ccc 721:  ctg ccc ccc agc ctc tgg cat tag aat tat tta aac aaa aac tag 766:  gcg gtt gaa tga gag gtt cct aag agt gct ggg cat ttt tat ttt 811:  atg aaa tac tat tta aag cct cct cat ccc gtg ttc tcc ttt tcc 856:  tct ctc ccg gag gtt ggg tgg gcc ggc ttc atg cca gct act tcc 901:  tcc tcc cca ctt gtc cgc tgg gtg gta ccc tct gga ggg gtg tgg 946:  ctc ctt ccc atc gct gtc aca ggc ggt tat gaa att cac ccc ctt 991:  tcc tgg aca ctc aga cct gaa ttc ttt ttc att tga gaa gta aac
```

FIG. 5B

```
1036:  aga tgg cac ttt gaa ggg gcc tca ccg agt ggg ggc atc atc aaa

1081:  aac ttt gga gtc ccc tca cct cct cta agg ttg ggc agg gtg acc

1126:  ctg aag tga gca cag cct agg gct gag ctg ggg acc tgg tac cct

1171:  cct ggc tct tga tac ccc cct ctg tct tgt gaa ggc agg ggg aag

1216:  gtg ggg tcc tgg agc aga cca ccc cgc ctg ccc tca tgg ccc ctc

1261:  tga cct gca ctg ggg agc ccg tct cag tgt tga gcc ttt tcc ctc

1306:  ttt ggc tcc cct gta cct ttt gag gag ccc cag cta ccc ttc ttc

1351:  tcc agc tgg gct ctg caa ttc ccc tct gct gct gtc cct ccc cct

1396:  tgt cct ttc cct tca gta ccc tct cag ctc cag gtg gct ctg agg

1441:  tgc ctg tcc cac ccc cac ccc cag ctc aat gga ctg aag ggg gaa

1486:  ggg aca cac aag aag aag ggc acc cta gtt cta cct cag gca gct

1531:  caa gca gcg acc gcc ccc tcc tct agc tgt ggg ggt gag ggt ccc

1576:  atg tgg tgg cac agg ccc cct tga gtg ggg tta tct ctg tgt tag

1621:  ggg tat atg atg ggg gag tag atc ttt cta gga ggg aga cac tgg

1666:  ccc ctc aaa tcg tcc agc gac ctt cct cat cca ccc cat ccc tcc
```

FIG. 5C

1711: cca gtt cat tgc act ttg att agc agc gga aca agg agt cag aca

1756: ttt taa gat ggt ggc agt aga ggc tat gga cag ggc atg cca cgt

1801: ggg ctc ata tgg ggc tgg gag tag ttg tct ttc ctg gca cta acg

1846: ttg agc ccc tgg agg cac tga agt gct tag tgt act tgg agt att

1891: ggg gtc tga ccc caa aca cct tcc agc tcc tgt aac ata ctg gcc

1936: tgg act gtt ttc tct cgg ctc ccc atg tgt cct ggt tcc cgt ttc

1981: tcc acc tag act gta aac ctc tcg agg gca ggg acc aca ccc tgt

2026: act gtt ctg tgt ctt tca cag ctc ctc cca caa tgc tga tat aca

2071: gca ggt gct caa taa acg att ctt agt gaa aaa aaa

FIG. 5D

ANTIBODIES TO SENESCENT CELL-DERIVED INHIBITERS OF DNA SYNTHESIS

CROSS-REFERENCE TO RELATED APPLICATIONS

This application is a continuation application of U.S. application Ser. No. 08/327,874 filed Oct. 24, 1994 and now U.S. Pat. No. 6,372,249, which is a continuation-in-part of PCT/US94/09700 filed Aug. 26, 1994 and now abandoned, which is a continuation-in-part of U.S. application Ser. No. 08/274,535 filed Jul. 13, 1994 and now abandoned, which is a continuation-in-part of U.S. application Ser. No. 08/229,420 filed Apr. 15, 1994 and now abandoned, which is a continuation-in-part of U.S. application Ser. No. 08/203,535 filed Feb. 25, 1994 and now abandoned, which is a continuation-in-part of U.S. application Ser. No. 08/153,564 filed Nov. 17, 1993 and now abandoned, which is a continuation-in-part of U.S. application Ser. No. 08/113,372 filed Aug. 30, 1993 and now abandoned, which is a continuation-in-part of U.S. application Ser. No. 07/970,462 filed Nov. 2, 1992 and now U.S. Pat. No. 5,302,706, and divisional U.S. application Ser. No. 08/160,814 filed Jan. 3, 1994 and now U.S. Pat. No. 5,424,400 and U.S. application Ser. No. 08/268,439 filed Jun. 30, 1994 and now abandoned, all of which are continuations-in-part of U.S. application Ser. No. 07/808,523 filed Dec. 16, 1991 and now abandoned.

This invention was supported with Government funds. The Government has certain rights in this invention.

FIELD OF THE INVENTION

The present invention is in the field of recombinant DNA technology. This invention is directed to a gene sequence and a protein that effects the ability of cells to become senescent.

BACKGROUND OF THE INVENTION

Normal human diploid cells have a finite potential for proliferative growth (Hayflick, L. et al., *Exp. Cell Res.* 25:585 (1961); Hayflick, L., *Exp. Cell Res.* 37: 614 (1965)). Indeed, under controlled conditions in vitro cultured human cells can maximally proliferate only to about 80 cumulative population doublings. The proliferative potential of such cells has been found to be a function of the number of cumulative population doublings which the cell has undergone (Hayflick, L. et al., *Exp. Cell Res.* 25: 585 (1961); Hayflick, L. et al., *Exp. Cell Res.* 37: 614 (1985)). This potential is also inversely proportional to the in vivo age of the cell donor (Martin, G. M. et al., *Lab. Invest.* 23:86 (1979); Goldstein, S. et al., *Proc. Natl. Acad. Sci. (U.S.A.)* 64:155 (1969); Schneider, E. L., *Proc. Nati. Acad. Sci. (U.S.A.)* 73:3584 (1976); LeGuilty, Y. et al., *Gereontologia* 19:303 (1973)).

Cells that have exhausted their potential for proliferative growth are said to have undergone "senescence." Cellular senescence in vitro is exhibited by morphological changes and is accompanied by the failure of a cell to respond to exogenous growth factors. Cellular senescence, thus, represents a loss of the proliferative potential of the cell. Although a variety of theories have been proposed to explain the phenomenon of cellular senescence in vitro, experimental evidence suggests that the age-dependent loss of proliferative potential may be the function of a genetic program (Orgel, L. E., *Proc. Natl. Acad. Sci.* (U.S.A.) 49:517 (1963); De Mars, R. et al., *Human Genet.* 16:87 (1972); M. Buchwald, *Mutat. Res.* 44:401 (1977); Martin, G. M. et al., *Amer. J. Pathol.* 74:137 (1974); Smith, J. R. et al., *Mech. Age. Dev.* 13:387 (1980): Kirkwood, T. B. L. et al., *Theor. Biol.* 53:481 (1975).

Cell fusion studies with human fibroblasts in vitro have demonstrated that the quiescent phenotype of cellular senescence is dominant over the proliferative phenotype (Pereira-Smith, O. M et al., *Somat. Cell Genet.* 6:731 (1982); Norwood, T. H. et al., *Proc. Nati. Acad. Sci. (U.S.A.)* 71:223 (1974); Stein, G. H. et al., *Exp. Cell Res.* 130:155 (1979)).

Insight into the phenomenon of senescence has been gained from studies in which senescent and young (i.e. non-senescent) cells have been fused to form heterodikaryons. In order to induce senescence in the "young" nucleus of the heterodikaryon (as determined by an inhibition in the synthesis of DNA), protein synthesis must occur in the senescent cell prior to fusion (Burmer, G. C. et al., *J. Cell. Biol.* 94:187 (1982); Drescher-Lincoln, C. K. et al., *Exp. Cell Res.* 144:455 (1983); Burner, G. C. et al., *Exp. Cell Res.* 145:708 (1983); Drescher-Lincoln, C. K. et al., *Exp. Cell Res.* 153:208 (1984).

Likewise, microinjection of senescent fibroblast mRNA into young fibroblasts has been found to inhibit the ability of the young cells to synthesize DNA (Lumpkin, C. K. et al., *Science* 232:393 (1986)). Researchers have identified unique mRNAs that are amplified in senescent cells in vitro (West, M. D. et al., *Exp. Cell Res.* 184:138 (1989); Giordano, T. et al., *Exp. Cell Res.* 185:399 (1989)).

The human diploid endothelial cell presents an alternative cell type for the study of cellular senescence because such cells mimic cellular senescence in vitro (Maciag, T. et al., *J. Cell. Biol.* 91:420 (1981); Gordon, P. B. et al., *In Vitro* 19:661 (1983); Johnson, A. et al., *Mech Age. Dev.* 18:1 (1982); Thornton, S. C. et al., *Science* 222:623 (1983); Van Hinsbergh, V. W. M. et al., *Eur. J. Cell Biol.* 42:101 (1986); Nichols, W. W. et al., *J. Cell. Physiol.* 132:453 (1987)).

In addition, the human endothelial cell is capable of expressing a variety of functional and reversible phenotypes. The endothelial cell exhibits several quiescent and non-terminal differentiation phenotypes (Folkman, J. et al., *Nature* 288:551 (1980); Maciag, T. et al., *J. Cell Biol.* 94:511 (1982); Madri, J. A. et al., *J. Cell Biol.* 97:153 (1983); Montesano, R., *J. Cell Biol.* 99:1706 (1984); Montesano, R. et al., *J. Cell Physiol.* 34:460 (1988)).

It has been suggested that the pathway of human cell differentiation in vitro involves the induction of cellular quiescence mediated by cytokines that inhibit growth factor-induced endothelial cell proliferation in vitro (Jay, M. et al., *Science* 228:882 (1985); Madri, J. A. et al., *In Vitro* 23:387 (1987); Kubota, Y. et al., *J. Cell Biol.* 107:1589 (1988); Ingber, D. E. et al., *J. Cell Biol.* 107:317 (1989)).

Inhibitors of endothelial cell proliferation also function as regulators of immediate-early transcriptional events induced during the endothelial cell differentiation in vitro, which involves formation of the capillary-like, tubular endothelial cell phenotype (Maciag, T., In: *Imp. Adv. Oncol.* (De Vita, V. T. et al., eds., J. B. Lippincott. Philadelphia, 42 (1990); Goldgaber, D. et al., *Proc. Natl. Acad. Sci. (U.S.A.)* 86:7606 (1990); Hla, T. et al., *Biochem. Biophys. Res. Commun.* 167:637 (1990)). The inhibitors of cell proliferation include:

1. Interleukin-1a (IL-1a) (Montesano, R. et al., *J. Cell Biol.* 99:1706 (1984); Montesano, R. et al., *J. Cell Physiol.* 122:424 (1985); Maciag, T. et al. (*Science* 249:1570–1574 (1990));
2. Tumor necrosis factor (Frater-Schroder, M. et al., *Proc. Natl. Acad. Sci.* (U.S.A.) 84:5277 (1987); Sato, N. et al., *J. Natl. Cancer Inst.* 76:1113 (1986); Pber, J. P.,

*Amer. J. Pathol.* 133:426 (1988); Shimada, Y. et al., *J. Cell Physiol.* 142:31 (1990));

3. Transforming growth factor-β (Baird, A. et al., *Biochem. Biophys. Res. Commun.* 138:476 (1986); Mullew, G. et al., *Proc. Natl. Acad. Sci. (U.S.A.)* 84:5600 (1987); Mairi, J. A. et al., *J. Cell Biol.* 106:1375 (1988));
4. Gamma-interferon (Friesel, R. et al., *J. Cell Biol.* 104:689 (1987); Tsuruoka, N. et al., *Biochem. Biophys. Res. Commun.* 155:429 (1988)) and
5. The tumor promoter, phorbol myristic acid (PMA) (Montesano, R. et al., *Cell* 42:469 (1985); Doctrow, S. R. et al., *J. Cell Biol.* 104:679 (1987); Montesano, R. et al., *J. Cell. Physiol.* 130:284 (1987); Hoshi, H. et al., *FASAB J.* 2:2797 (1988)).

The prospect of reversing senescence and restoring the proliferative potential of cells has implications in many fields of endeavor. Many of the diseases of old age are associated with the loss of this potential. Restoration of this ability would have far-reaching implications for the treatment of this disease, of other age-related disorders, and, of aging per se.

In addition, the restoration of proliferative potential of cultured cells has uses in medicine and in the pharmaceutical industry. The ability to immortalize nontransformed cells can be used to generate an endless supply of certain tissues and also of cellular products.

The significance of cellular senescence has accordingly been appreciated for several years (Smith, J. R., Cellular Ageing, In: *Monographs in Developmental Biology*; Sauer, H. W. (Ed.), S. Karger, New York, N.Y. 17:193–208 (1984); Smith, J. R. et al. *Exper. Gerontol.* 24:377–381 (1989), herein incorporated by reference). Researchers have attempted to clone genes relevant to cellular senescence. A correlation between the existence of an inhibitor of DNA synthesis and the phenomenon of cellular senescence has been recognized (Spiering, A. I. et al., *Exper. Cell Res.* 179:159–167 (1988); Pereira-Smith, O. M. et al., *Exper. Cell Res.* 160:297–306 (1985); Drescher-Lincoln, C. K. et al., *Exper. Cell Res.* 153:208–217 (1984); Drescher-Lincoln, C. K. et al, *Exper. Cell Res.* 144:455–462 (1983)). Moreover, the relative abundance of certain senescence-associated RNA molecules has been identified (Lumpkin, C. K. et al, *Science* 232:393–395 (1986)).

Several laboratories have used the "subtraction-differential" screening method to identify cDNA molecules derived from RNA species that are preferentially present in senescent cells (Kleinsek, D. A., *Age* 12:55–60 (1989); Giordano, T. et at., *Exper. Cell. Res.* 185:399–406 (1989); Sierra, F. et al., *Molec. Cell. Biol.* 9:5610–5616 (1989); Pereira-Smith, O. M. et al., J Cell. Biochem. (Suppl 0 (12 part A)). 193 (1988); Kleinsek, D. A., Smith, J. R., *Age* 10:125 (1987)).

In one method, termed "subtraction-differential" screening, a pool of cDNA molecules is created from senescent cells, and then hybridized to cDNA or RNA of growing cells in order to "subtract out" those cDNA molecules that are complementary to nucleic acid molecules, present in growing cells. Although useful, for certain purposes, the "subtraction-differential" method suffers from the fact that it is not possible to determine whether a senescence-associated cDNA molecule is associated with the cause of senescence, or is produced as a result of senescence. Indeed, many of the sequences identified in this manner have been found to encode proteins of the extracellular matrix. Changes in the expression of such proteins would be unlikely to cause senescence.

SUMMARY OF THE INVENTION

This application is a continuation-in-part of PCT US94/09700 (filed Aug. 26, 1994), herein incorporated by reference in its entirety. The present invention concerns, in part, the observation that normal human cells exhibit a limited replicative potential in vitro and become senescent after a certain number of divisions. As the cells become senescent, they show several morphological and biochemical changes, such as enlargement of cell size, changes of extracellular matrix components, unresponsiveness: to mitogen stimulation and failure to express growth regulated genes.

The present invention identifies an inhibitor of DNA synthesis that is produced in senescent cells. This inhibitor plays a crucial role in the expression of the senescent phenotype. The gene coding for the inhibitor was identified by incorporating a senescent cell cDNA library into a mammalian expression vector. The cDNA library was then transfected into young, cycling cells to identify those library members that suppressed the initiation of DNA synthesis.

Efficient DEAE dextran-mediated transfection enabled the isolation of putative senescent cell derived inhibitor (SDI) sequences in three distinct cDNA clones. The expression of one (SDI-1) increased 20 fold at cellular senescence, whereas that of the others (SDI-2 and SDI-3) remained constant.

In summary, the present invention achieves the cloning of an inhibitor of DNA synthesis using a functional assay. This method may be applied to clone other genes involved in negative regulation of the cell cycle, such as tissue specific differentiation and tumor suppression genes. Using this method, three inhibitor sequences have been cloned. One of these sequences (SDI-1) appears to be closely related to cellular senescence.

In detail, the invention provides a nucleic acid molecule that encodes a protein or polypeptide capable of inhibiting DNA synthesis in a recipient cell.

In particular, the invention provides a liposome preparation that comprises an SDI molecule, and particularly one that comprises:
  (a) a mixture of a polycationic and a neutral lipid; and
  (b) an SDI molecule selected from the group consisting of SDI-1 protein and an SDI-1-encoding nucleic acid molecule.

The invention particularly provides such liposome preparations wherein the polycationic lipid is 2,3-dioleyloxy-N-[2(sperminecarboxamido)-ethyl]-N,N-dimethyl-1-propanaminium-trifluoroacetate (DOSPA) and/or wherein the neutral lipid is dioleolyphosphatidylethanolamine (DOPE).

The invention particularly concerns the embodiments wherein (A) the SDI molecule is an SDI-1-encoding nucleic acid molecule that is operably linked to a promoter, but is separated from the operably linked promoter by a non-translated intervening polynucleotide and/or (B) wherein the SDI-1-encoding nucleic acid molecule is operably linked to a promoter, and contains a non-translated intervening polynucleotide which separates a region of the SDI-1-encoding nucleic acid that encodes part of SDI-1 from a region of the SDI-1-encoding nucleic acid that encodes a different part of SDI-1.

The invention also provides a method for preparing a liposome preparation of SDI molecules which comprises incubating liposomes that comprise a mixture of a polycationic and a neutral lipid with an SDI molecule selected from the group consisting of SDI-1 protein and an SDI-1-encoding nucleic acid molecule.

The invention also concerns a method of providing an SDI molecule to a cell which comprises:

(A) contacting the cell with a liposome preparation that comprises a mixture of a polycationic and a neutral lipid and an SDI molecule selected from the group consisting of SDI-1 protein and an SDI-1-encoding nucleic acid molecule; and (B) permitting the intracellular delivery of the SDI-1 molecule of the liposome preparation.

The invention also concerns an SDI-1-encoding nucleic acid molecule, operably linked to a promoter, but separated from the operably linked promoter by a non-translated intervening polynucleotide.

The invention also provides a method of transcribing an SDI-1-encoding nucleic acid molecule which comprises:

(A) providing to a cell the SDI-1-encoding nucleic acid molecule, operably linked to a promoter, but separated from the operably linked promoter by a non-translated intervening polynucleotide; and (B) permitting the promoter to mediate the transcription of the SDI-1-encoding nucleic acid molecule.

The invention also provides a nucleic acid molecule that encodes SDI-1, a fragment of SDI-1, an SDI-1 fusion protein or a mimetic or analog of SDI-1.

The invention also provides a protein or polypeptide capable of inhibiting DNA synthesis in a recipient cell, wherein the protein or polypeptide is SDI-1, a fragment of SDI-1, an SDI-1 fusion protein or a mimetic or analog of SDI-1.

The invention additionally provides a method for treating a disease of undesired cellular proliferation which comprises providing to a recipient a nucleic acid molecule that encodes SDI-1, a fragment of SDI-1, an SDI-1 fusion protein, an SDI-1 mimetic, or an analog of SDI-1.

The invention additionally provides a method for treating a disease of undesired cellular proliferation which comprises providing to a recipient a protein or polypeptide capable of inhibiting DNA synthesis in a recipient cell, wherein the protein or polypeptide is SDI-1, a fragment of SDI-1, an SDI-1 fusion protein or a mimetic or analog of SDI-1.

The invention additionally provides a method for treating a disease of undesired cellular quiescence which comprises providing to a recipient a nucleic acid molecule that encodes an inhibitor of SDI-1.

The invention additionally provides a method for treating a disease of undesired cellular quiescence which comprises providing to a recipient a protein, polypeptide, or organic molecule capable of inhibiting SDI-1.

BRIEF DESCRIPTION OF THE FIGURES

FIGS. 2A, 2B and 2C identify cDNA clones inhibitory to young cell DNA synthesis. The different bars represent independent transfection experiments for individual plasmids, * indicates not done, a negative number indicates labeling indices higher than the controls. Each graph shows results from a different pool of plasmids.

FIGS. 5A–5D provide the nucleotide and amino acid sequences of SDI-1 cDNA.

DETAILED DESCRIPTION OF THE INVENTION

I. Cellular Senescence

Figure 1:
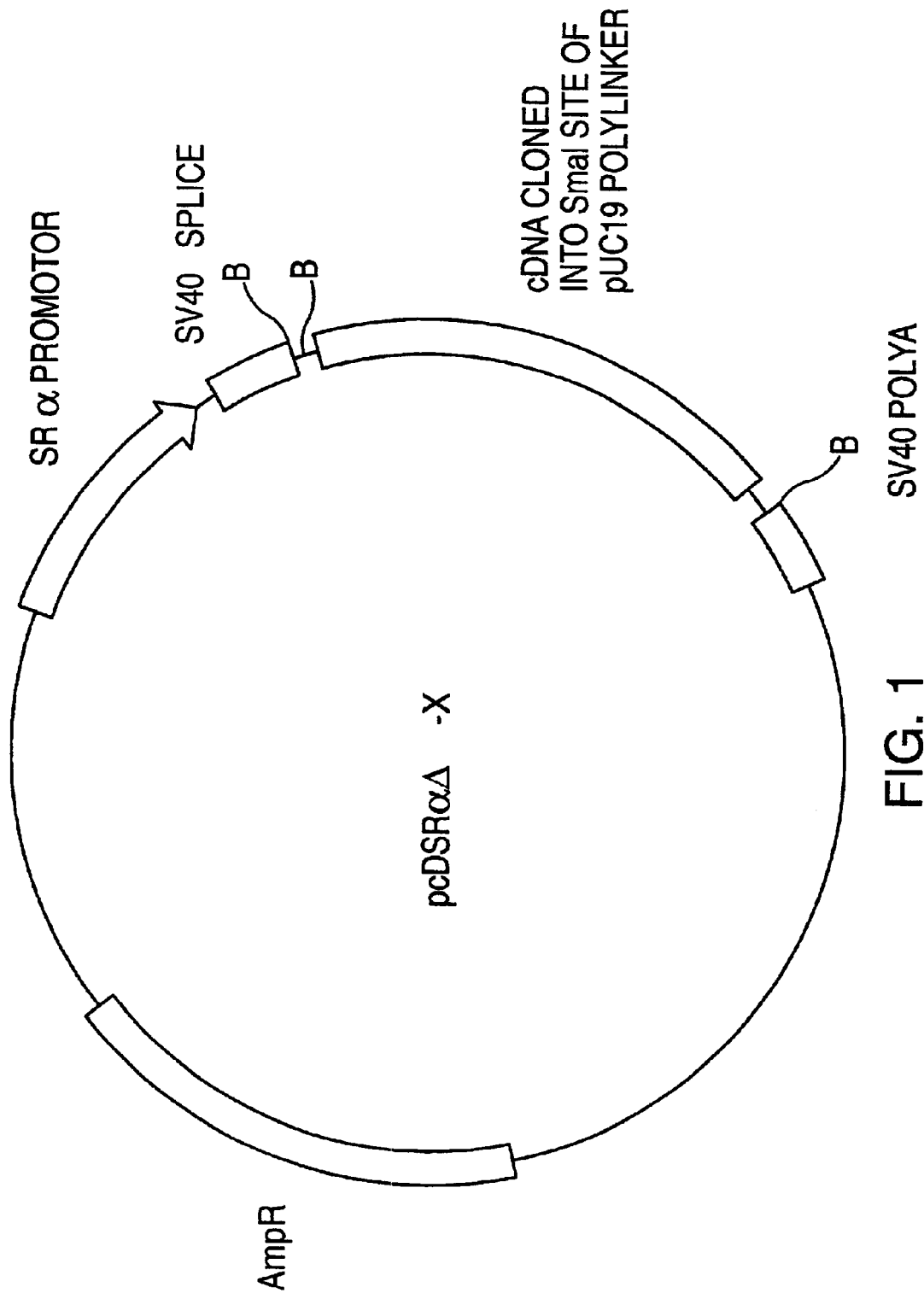
FIG. 1 shows the structure of the cDNA cloning and expression vector, pcDSRαΔ (B represents BamHI site).

Replicative senescence of normal human diploid fibroblasts in culture is a well established and widely accepted model for cellular aging (Hayflick, L., *Exp. Cell Res.* 37:611–636 (1965); Norwood, T. H., and Smith, J. R., In: *Handbook of the Biology of Aging* (2nd ed.) C. E. Finch and E. L. Schneider, eds. Van Nostrand, New York pp. 291–311 (1985); Goldstein, S., *Science* 249:1129–1133 (1990)). After a limited number of population doublings, as cells become senescent, they lose the capability to divide and display a large and flattened morphology. The causative mechanisms underlying this phenomenon are not yet understood, despite the many observations that characterize senescent cells at the biochemical and molecular levels.

One- and two-dimensional protein gel analyses have revealed that there are few senescent cell-specific marker proteins (Lincoln, D. W. et al., *Exp. Cell Res.* 154:136–146 (1984); Wang, E., *J. Cell Biol.* 100:545–551 (1985); Scottie, J. et al., *J. Cell Physiol.* 131:210–217 (1987); Bayreuther, K. et al., *Proc. Natl. Acad. Sci. USA.* 85:5112–5116 (1988)). Antigenic determinants that specify senescent cells have been found on the plasma membrane (Porter, M. B. et al., *J. Cell Physiol.* 142:425–433 (1990)). Components of extracellular matrix, such as fibronectin and collagenase, have been found to be over-expressed in senescent cells (West, M. D. et al., *Exp. Cell Res.* 184:138–147 (1989); Kumazaki, T. et al., *Exp. Cell Res.* 195:13–19 (1991)). However, the relevance of these observations to cellular senescence is not clear.

The cell cycle has been found to be regulated and driven by growth factors. Growth factors act throughout the first gap ($G_1$) phase of the cell cycle by binding to specific cell surface receptors, which in turn trigger signaling cascades that ultimately govern the transcription of both immediate and delayed early response genes. The growth cycle is controlled by kinases, especially "cyclin-dependent kinases" ("CDKs"), by the "cyclins" themselves, and by phosphatases (Sherr, C. J., *Cell* 73:1059–1065 (1993), herein incorporated by reference).

Considerable effort has been expended to identify the mammalian kinases that are involved in the DNA synthesis cycle. In vertebrate cells, a family of cyclins has been identified (see, Xiong, Y. et al., *Cell* 71:505–514 (1992)). Gene sequences encoding several of these cyclins have been isolated (Motokura, T. et al., *Nature* 350:512–515 (1991); Xiong, Y. et al., *Cell* 65:691–699 (1991); Lew, D. J. et al., *Cell* 65:1197–1206 (1991); Xiong, Y. et al., *Curr. Biol.* 1:362–364 (1991); Matsushime, H. et al., *Cell* 65:701–7139 (1991); Inaba, T. et al., *Genomics* 13:565–574 (1992); Xiong, Y. et al., *Genomics* 13:575–584 (1992)).

The D cyclins interact with CDK2, CDK4 and with CDK5, in order to initiate the growth cycle at the $G_1$ stage (Matsushime, H. et al., *Cell* 65:701–7139 (1991); Sherr, C. J., *Cell* 73:1059–1065 (1993)). Cyclin E/CDK2 interactions regulate the initiation of S phase (Lew, D. J. et al., *Cell* 66:1197–1206 (1991); Koff, A. et al., *Cell* 66:1217–1228 (1991)). Cyclin A has been suggested to interact with CDK2 to regulate the S phase of the growth cycle (Sherr. C. J., *Cell* 73:1059–1065 (1993)). Cyclins A and B are believed to interact with CDC2 to mediate termination of S phase and initiation of $G_2$ phase (Norbury, C. et al., *Ann. Rev. Biochem.*

61:441–470 (1992); Fang, F. et al., *Cell* 66:731–742 (1991); Walker, D. H. et al., *Nature* 354:314–317 (1991).

Recently, changes in the expression of several growth regulated genes have been identified. Expression of c-fos CDC2, cyclins A and B have been found to be impaired in senescent cells (Seshadri, T. et al., *Science* 247:205–209 (1990)). Similarly, senescent cells evidence an inability to phosphorylate the retinoblastoma protein (Stein, G. H. et al., *Science* 249:666–669 (1990)). These observations could potentially explain the inability of the cells to enter S phase, since they are all deteriorative changes of growth promoting gene expression, however, it is not clear whether they are the cause or result of senescence.

One additional change in gene expression that could have a causal role in senescence is the inhibitor(s) of DNA synthesis produced by senescent but not young fibroblasts (see, Spiering, A. I. et al., *Exper. Cell Res.* 195:541–545 (1991). Evidence for the existence of the inhibitor(s) was first obtained from heterokaryon experiments in which senescent cells inhibited initiation of DNA synthesis in young nuclei within the heterokaryon (Norwood, T. H., et al., *Proc. Natl. Acad. Sci. USA.* 71:2231–2234 (1974); Pereira-Smith, O. M., and. Smith, J. R., Somat. *Cell Genet.,* 8:731–742 (1982)). Studies with cybrids involving senescent cytoplasts and whole young cells lent further support for the presence of a surface membrane associated protein inhibitor of DNA synthesis in senescent cells (Dresher-Lincoln, C. K., and Smith, J. R., *Exp. Cell Res.* 153:208–217 (1984)). This was directly demonstrated when surface membrane enriched preparations from senescent cells or proteins extracted from the membranes were found to inhibit DNA synthesis when added to the: culture medium of young cells (Pereira-Smith, O. M. et al., *Exp. Cell Res.* 160:297–306 (1985); Stein, G. H., and Atkins, L., *Proc. Natl. Acad. Sci. USA.* 83:9030–9034 (1986)). Purification of that inhibitor by biochemical methods has been unsuccessful to date. However, in microinjection experiments, the presence of a high abundance of DNA synthesis inhibitory messenger RNA has been demonstrated (Lumpkin, C. K. et al., *Science* 232:393–395 (1986)).

In order to attempt to clone the gene(s) coding for the DNA synthesis inhibitor(s), a functional screening procedure was employed. This method led to the isolation and identification of three cDNA species that exhibit DNA synthesis inhibitory activity when introduced into young cycling cells. These molecules are a preferred class of the molecules referred to herein as "senescent cell derived inhibitors" ("SDI").

Subsequent to the cloning, isolation, sequencing and characterization of the SDI molecules of the present invention (see, for example PCT Application Publication No. US93/12251), other research groups conducted similar efforts. Such subsequent efforts have described the SDI-1 molecule of the present invention as WAF1, CIP1, PIC1 and p21 (Harper, J. W. et al, *Cell* 75:805–816 (1993); EI-Deiry, W. S. et al., *Cell* 75:817–825 (1993); Xiong, Y. et al., *Nature* 366:701–704 (1993); Hunter, T. et al., *Cell* 75:839–841 (1993)).

II. The Cloning of Inducers of Cellular Senescence

In the practice of the present invention, an efficient method for the molecular cloning of the DNA synthesis inhibitory sequences present in senescent human diploid fibroblasts is preferably employed. As is often the case when attempting to clone biologically important genes, it may not be possible to purify a desired gene responsible for cellular senescence, even though the activity of its products could be readily detected.

One method that might be envisioned for identifying such a gene sequence would be to employ a differential or subtractive screening of a senescent cell derived cDNA library. This method has been used to identify cDNA molecules that are overexpressed in cells from Werner Syndrome patients (Murano, S. et al., *Molec. Cell. Biol.* 11:3905–3914 (August 1991)). Werner Syndrome is a rare inherited disorder. It is characterized by premature aging. The relevance of Werner Syndrome to natural aging is unknown.

Unfortunately, such screenings would identify a number of genes that, although important for the characterization of senescent cells, would not be primarily responsible for senescence. Furthermore, technical limitations in cloning full-length cDNA make it difficult to determine the function of genes cloned by these methods. For these reasons, such differential methods are nether generally suitable, or the most desirable method of identifying senescence-related gene sequences.

In contrast, expression screening provides a preferred method for identifying and isolating such senescence-related gene sequences. In such a screening method, the cDNA is cloned directly into a vector that is capable of expressing the cloned gene in a recipient cell. The recipient cells can thus be directly screened for any inhibition in DNA synthesis.

In expression screening, the most important step is the synthesis of cDNAs. Enzymes should be carefully chosen to be free of impurities. The cDNA, synthesis is preferably repeated several times to ensure that satisfactory results (i.e faithful reverse transcription, and full length transcript size) will be obtained. Finally, the cDNA products are preferably size fractionated to eliminate fragmented and prematurely terminated cDNA products. Double-stranded cDNA products are then preferably divided into fractions based on size, i.e., 0.5–2.0, 2.0–4.5, and 4.5–10 kb fractions. The 2–4.5 kb cDNA fraction was used to make the cDNA library on the assumption that many membrane associated proteins have a relatively high molecular weight. The cDNAs are inserted into a suitable expression vector, preferably pcDSRαΔ, in which the inserted sequences can be transcribed at high levels in young cells.

The most preferred transfection procedure is DEAE dextran-mediated transfection, carried out under conditions that allow for transient expression in a high percentage of young cycling cells. Since the transfection frequencies could vary from experiment to experiment, the cDNA pool plasmids were transfected along with a marker plasmid, such as pCMVβ (encoding β-galactosidase), and the labeling index was assayed in only β-galactosidase positive cells. Generally, co-expression of transfected genes is quite high, since transfection competent cells will accept multiple plasmids. This simple co-transfection method enabled the evaluation of DNA synthesis in cells expressing exogenous DNA.

The amount of plasmid to be co-transfected can be readily determined from pilot experiments. When the correlation between the transfection frequency and the amount of plasmid added is examined using a marker plasmid, maximum efficiency is obtained at a range of 100–500 ng of plasmid. Taking into account this result, the cDNA library is preferably divided into small pools in which every pool contained five independent plasmid clones. Then the co-transfection is carried, out with approximately 100 ng of pCMVβ and approximately 400 ng of cDNA plasmid. These parameters were found to maximize the co-expression of cDNA in β-galactosidase positive cells without decreasing the transfection frequency of the marker plasmid.

Figure 2C:
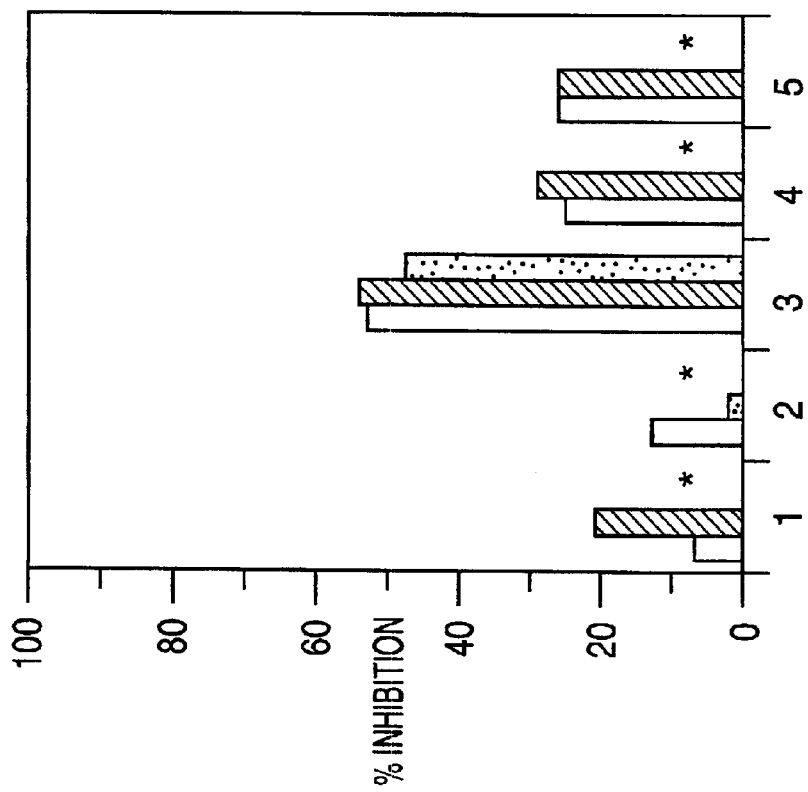

After the second round of screening, single plasmids which showed strong inhibition of DNA synthesis can be successfully isolated from the pool that tested positive during the first round screenings (FIGS. 2A, 2B, 2C). In FIGS. 2A, 2B and 2C, cDNA pools which showed positive in the first round screenings were divided into individual plasmid, and transfected again. For every cDNA pool (A, B and C in FIGS. 2A, 2B, 2C, respectively), plasmid No. 1 to 5 represents the result of each single plasmid transfection. In pool B, No. 1 plasmid was found to be only the empty vector. The inhibitory activities of the plasmids are preferably further confirmed by nuclear microinjection experiments. Such experiments provide more direct evidence that the isolated plasmids contain sequences capable of inhibiting DNA synthesis.

III. The Molecules of the Present Invention

The agents of the present invention (collectively referred to as "SDI molecules") are capable of either inducing the inhibition of DNA synthesis in active cells, or suppressing such inhibition in senescent or quiescent cells. As such, they may be used for a wide range of therapies and applications.

The SDI molecules of the present invention include SDI nucelic acid molecules (e.g., SDI-1 encoding nucleic acid molecules, SDI-1 fragment encoding molecules, SDI-1 fusion encoding molecules, SDI antisense molecules, SDI triplex repessor molecules, etc.), SDI protein molecules (i.e. SDI-1, and its fusions and fragments, antibodies to such molecules, and protein analogs and mimetics of such molecules), and non-protein mimetics and analogs of such molecules.

Such molecules may either naturally occurring or non-naturally occuring. A naturally occuring SDI-1 molecule may be purified, such that one or more molecules that is or may be present in a naturally occuring preparation containing the molecule has been removed or is present at a lower concentration than that at which it would normally be found.

The molecules of the present invention may be either nucleic acids, proteins, carbohydrates, or, more preferably, organic molecules that have a tertiary structure which resembles or mimics the structure of a SDI protein molecule. The present invention further concerns the use of biologically active fragments of molecules, such as SDI nucleic acid molecules, SDI protein molecules, etc. in lieu of or in addition to any naturally occurring SDI molecule. As used herein, a molecule is said to be "biologically active" with respect to cellular proliferation if it is capable of mediating an affect on the proliferative capacity of a recipient cell. Such biological activity may be a structural attribute, such as the capacity to mediate antisense repression, or the ability to bind at a particular nucleic acid site, or with a particular active site of a protein, receptor, etc. (or to compete with another molecule for such binding) Alternatively, such an attribute may be catalytic, and involve the capacity of the biologically active molecule to mediate a chemical reaction or response in a recipient cell.

The present invention permits the isolation of all such SDI molecules in a "purified" form. As used herein, an SDI molecule is said to be "purified" if it is present in a preparation that lacks a molecule that is normally associated with the SDI molecule in its natural state. Proteins, lipids, nucleic acid sequences that do not encode SDI molecules are examples of molecules that are naturally associated with SDI molecules.

A. SDI Nucleic Acid Molecules and Their Oligo-nucleotide or Polynucleotide Fragments A preferred class of SDI nucleic acid molecules includes the nucleic acid molecules: SDI-1, SDI-2, and SDI-3, and their biologically active fragments, To identify such fragments, the SDI nucleic acid molecules can be cleaved, as by mechanical methods or more preferably restriction endonuclease cleavage to thereby generate candidate fragments. Such fragments can then be provided to cells, and monitored for their capacity to inhibit DNA synthesis. In one embodiment, gene sequences that encode fragments of protein SDI molecules can be administered to a recipient cell.

By administering fragments of nucleic acid SDI molecules (with or without linked sequences) it is possible to assess whether a particular fragment of an SDI nucleic acid molecule has biological activity due to its structure. Thus, for example, such candidate SDI molecules could be introduced into either, a normal, immortalized, or tumor cell, and the capacity of the cell to undergo further proliferation can be monitored. In this manner, sequences that repress cellular proliferation, or induce quiescence can be identified.

Through the use of such; methods, nucleic acid molecules that encode the amino terminal half of SDI-1 have been found to exhibit the capacity to convert immortalized cells or tumor cells to a quiescent state. More specifically, nucleic acid molecules that encode SDI-1 amino acid residues 1–70 have been found to be capable of inducing cellular quiescence. The recognition that residues 1–70 contain a catalytic domain of SDI-1 indicates that other fragments of the SDI-1 encoding sequence have catalytic activity. Preferred candidate oligonucleotide fragments include nucleic acid molecules that encode SDI-1 amino acid residues: 5–70, 10–70, 15–70, 20–70, 25–70, 30–70, 35–70 or 40–70.

As discussed below, one aspect of the present invention concerns methods for determining the level of SDI-1 mRNA. Nucleic acid molecules that are capable of hybridizing to an SDI nucleic acid molecules can be used for such diagnostic purposes. As used herein, two nucleic acid molecules are said to be capable of hybridizing to one another if the two molecules are capable of forming an anti-parallel, double-stranded nucleic acid structure. The molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. As will be appreciated, complementary molecules need not exhibit "complete complementarity" (i.e. wherein every nucleotide of one of the molecules is complementary to a nucleotide of the other), but need only be sufficiently complementary in sequence to be able to form a stable double-stranded structure under defined solvent and salt concentrations. A nucleic acid molecule is said to be the "complement" of another nucleic acid molecule if they exhibiy complete complementarity. Conventional stringency conditions are described by Sambrook, J., et al., (In: *Molecular Cloning, a Laboratory Manual, 2nd Edition*, Cold Spring Harbor Press, Cold Spring Harbor, N.Y. (1989)), and by Haymes, B. D., et al. (In: *Nucleic Acid Hybridization, A Practical Approach*, IRL Press, Washington, D.C. (1985)), both herein incorporated by reference). Departures from complete complementarity are therefore permissible, as long as such departures do not completely preclude the capacity of the molecules to form a double-stranded structure.

The nucleic acid molecules that can be used to hybridize to an SDI nucleic acid molecule will preferably be shorter than such SDI molecule. Preferred molecules will be completely complementary to an SDI nucleic acid molecule, and will have a length of between about 15 to about 250 nucleotides, and most preferably about 15 to about 30 nucleotides.

Such nucleic acid molecules may be obtained using solid phase oligonucleotide synthetic methods, however, more preferably, such molecules will be obtained via the polymerase-mediated, template-dependent extension of a primer molecule that is complementary to a fragment of an SDI nucleic acid molecule. Such fragments of SDI nucleic acid molecules will have a length of between about 15 to about 250 nucleotides, and most preferably about 15 to about 30 nucleotides. Such fragments may be DNA or RNA, and may be incorporated into vectors, or be substantially free of other nucleic acid molecules.

B. The Proteins and Polypeptides Encoded by Nucleic Acid SDI Molecules

The present invention further includes the proteins and polypeptides encoded by the SDI nucleic acid molecules or their oligonucleotide fragments. The sequences of SDI nucleic acid molecules permits one to ascribe and identify encoded protein and polypeptide molecules that can be used either to suppress the inhibition of DNA synthesis associated with quiescence and senescence, or to induce such states in proliferating cells. The amino acid sequence of such molecules can be readily derived from the known relationship between the nucleotide sequence of a nucleic acid molecule, and the amino acid sequence of the protein it encodes. Therapeutically active proteins and polypeptides can be identified using a method that is analogous to the above-described method for identifying therapeutically active SDI nucleic acid fragments. By mutating such proteins, it is possible to identify molecules that have lost the capacity to inhibit DNA synthesis. Among such mutated molecules will be proteins that are capable of exerting a dominant effect sufficient to reverse the inhibitory effect of SDI-encoded proteins and polypeptides.

In one embodiment, such molecules are identified by cleaving nucleic acid SDI molecules, and then incorporating the cleavage fragments into translatable expression vectors. In this manner, a library of nucleic acid molecules, each producing a different peptide fragment can be obtained and evaluated. Such expression may be free of additional or extraneous protein, or may comprise a fusion of an SDI fragment to a particular fusion protein. The biological activity of the expressed proteins can be assessed either by introducing such fragments into recipient cells, and determining the affect of such introduction on quiescence or proliferation. Alternatively, such molecules can be passed through columns that have been pretreated to bind biologically active SDI molecules. Such columns may, for example, contain bound p53, SDI-1, RB, cyclin D, cdk2, p53- or RB-associated proteins, etc., in order to identify fragments that have the capacity to bind to such molecules.

Examples of protein fragment SDI molecules include the first 70 amino acids of SDI-1, which has a biological activity similar to that of SDI-1. Smaller fragments (such as those containing SDI-1 residues: 5–70, 10–70, 15–70, 20–70, 25–70, 30–70, 35–70 or 40–70) may also be employed. Protein fragments that possess SDI-1 amino acid residues 29–45 are particularly desirable. When conserved amino acid substitutions are considered, this region of SDI-1 exhibits 31% identity and 62% similarity to PCNA. Since SDI-1 and PCNA both interact with cyclin-Cdk complexes, the conserved region in common (SDI-1 amino acid residues 29–45) are believed to be involved in such interactions. Hence, fragments of SDI-1 that contain this conserved region comprise inhibitors of SDI-1, and may indeed exhibit SDI-1 function.

Typically, the SDI proteins and protein fragments will be produced free of any additional amino acid residues. Alternatively, the SDI proteins and protein fragments may be produced fused to an amino acid or to a polypeptide. Such synthesis may be accomplished using conventional peptide synthetic means, or, more preferably, using recombinant methods. Where fusion molecules are desired, such molecules may contain selectable cleavage sites such that the SDI portion of the fusion molecule may be cleaved from the remaining portion(s) of the fusion protein.

A particularly preferred fusion molecule results from fusing a glutathione S-transferase glutathione binding sequence to the amino terminus of the SDI molecule. Such fusion proteins can be readily recovered by their retention to a column. The fusion protein can be removed from the column by washing with glutathione. An GST-SDI-1 fusion protein can be produced by peptide synsthesis, such as by synthesizing the SDI protein as a fusion with glutathione S-transferase. Alternatively, recombinant DNA methods can be used to join a GST-encoding polynucleotide to a polynucleotide that encodes SDI-1 or a fragment thereof. The sequence of glutathione S-transferase (GST) is known, and vectors that contain this sequence have been described (see, Ross, V. L., et al., *Biochem, J.* 294:373–380 (1993); Comstock, K. E. et al., *J. Biol. Chem.* 268:16958–16965 (1993); Takahasi, Y. et al., *J. Biol. Chem.* 268:8893–8898 (1993); Klone, A. et al., *Biochem. J.* 285:925–928 (1992); Sternberg, G. et al., *Protein Express. Purif.* 3:80–84 (1992); Morrow, C. S. et al., *Gene* 75:3–12 (1989)).

An alternative preferred fusion molecule has an amino terminal $[His]_6$ leader sequence. The presence of such leader sequences does not substantially reduce the activity of the SDI proteins. More preferably, a leader sequence having the sequence MRGSHHHHHHGA [SEQ ID NO:4] coupled to the amino terminal methionine of SDI-1 will be employed.

A preferred fusion includes essentially all of the GST protein. An especially preferred fusion employs the GST of *Schistosoma japonicum*. The sequence of this GST is described by Smith et al (*Gene* 67:31 (1988)), and the polynucleotide that encodes this GST can be obtained commercially (pGEX-2T; Pharmacia). The DNA sequence encoding the GST of *Schistosoma japonicum* is shown as SEQ ID NO:5; the encoded amino acid sequence is shown in SEQ ID NO:6. Any of a variety of methods may be used to create such a preferred fusion; a detailed method is provided in Example 20. In one embodiment, a restriction endonuclease recognition site in the *Schistosoma japonicum* GST-encoding polynucleotide can be used to cleave that polynucleotide. The cleavage product can then be ligated to a polynucleotide that encodes a desired SDI molecule. Thus, for example, a preferred fusion can be made by cleaving the GST-encoding sequence of *Schistosoma japonicum* with BamHI so as to obtain a polynucleotide fragment that contains nucleotides 1–673 of the GST-encoding polynucleotide (the BamHI cleaving at a site located at nucleotides 673–678 of the molecule) and then ligating that fragment to an SDI gene sequence (such as a polynucleotide that encodes SDI-1). Where, for example, a polynucleotide that encodes SDI-1 is employed, the gene fusion would link the GST fragment to the SDI-1 polynucleotide such that, upon expression, a fusion protein containing the first 226 of the 232 amino acids of GST linked to the amino terminus of SDI-1 would be produced.

As discussed below, one aspect of the present invention concerns antibodies to SDI-1. The above-described proteins and polypeptides can be used to, elicit polyclonal or monoclonal antibodies that can be used in accordance with the methods of the present invention.

C. Functional Analogs of the SDI Molecules

The present invention also pertains to "functional analogs" of the SDI molecules. Such analogs include both "classical analogs" and "mimetic analogs." A classical analog of an SDI molecule is one that has a similar biological activity, and is chemically related to the SDI molecule. By way of illustration, a non-naturally occurring mutant protein having SDI activity would comprise a classical analog of a protein SDI molecule. Similarly, a mutated SDI nucleic acid molecule would comprise an example of a classical analog of an SDI gene sequence. Likewise, an SDI molecule isolated from a non-human mammalian species (such as a mouse, monkey, etc.) would comprise an example of a classical analog of an SDI gene sequence. In contrast, a "mimetic analog" of an SDI molecule retains the biological activity of the molecule, but will typically be unrelated chemically. An organic molecule whose structure mimics the active site of an SDI protein would comprise a "mimetic analog" of that protein. Similarly, non-nucleic acid molecules capable of binding to a nucleic acid binding site of SDI, or recognized by SDI would be a mimetic analog of that molecule.

Thus, functional analogs may be either an oligonucleotide or polynucleotide, a proteinaceous compound (including both glycosylated and non-glycosylated proteins), or a non-proteinaceous compound (such as a steroid, a glycolipid, etc.) provided that the agent mimics the function of either an entire SDI nucleic acid molecule, or an oligonucleotide or polynucleotide fragment thereof, or a protein or polypeptide encoded by such a molecule or fragment. Preferred classical analogs include polypeptides (including circular as well as linear peptides) whose sequences comprise the active catalytic or binding sites of an SDI protein, or oligonucleotide fragments of nucleic acid SDI molecules that are capable of either repressing or inducing SDI activity. Preferred mimetic analogs include polypeptides that are not fragments of an SDI protein, or mutants thereof, but nevertheless exhibit a capacity to induce quiescence in an SDI-like manner, or to induce cellular proliferation in the manner of an SDI antagonist.

Classical analogs can be identified either rationally, as described below, or via established methods of mutagenesis (see, for example, Watson, J. D. et al., *Molecular Biology of the Gene*, Fourth Edition, Benjamin/Cummings, Menlo Park, Calif. (1987). Significantly, a random mutagenesis approach requires no a priori information about the gene sequence that is to be mutated. This approach has the advantage that it assesses the desirability of a particular mutant on the basis of its function, and thus does not require an understanding of how or why the resultant mutant protein has adopted a particular conformation. Indeed, the random mutation of target gene sequences has been one approach used to obtain mutant proteins having desired characteristics (Leatherbarrow, R. J. *Prot. Eng.* 1:7–16 (1986); Knowles, J. R., *Science* 236:1252–1258 (1987); Shaw, W. V., *Biochem. J.* 246:1–17 (1987); Gerit, J. A. *Chem. Rev.* 87:1079–1105 (1987)). Alternatively, where a particular sequence alteration is desired, methods of site-directed mutagenesis can be employed. Thus, such methods may be used to selectively alter only those amino acids of the protein that are believed to be important (Craik, C. S., *Science* 228:291–297 (1985); Cronin, C. S. et al., *Biochem.* 27:4572–4579 (1988); Wilks, H. M. et al., *Science* 242:1541–1544 (1988)).

Nucleic acid analogs of SDI molecules can be evaluated by their capacity to be regulated by p53, or other cellular regulators. Alternatively, their capacity to affect cellular proliferation can be directly assayed. For protein analogs of SDI such studies can be accomplished by purifying the mutant protein, and comparing its activity to an SDI molecule. The analysis of such mutants can also be facilitated through the use of a phage display protein ligand screening system (Lowman, H. B. et al., *Biochem.* 30:10832–10838 (1991); Markland, W. et al., *Gene* 109:13–19 (1991); Roberts, B. L. et al., *Proc. Natl. Acad. Sci. (U.S.A.)* 89:2429–2433 (1992); Smith, G. P., *Science* 228:1315–1317 (1985); Smith, R. P. et al., *Science* 248:1126–1128 (1990), all herein incorporated by reference)). In general, this method involves expressing a fusion protein in which the desired protein ligand is fused to the C-terminus of a viral coat protein (such as the M13 Gene III coat protein, or a lambda coat protein).

Mimetic analogs of naturally occurring SDI molecules may be obtained using the principles of conventional or of rational drug design (Andrews, P. R. et al., In: *Proceedings of the Alfred Benzon Symposium*, volume 28, pp. 145–165, Munksgaard, Copenhagen (1990); McPherson, A. *Eur. J. Biochem.* 189:1–24 (1990); Hol, W. G. J. et al., In: *Molecular Recognition: Chemical and Biochemical Problems*, Roberts, S. M. (ed.); Royal Society of Chemistry; pp. 84–93 (1989); Hol, W. G. J., *Arzneim-Forsch.* 39:1016–1018 (1989); Hol, W. G. J., *Agnew. Chem. Int. Ed. Engl.* 25:767–778 (1986) all herein incorporated by reference).

In accordance with the methods of conventional drug design, the desired mimetic molecules are obtained by randomly testing molecules whose structures have an attribute in common with the structure of a "native" SDI molecule, or a molecule that interacts with an SDI molecule. The quantitative contribution that results from a change in a particular group of a binding molecule can be determined by measuring the capacity of competition or cooperativity between the native SDI molecule and the putative mimetic.

In one embodiment of rational drug design, the mimetic is designed to share an attribute of the most stable three-dimensional conformation of an SDI molecule. Thus, the mimetic analog of a SDI molecule may be designed to possess chemical groups that are oriented in, a way sufficient to cause ionic, hydrophobic, or van der Waals interactions that are similar to those exhibited by the SCI molecule. In a second method of rational design, the capacity of a particular SDI molecule to undergo conformational "breathing" is exploited. Such "breathing"—the transient and reversible assumption of a different molecular conformation—is a well appreciated phenomenon, and results from temperature, thermodynamic factors, and from the catalytic activity of the molecule. Knowledge of the 3-dimensional structure of the SDI molecule facilitates such an evaluation. An evaluation of the natural conformational changes of an SDI molecule facilitates the recognition of potential hinge sites, potential sites at which hydrogen bonding, ionic bonds or van der Waals bonds might form or might be eliminated due to the breathing of the molecule, etc. Such recognition permits the identification of the additional conformations that the SDI molecule could assume, and enables the rational design and production of mimetic analogs that share such conformations.

The preferred method for performing rational mimetic design employs a computer system capable of forming a representation of the three-dimensional structure of the SDI molecule (such as those obtained using RIBBON (Priestle, J., *J. Mol. Graphics* 21:572 (1988)), QUANTA (Polygen), InSite (Biosyn), or Nanovision (American Chemical Society). Such analyses are exemplified by Hol, W. G. J. et al. (In: *Molecular Recognition: Chemical and Biochemical Problems*, Roberts, S. M. (ed.); Royal Society of Chemistry;

pp. 84–93 (1989)), Hol, W. G. J. (*Arzneim-Forsch.* 39:1016–1018 (1989)), and Hol, W. G. J., *Agnew. Chem. Int. Ed. Engl.* 25:767–778 (1986)).

In lieu of such direct comparative evaluations of putative SDI analogs, screening assays may be used to identify such molecules. Such an assay will preferably exploit the capacity of the SDI analog to affect cellular proliferation or quiescence. Alternatively, the molecules may be applied to a column containing a binding ligand, such as p53, Rb, cyclin D, etc., and the capacity of the molecule to bind to the column may be evaluated in comparison to the SDI molecule. Alternatively, a mutated SDI molecule (that inhibits the SDI-mediated inhibition of DNA synthesis) can be administered with a suspected antagonist compound. The cells would in this case be monitored to determine whether the compound is able to re-establish an inhibition of DNA synthesis.

Such assays are particularly useful for identifying peptide or oligonucleotide fragments or mimetics of SDI molecules, or analogs of such molecules. Thus, for example, one may incubate cells in the presence of either an oligonucleotide or a peptide SDI analog (or fragment) and a suspected antagonist compound. The cells would be monitored in order to determine whether the compound is able to impair the ability of the SDI oligonucleotide to inhibit DNA synthesis. As indicated above, column competition assays could alternatively be conducted. Thus, desired SDI classical and mimetic analogs may be identified by a variety of means.

Significantly, an appreciation of the mechanisms through which SDI molecules mediate their inhibition of DNA synthesis provides an alternative, or complimentary, approach to the isolation and recognition of analogs.

As indicated above, cyclin-dependent kinases play an important role in controlling the process of cellular DNA synthesis (Draetta, G. et al., *Trends Biol. Sci.* 15:378–383 (1990)). The SDI molecules of the present invention may be used to dissect the role of such kinases, and the involvement of such cyclins, and to thereby identify SDI analogs that can be used to inhibit DNA synthesis. For example, the D-type cyclins are believed to play a role in the G1 or S phase of DNA synthesis (Xiong, Y. et al., *Cell* 71:505–514 (1992)). The level of cyclin D/cyl1 protein increases throughout G1, declines during S and G2, and reaches a nadir after mitosis (Matsushime, H. et al., *Cell* 65:701–7139 (1991); Klyokawa, H. et al., *Proc. Natl. Acad. Sci. (U.S.A.)* 89:2444–2447 (1992); Xiong, Y. et al., *Cell* 71:505–514 (1992)).

Xiong, Y. et al. (*Cell* 71:505–514 (1992)) reported the existence of a 21 kd polypeptide that associates with cyclin D1 and CDK2. An immunological precipitation method was used in which radiolabelled extracts of cells were incubated in the presence of anti-cyclin antibodies. Proteins that associated with these antibodies were subjected to electrophoresis, and visualized.

The sequence of this 21 kd polypeptide has now been determined, and found to be encoded by SDI-1. Thus, since SDI-1 encode molecules inhibit DNA synthesis, the present invention establishes a biological role for the 21 kd protein (e.g., controlling the transit of the cells from $G_1$ to S, and from S to $G_2$. Moreover, since the SDI-1 encoded protein interacts with cyclin D1 and CDK2, the present invention establishes that agents that inhibit or reduce this interaction will be analogs of the SDI molecules.

The immunological precipitation method used by Xiong, Y. et al. (*Cell* 71:505–514 (1992)) to demonstrate the association of the 21 kd polypeptide and the cyclin D1 and CDK2 molecules may be exploited to determine the mechanism or pathway through which other SDI molecules mediate their inhibitory effect, and thereby permit the identification of other analogs.

For example, cells infected with an SDI-2 or SDI-3 sequence, or with antisense molecules for either can be analyzed to determine whether they express any of the proteins that have been previously shown to bind to a cyclin molecule. This can most readily be done by determining whether a particular protein is immunoprecipitated when an extract of treated cells is incubated with an anti-cyclin antibody. Since such a method identifies the molecules with which the SDI molecules interact, it establishes the pathway through which such SDI molecules mediate their inhibitory action. Molecules that impair or effect that pathway are analogs of such SDI molecules. Thus, the methods of the present invention can be used to identify inhibitors of any of the regulators of the cell cycle. Indeed, the SDI-1 protein has been found to interact with CDK4 and CDK5 as well as CDK2. Thus, it is likely that the SDI-1 protein interacts with multiple CDK and cyclin molecules.

Thus, the recognition that SDI molecules exert their control over cellular proliferation through interactions with cylins and CDK molecules provides an alternate approach to the identification of SDI analogs. In a similar manner, the recognition that other cellular regulators mediate their actions by regulating SDI transcription or expression, provides yet another alternate method for identifying SDI analogs.

For example, the transcription of the SDI-1 gene has been found to be regulated by "tumor suppressor" genes, and most notably by the p53 tumor suppressor gene. Indeed, the "tumor suppressor" capacity of p53 results from its capacity to induce SDI-1 expression, and thereby induce cellular quiescence in tumor cells.

The p53 gene has been previously found to encode a tumor-suppressing protein (Sager, R.,; *Science* 246:1406–1412 (1989); Finlay, C., *Cell* 57:1083 (1989); Weinberg, R. A., *Scientific Amer.*, September 1988, pp 44–51); Lane, D. et al. (*Genes Devel.* 4:1–8 (1990)). The p53 gene has also been found to play a protective role against the transforming effects of Friend erythroleukemia virus (Munroe, D. et al. *Oncogene* 2:621 (1988)), and to influence chromosome stability, differentiation and quiescence, and cell proliferation (Sager, R., *Science* 246:1406–1412 (1989)). It has been found that wild type p53 is necessary for cell cycle arrest following ionizing radiation and the constitutive expression of wild type p53 can arrest mammalian cells in G1. The ability to induce cell cycle arrest is thought to be related to p53's tumor suppressor function. The protein encoded by the p53 gene is a nuclear protein that forms a stable complex with both the SV40 large T antigen and the adenovirus E1B 55 kd protein.

Approximately 50% of all tumor cells evidence a mutation that diminishes or obliterates p53 expression. The p53 gene has been implicated as having a role in colorectal carcinoma (Baker, S. J. et al., *Science* 244:217–221 (1989)). Studies have shown that allelic deletions that encompass the p53 locus occurred in over 75% of colorectal carcinomas (Baker, S. J. et al., *Science* 244:217–221 (1989)). The deletion of the region was found to mark a transition from a (benign) adenocarcinoma stage to a (malignant) carcinomatous stage (Vogelstein, B. et al., *New Engl. J. Med.* 319:525 (1988)).

Similar deletions in chromosome 17 have been identified in a wide variety of cancers including breast and lung cancers (Mackay, J. et al., *Lancet ii:*1384 (1988); James, C. D. et al., *Canc. Res.* 48:5546 (1988); Yakota, J. et al., *Proc.*

*Nat'l. Acad. Sci. (U.S.A.)* 84:9252 (1987); Toguchida et al., *Canc. Res.* 48:3939 (1988)). A variety of human tumors (brain, colon, breast, lung) are characterized by cells that have lost one of the two normal p53 alleles, and have sustained a point mutation in the remaining p53 allele (Nigro et al., *Nature* 342:705–708 (1989)). Fearon et al. (*Cell* 61:759–767 (1990)) have hypothesized that both point mutations and deletions in the p53 alleles may be required for a fully tumorigenic phenotype. These findings suggest that the p53 gene may have a role in many types of cancers.

Recent evidence has suggested that a mutation in the p53 gene may be responsible for the Li-Fraumeni Syndrome, a rare human genetic disorder (Malkin, D. et al., *Science* 250:1233–1238 (1990); Marx, J., *Science* 250:1209 (1990), both references herein incorporated by reference). Individuals afflicted with this disease are highly susceptible to several malignant tumors—breast carcinomas, soft tissue sarcomas, brain tumors, osteosarcomas, leukemia, and adrenocortical carcinoma. The disease is also associated with a higher incidence of melanoma, gonadal germ cell tumors, and carcinomas of the lung, pancreas and prostate (Li, F. P. et al., *Ann. Intern. Med.* 71:747 (1969); Birch, J. M. et al., *J. Clin. Oncol.* 8:583 (1990); Birch, J. M. et al., *Brit. J. Canc.* 49:325 (1984); Li, F. P. et al., *Canc. Res.* 48:5358 (1988); Williams, W. R. et al., *Familial Canc., 1st Int. Res. Conf.* p. 151 (Karger, Basel, 1985); Strong, L. C. et al., *J. Natl. Canc. Inst.* 79:1213 (1987)).

Despite the extensive prior characterization of the biological role of the p53 gene, the mechanism through which its gene product mediated its tumor suppressor activity had not been previously elucidated. One aspect of the present invention relates to the discovery of that this mechanism involves SDI-1. Normal p53 protein increases the expression of SDI-1, and such increased expression suppresses cellular proliferation. In tumor cells that lack p53 function, SDI-1 levels are quite low, thus permitting cellular proliferation to occur.

The physiological significance of inhibition of cell proliferation by overexpression of SDI-1 is strengthened by the finding that SDI-1 can inhibit the kinase activity of cyclin/cdk2 complexes. Addition of a GST-SDI-1 fusion protein to cyclin/cdk2 complexes immunoprecipitated from HeLa cell extracts by cdk2 antisera resulted in half maximal inhibition of histone H1 kinase activity.

Thus, molecules that inhibit the tumor suppressor activity of p53 are antagonists of SDI-1; similarly, molecules that enhance the tumor suppressor activity of p53 protagonists of SDI-1, and are also encompassed by the present invention.

In normal human cells, SPI-1 has been found to exist as a complex with a cyclin, a CDK, and the proliferating cell nuclear antigen, "PCNA" (Waga, S. et al., *Nature* 369:574–578 (1994), herein incorporated by reference). PCNA is involved in the excision repair pathway through which cells repair damaged DNA. SDI-1 acts to block PCNA's ability to activate DNA polymerase δ. Thus, if cellular DNA is damaged before S phase, the induction of p53 leads to the transcriptional activation of the SDI-1 gene. The expressed SDI-1 protein complexes with CDK/cyclin-mediated DNA replication, and thus permits PCNA to mediate the excision repair of the damage. If the cellular DNA is damaged during S phase, excision repair would lead to increased damage potential. Hence, when damage occurs during S phase, the expressed SDI-1 protein complexes with PCNA to halt the replication process. As demonstrated below (Example 22), a 23 kD protein has been identified that exhibits the characteristics of an inactive, phosphorylated derivative of the SDI-1 protein. This derivative may be involved in the mechanism through which SDI-1 inhibition of PCNA is relieved after the completion of the DNA repair process.

Such an understanding of the interrelationship between SDI-1 and PCNA may be used to identify antagonists or mimetics of SDI-1. Thus, for example, molecules that inhibit the capacity of SDI-1 to complex with PCNA in cells undergoing S phase comprise antagonists and inhibitors of SDI-1 action. Conversely, molecules that enhance the capacity of SDI-1 to complex with PCNA in cells undergoing S phase comprise SDI-1 mimetics.

D. Antagonists of the SDI Molecules

The present invention thus also pertains to antagonists of the SDI molecules. Such antagonists may comprise SDI analogs that compete with, or that inhibit SDI function. Alternatively, such antagonists may comprise analogs of molecules such as cell cyclins or p53, that interact with SDI molecules.

Any of a variety of methods can be used to identify polypeptides or non-proteinaceous molecules that inhibit or repress SDI function. Such molecules can be evaluated to determine whether they compete with normal SDI molecules, or whether their presence in a cell affects the capacity of an SDI molecule to induce a quiescent state. For example, nucleic acid molecules that competitively bind p53 molecules are antagonists of SDI molecules. Such competitors can be readily identified using affinity columns, or by DNAse-footprinting methods.

Analogs of p53, or other tumor suppressor proteins, that are capable of interacting with and activating SDI sequences are an additional class of antagonists. Inhibitors of p53 (and other tumor suppressors) are likewise antagonists of the SDI molecules. Such molecules may be obtained by, for example, mutagenizing p53-encoding cDNA, and identifying p53 mutants that retain the capacity to bind to SDI-1 gene sequences or to SDI-1 proteins, but are otherwise inactive. The sequences of the cDNA and genomic forms of the p53 gene have been determined (Pennica, D. et al., *Virol.* 134:477–482 (1984); Jenkins, J. et al., *Nature* 312:651–654 (1984); Oren, M. et al., *EMBO. J.* 2:1633–1639 (1983); Zahut-Houri, R. et al., *Nature* 306:594–597 (1983), all of which references are herein incorporated by reference).

Alternatively, candidate inhibitors can be provided to a recipient cell and their capacity to impair normal p53 function can be ascertained. For example, such molecules can be tested for their capacity to prevent p53 from forming complexes with the SV40 large T antigen (see, DeCaprio, J. A. et al., *Cell* 54:275–283 (1988); Crawford, L. V., *Int. Rev. Exper. Pathol.* 25:1–50 (1983)).

Similarly, a variety of means can be exploited in order to identify nucleic acid molecules that inhibit or repress SDI-mediated inhibition of DNA synthesis. For example, the SDI nucleic acid sequences can be mutated, and the mutated sequences provided to cells in order to identify cells that do not exhibit an inhibition of DNA synthesis, and which have therefore received the desired mutated SDI sequences. In yet another method, the SDI gene sequences of immortalized cell lines can be evaluated to determine whether they contain mutated SDI genes that have lost the capacity to mediate cellular quiescence. In such manner, it has been determined that some immortalized cells (approximately 10%) carry a mutation in the SDI-1 gene that results in the substitution of arginine at amino acid residue 31 of SDI-1 (in place of the serine residue normally found at this position). Such a finding also implicates residue 31 of SDI-1 as being relevant to the active site or conformation of SDI-1. Since DNA from 12 normal Caucasian donors did not have this SDI-1 substitution, it is unlikely that the $Arg_{31}$ SDI-1 variant reflects a polymorphism rather than a mutation.

Other mutant SDI proteins have been identified by screening the SDI proteins of various cell lines. Thus, for example, SDI-1 mutants have been identified in which the valine normally found at amino acid residue 54 has been replaced with alanine, or in which the threonine normally found at amino acid residue 80 has been replaced with methionine.

Alternatively, mutated SDI sequences expressed from such nucleic acid molecules can be evaluated for their capacity to bind p53 protein, or the gene products of other tumor suppressor genes such as rb, etc.

In yet another embodiment, "triplex" nucleic acid molecules may be used to provide the desired therapy. A "triplex" molecule is a nucleic acid molecule that is capable of binding to double-stranded DNA in a manner sufficient to impair its transcription. Such an oligonucleotide can be of any length that is effective for this purpose. Preferably, the oligonucleotide will be about 10–30 nucleotides in length, most preferably, about 15–24 nucleotides in length. Triplex oligonucleotides are disclosed by Hogan, U.S. Pat. No. 5,176,996 and by Varma et al., U.S. Pat. No. 5,175,266.

The triplex oligonucleotides will preferably be about 20 nucleotides or more in length, and designed to bind to region of the SDI-1 gene that has a nucleotide sequence that is either about ⅔ purine or about ⅔ pyrimidine. In designing the sequence of the triplex oligonucleotide, the oligonucleotide is constructed to have a G residue when the complementary location in the target region is a GC base pair and a T residue when the complementary location in the target region is an AT base pair.

The sequence of the SDI-1 gene may differ from that of the cDNA if the gene contains intervening non-translated sequences ("introns"). In one embodiment, the genomic SDI-1 sequence is obtained and evaluated for the presence of regions that comport with the above-described preferred ratio of purines to pyrimidines. Such genomic sequences can be obtained by screening genomic libraries with oligonucleotides probes (e.g., 20–50 residues in length) having sequences selected from that of SEQ ID NO:1. Methods for screening genomic libraries are known in the art.

Alternatively, the SDI-1 cDNA sequence can be employed to generate suitable triplex molecules. An analysis of several hundred genes having intervening sequences ("introns") and translated sequences ("exons") has revealed that the intron-exon boundaries have defined upstream and downstream consensus sequences (Mount, S. M., *Nucl. Acids Res.* 10:459–472 (1982), herein incorporated by reference. The excision of the introns from mRNA precursor molecules removes most of these concensus sequences, and fuses the mRNA to create either a "CAGG" or an "AAGG" exon-exon boundary in the mRNA. Thus suitable target regions of the SDI-1 molecule will preferably (1) be at least 20 nucleotides in length; (2) lack CAGG or AAGG sequences and (3) be either about ⅔ purine or about ⅔ pyrimidine. Such suitable oligonucleotides can be readily identified by mere inspection of SEQ ID NO:1 (e.g., with reference to the nucleotide positions in SEQ ID NO:1, SEQ ID NO:$1_{1-20}$, SEQ ID NO:$1_{21-40}$, SEQ ID NO:$1_{51-70}$, SEQ ID NO:$1_{81-100}$, SEQ ID NO:$1_{128-147}$, SEQ ID NO:$1_{131-150}$, SEQ ID NO:$1_{151-170}$, SEQ ID NO:$1_{241-260}$, SEQ ID NO:$1_{288-307}$, SEQ ID NO:$1_{304-323}$, SEQ ID NO:$1_{329-348}$, SEQ ID NO:$1_{334-353}$, SEQ ID NO:$1_{361-380}$, SEQ ID NO:$1_{390-409}$, SEQ ID NO:$1_{421-440}$, SEQ ID NO:$1_{497-516}$, SEQ ID NO:$1_{525-544}$, SEQ ID NO:$1_{541-560}$, etc. comprise some of the suitable target sites within the first 600 nucleotides of SEQ ID NO:1).

In yet another embodiment, the sequences of the SDI molecules can be used to define "antisense oligonucleotides" that can repress the transcription or translation of an SDI gene sequence. In general, an "antisense oligonucleotide" is a nucleic acid (either DNA or RNA) whose sequence is complementary to the sequence of a target mRNA molecule (or its corresponding gene) such that it is capable of binding to, or hybridizing with, the mRNA molecule (or the gene), and thereby impairing (i.e. attenuating or preventing) the, translation of the mRNA molecule into a gene product. To act as an antisense oligonucleotide, the nucleic acid molecule must be, capable of binding to or hybridizing with that portion of target mRNA molecule (or gene) which mediates the translation of the target mRNA. Thus, antisense molecules of the present invention are capable of binding to an SDI nucleic acid molecule and inhibiting its activity. Antisense oligonucleotides are disclosed in European Patent Application Publication Nos. 263,740; 335,451; and 329, 882, and in PCT Publication No. WO90/00624, all of which references are incorporated herein by reference.

The present invention is particularly concerned with those antisense oligonucleotides, especially fragments of the SDI-1, SDI-2, or SDI-3 genes, which are capable of binding to or hybridizing with mRNA or cDNA molecules that encode an SDI gene product. Thus, in one embodiment of this invention, an antisense oligonucleotide that is designed[] to specifically block translation of an SDI mRNA transcript can be used to de-repress the inhibition of DNA synthesis in a recipient quiescent cell.

One manner in which an anti-SDI antisense oligonucleotide may achieve these goals is by having a sequence complementary to that of the translation initiation region of an SDI mRNA and of sufficient length to be able to hybridize to the mRNA transcript of an SDI gene. The size of such an oligomer can be any length that is effective for this purpose. Preferably, the antisense oligonucleotide will be about 10–30 nucleotides in length, most preferably, about 15–24 nucleotides in length.

Alternatively, one may use antisense oligonucleotides that are of a length that is too short to be capable of stably hybridizing to an SDI mRNA under physiologic, in vivo conditions. Such an oligonucleotide may be from about 6–10, or more nucleotides in length. To be used in accordance with the present invention, such an oligonucleotide is preferably modified to permit it to bind to a locus of the translation region of an SDI-encoding mRNA. Examples of such modified molecules include oligonucleotides bound to an antibody (or antibody fragment), or other ligand (such as a divalent crosslinking agent (such as, for example, trimethylpsoralin, 8-methoxypsoralin, etc.) capable of binding to a single-stranded SDI mRNA molecules.

In yet another embodiment, SDI-1 antisense molecules may be designed such that they hybridize to, and stabilize, an unstable segment of the SDI-1 mRNA. Such molecules would thus enhance the transcription and translation of SDI-1 in a cell, and lead to an increased ability to inhibit DNA replication. Such molecules may be used to treat cancer, and other diseases or conditions characterized by hyperproliferation.

An anti-SDI antisense oligonucleotide bound to one reactive group of a divalent crosslinking agent (such as psoralin (for example, trimethylpsoralin, or 8-methoxypsoralin) adduct would be capable of crosslinking to an SDI mRNA upon activation with 350–420 nm UV light. Thus, by regulating the intensity of such light (as by varying the wattage: of the UV lamp, by increasing the distance between the cells and the lamp, etc.) one may control the extent of binding between the antisense oligonucleotide and an SDI mRNA of a cell. This, in turn, permits one to control the degree of attenuation of SDI gene expression in a recipient cell.

In general, the antisense oligomer is prepared in accordance with the nucleotide sequence of an SDI gene, and most preferably in accordance with the nucleotide sequence of SDI-1 provided in FIGS. 5A–5D. The sequence of the antisense oligonucleotide may contain one or more insertions, substitutions, or deletions of one or more nucleotides provided that the resulting oligonucleotide is capable of binding to or hybridizing with the above-described translation locus of either an SDI mRNA, cDNA or an SDI gene itself.

Any means known in the art to synthesize the antisense or triplex oligonucleotides of the present invention may be used (Zamechik et al., *Proc. Natl. Acad. Sci. (U.S.A.)* 83:4143 (1986); Goodchild et al., *Proc. Natl. Acad. Sci. (U.S.A.)* 85:5507 (1988); Wickstrom et al., *Proc. Natl. Acad. Sci. (U.S.A.)* 85:1028; Holt, J. T. et al., *Molec. Cell. Biol.* 8:963 (1988); Gerwirtz, A. M. et al., *Science* 242:1303 (1988); Anfossi, G., et al., *Proc. Natl. Acad. Sci. (U.S.A.)* 86:3379 (1989); Becker, D., et al., *EMBO J.* 8:3679 (1989); all of which references are incorporated herein by reference). Automated nucleic acid synthesizers may be employed for this purpose. In addition, desired nucleotides of any sequence can be obtained from any commercial supplier of such custom molecules.

Most preferably, the antisense or triplex oligonucleotides of the present invention may be prepared using solid phase "phosphoramidite synthesis." The synthesis is performed with the growing nucleotide chain attached to a solid support derivatized with the nucleotide which will be the 3'-hydroxyl end of the oligonucleotide. The method involves the cyclical synthesis of DNA using monomer units whose 5'-hydroxyl group is blocked (preferably with a 5'-DMT (dimethoxytrityl) group), and whose amino groups are blocked with either a benzoyl group (for the amino groups of cytosine and adenosine) or an isobutyryl group (to protect guanosine). Methods for producing such derivatives are well known in the art.

In yet another embodiment, ribozymes can be employed as inhibitors of SDI-mediated inhibition. Ribozymes (RNA enzymes) are catalytic RNA sequences (containing no protein) that can cleave RNA target molecules with which they hybridize (Cech, T. et al., *Cell* 27: 487 (1981); Cech, T., *Science* 236: 1532–1539 (1987); Cech, T. et al., *Ann. Rev. Biochem.* 55: 599–630 (1986); James, W., *Antivir. Chem. Chemother.* 2: 191–214 (1991)). Often the substrate is part of the ribozyme itself.

An artificial ribozyme can be designed to specifically cleave a target RNA by flanking sequences complementary to the target (Haseloff, J. et al., *Nature* 334: 585–591 (1988); Cameron, F. et al., *Proc. Natl. Acad. Sci. USA* 86: 9139–9143 (1989); James, W., *Antiviral Chemistry & Chemotherapy* 2: 191–214 (1991). The minimum requirement for cleavage within the target RNA is the location of a suitable three base sequence GUC, GUA, or GUU preceding the cleavage site. Artificial ribozymes having a characteristic "hammerhead" secondary structure have been designed by Haseloff, J. et al (*Nature* 334: 585–591 (1988); Jeffries, A. et al., *Nucleic Acids Res.* 17: 1371–1377 (1989); Gerlach et al. WO Patent Application WO89/05852 (1989); Goodchild, J. et al., *Arch. Biochem. Biophys.* 284: 386–391 (1991); James, W., *Antivir. Chem. Chemother.* 2: 191–214 (1991)).

E. Protagonists of the SDI Molecules

The present invention thus also pertains to protagonists of the SDI molecules. As used herein, a "protagonist" of an SDI molecule is a molecule that enhances or increases the biological activity of an SDI molecule.

Since p53 is an inducer of SDI expression, it, or a nucleic acid encoding p53, or biologically active fragments of either, may be provided to cells in conjunction with an SDI molecule in order to obtain increased SDI expression.

The present invention also provides SDI protagonists other than the naturally occurring tumor suppressor proteins. Such protagonists may comprise SDI analogs or may comprise non-analog molecules that interact with the cellular molecules that interact with SDI molecules. Thus, mutant forms of the p53 protein having enhanced SDI-activating capacity comprise one illustrative SDI protagonist. Such molecules may be produced by mutating the p53 gene, and then selecting muteins that effect more rapid or more extensive induction of SDI-1 activity than the normal p53 protein.

Similarly, SDI protagonists can be identified through the use of screening assays in which, for example, a candidate molecule is provided to a recipient cell along with an SDI molecule, and the capacity of the candidate molecule to enhance SDI expression is monitored. The above-described methods of rational mimetic design can be used to define SDI protagonists.

F. Antibodies to SDI Molecules

One aspect of the present invention concerns antibodies to SDI proteins and protein fragments and the diagnostic and therapeutic uses of such antibodies.

The above-described SDI proteins and protein fragments may be used to elicit the production of antibodies, single-chain antigen binding molecules, or other proteins capable of binding an SDI epitope. Such antibodies may be polyclonal or monoclonal, and may comprise intact immunoglobulins, of antigen binding portions of immunoglobulins (such as (F(ab'), F(ab')$_2$) fragments, or single-chain immunoglobulins producible, for example, via recombinant means.

Murine monoclonal antibodies are particularly preferred. BALB/c mice are preferred for this purpose, however, equivalent strains may also be used. The animals are preferably immunized with approximately 25 μg of affinity purified SDI protein (or fragment thereof) that has been emmusified a suitable adjuvant (such as TiterMax adjuvant (Vaxcel, Norcross, Ga.)). Immunization is preferably conducted at two intramuscular sites, one intraperitoneal site, and one subcutaneous site at the base of the tail. An additional i.v. injection of approximately 25 μg of antigen is preferably given in normal saline three weeks later. After approximately 11 days following the second injection, the mice may be bled and the blood screened for the presence of anti-SDI antibodies. Preferably, a direct binding ELISA is employed for this purpose.

Most preferably, the mouse having the highest antibody titer is given a third i.v. injection of approximately 25 μg of SDI protein or fragment. The splenic leukocytes from this animal may be recovered 3 days later, and are then permitted to fuse, most preferably, using polyethylene glycol, with cells of a suitable myeloma cell line (such as, for example, the P3X63Ag8.653 myeloma cell line). Hybridoma cells are selected by culturing the cells under "HAT" (hypoxanthine-aminopterin-thymine) selection for about one week. The resulting clones may then be screened for their capacity to produce monoclonal antibodies ("mAbs") to SDI protein, preferably by direct ELISA.

In one embodiment, anti-SDI-1 monoclonal antibodies are isolated using the above-described SDI-1 fusions as immunogens and to facilitate screening. Thus, for example, a group of mice can be immunized using the GST-SDI-1 fusion protein emulsified in Freund's complete adjuvant (approximately 50 µg of antigen per immunization). At three week intervals, an identical amount of antigen is emulsified in Freund's incomplete adjuvant and used to immunize the animals. Ten days following the third immunization, serum samples are taken and evaluated for the presence of antibody. If antibody titers are two low, a fourth booster can be employed. Polysera capable of binding SDI-1 at 1:5,000 dilution can be obtained using this method.

In a preferred procedure for obtaining monoclonal antibodies, the spleens of the above-described immunized mice are removed, disrupted and immune splenocytes are isolated over a ficoll gradient. The isolated splenocytes are fused, using polyethylene glycol with Balb/c-derived HGPRT (hypoxanthine guanine phosphoribosyl transferase) deficient P3x63xAg8.653 plasmacytoma cells. The fused cells are plated into 96 well microtiter plates and screened for hybridoma fusion cells by their capacity to grow in culture medium supplemented with hypothanthine, aminopterin and thymidine for approximately 2–3 weeks. On average, out of every $10^6$ spleen cells subjected to fusion yields a viable hybridoma. A typical spleen yields 5–10×$10^7$ spleen cells.

Hybridoma cells that arise from such incubation are preferably screened for their capacity to produce an immunoglobulin that binds to SDI-1. An indirect ELISA may be used for this purpose. In brief, the supernatants of hybridomas are incubated in microtiter wells that contain immobilized GST-SDI-1. After washing, the titer of bound immunoglobulin is determined using a goat anti-mouse antibody conjugated to horseradish peroxidase. After additional washing, the amount of immobilized enzyme is determined (for example through the use of a chromogenic substrate). Such screening is performed as quickly as possible after the identification of the hybridoma in order to ensure that a desired clone is not overgrown by non-secreting neighbors. Desirably, the fusion plates are screened several times since the rates of hybridoma growth vary. In a preferred sub-embodiment, a different antigenic form of SDI-1 may be used to screen the hybridoma. Thus, for example, the splenocytes may be immunized with the GST-SDI-1 fusion, but the resulting hybridomas can be screened using a $[His]_6$ fusion, such as that having the leader sequence of SEQ ID NO:4.

As discussed below, such antibody molecules or their fragments may be used for either diagnostic or therapeutic purposes. Where the antibodies are intended for diagnostic purposes, it may be desirable to derivatize them, for example with a ligand group (such as biotin) or a detectable marker group (such as fluorescent group, a radioisotope or an enzyme).

Where the antibodies or their fragments are intended for therapeutic purposes, it may desirable to "humanize" them in order to attenuate any immune reaction. Humanized antibodies may be produced, for example by replacing an immunogenic portion of an antibody with a corresponding, but non-immunogenic portion (i.e. chimeric antibodies) (Robinson, R. R. et al., PCT Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al., Science 240:1041–1043 (1988); Liu, A. Y. et al., Proc. Natl. Acad. Sci. USA 84:3439–3443 (1987); Liu, A. Y. et al., J. Immunol. 139:3521–3526 (1987); Sun, L. K. et al., Proc. Natl. Acad. Sci. USA 84:214–218 (1987); Nishimura, Y. et al., Canc. Res. 47:999–1005 (1987); Wood, C. R. et al., Nature 314:446–449 (1985)); Shaw et al., J. Natl. Cancer Inst. 80:1553–1559 (1988); all of which references are incorporated herein by reference). General reviews of "humanized" chimeric antibodies are provided by Morrison, S. L. (Science, 229:1202–1207 (1985)) and by Oi, V. T. et al., BioTechniques 4:214 (1986); which references are incorporated herein by reference).

In one therapeutic embodiment, chimeric bivalent antibodies are employed which contain two different Fab regions, such that the antibody is capable of binding to an SDI epitope (via the first such Fab region) and to a "non-SDI epitope" (i.e. an epitope of a protein other than an SDI protein) (via the second such Fab region). In one embodiment, such "non-SDI epitopes" are selected such that the chimeric molecule can bind to cellular receptors, such as hormone receptors, immune response receptors, etc. Particularly preferred non-SDI receptors include cellular antigens that are indicative of neoplasia, such as antigens associated with leukemia (Seon et al., Proc. Natl. Acad. Sci., USA 80:845 (1983); Aota et al., Cancer Res. 43:1093 (1983); Royston et al., Transplan. Proc. 13:761 (1981)); colon cancer (Koprowski et al., U.S. Pat. No. 4,349,528; Sakamoto et al., European Patent Publication No. 119556; Herlyn et al., Proc. Natl. Acad. Sci., USA 76(3):1438 (1979); Magnani et al., Science 212:55 (1981)); lung cancer (Cuttitta et al., Proc. Natl. Acad. Sci., USA 78:4591 (1981)); breast cancer (Colcher et al., Proc. Natl. Acad. Sci., USA 78:3199 (1981); Schlom et al., Proc. Natl. Acad. Sci., USA 77:6841 (1980)) and other cancers (See, Lloyd, "Human Tumor Antigens: Detection and Characterization with Monoclonal Antibodies," In: Herberman, ed., Basic and Clinical Tumor Immunology I:159–214, Nijoff, Boston (1983).

G. Cellular Receptors of SDI Molecules

One aspect of the present invention concerns cellular receptors of SDI molecules, and in particular cellular receptors of SDI-1, for facilitating the delivery of SDI into target cells.

In one embodiment, such delivery can be accomplished by expressing the SDI molecule as a fusion with a lymphokine, hormone, prohormone, or other molecule that possesses a cellular receptor or a cell-surface ligand that is capable of binding a receptor. Most preferably, this is accomplished by ligating a polynucleotide that encodes an SDI molecule (such as SDI-1 cDNA) to a polynucleotide that encodes the protein which is to recognized and bound by the receptor or cell-surface ligand, and then expressing the desired fusion protein via recombinant means. The fusion protein need not contain the complete sequence of the receptor binding molecule, but may contain only an amount of protein sufficient to permit the desired binding.

In one sub-embodiment, the receptor-binding molecule is selected such that the relevant receptor is present on all or most cells. Examples of such molecules include most peptide hormones (such as growth hormone, insulin, etc.) which bind to their respective receptors, transferrin which binds to the transferrin receptor, Apo-B protein which binds to the low density lipoprotein (LDL) receptor, etc. Alternatively, the SDI fusion protein may be selected such that molecule is capable of being adsorbed by only certain tissue-types or subtypes. Such specificity may be obtained through the use of molecules that are bound to receptors or ligands that are present only on certain populations of cells (such as liver cells, leukocytes, endothelial cells, etc.). Examples of such molecules include proteins such as glucagon, gastrin, certain pituitary hormones (TSH, FSH, etc.), erythropoietin, interleukins, granulocyte-macrophage colony-stimulating factor, neurotrophic proteins, etc. Additionally, proteins capable of binding to cell-surface proteins such as CD4, ICAM-1, selecting, ELAMS, LFA-1, etc. may be used.

For example, since ICAM-1 (Simmons, D. et al., *Nature* 331:624–627 (1988); Staunton, D. E. et al., *Cell* 52:925–933 (1988); Staunton, D. E. et al., *Cell* 61243–254 (1990) is an endothelial cell-surface ligand for leukocytes that express a CD18/CD11 heterodimer (such as LFA-1, etc.) an ICAM-1-SDI fusion molecule would target hematopoietic cells such as lymphocytes. Similarly, a CD4-SDI-1 fusion would be targeted to CD4+ T cells, and could be used to deliver SDI to such T cells. An LFA-1-SDI-1 fusion would target endothelial cells and certain other cell types. A glucagon-SDI fusion could be used to target liver cells, etc.

In another embodiment, the SDI molecule can be conjugated to a non-protein that can undergo specific binding with a cellular receptor. Examples of such molecules include epinephrine, norepinephrine or histamine derivatives, prostaglandins, etc.

In yet another embodiment, an endogenous cellular receptor that is capable of binding an SDI molecule may be expolited to facilitate the delivery of SDI into a target cell. Such a receptor molecules can be obtained using the above-described SDI proteins and protein fragments. In one method for obtaining the SDI receptor, a DNA (or more preferably, a cDNA) library is produced, preferably from cells that express SDI protein. The cDNA fragments are cloned into an expression plasmid which is then introduced into immortalized or tumor cells. The cells are then incubated in the presence of labeled SDI-1, and evaluated for clones that adsorb the SDI-1 to the cell surface, and that exhibit a renewed quiescent or senescent state. Plasmids that encode cellular receptors are then recovered from such clones.

SDI receptor proteins can also be obtained by expressing cDNA clones in bacteria or other hosts, and then determining whether such clones produce proteins that are capable of binding SDI-1. In one preferred sub-embodiment, the cDNA is incorporated into a phage display vector (Lowman, H. B. et al., *Biochem.* 30:10832–10838 (1991); Markland, W. et al., *Gene* 109:13–19 (1991); Roberts, B. L. et al., *Proc. Natl. Acad. Sci. (U.S.A.)* 89:2429–2433 (1992); Smith, G. P., *Science* 228:1315–1317 (1985); Smith, R. P. et al., *Science* 248:1126–1128 (1990), all herein incorporated by reference)). As indicated above, this method involves expressing a fusion protein in which the desired protein ligand is fused to the C-terminus of a viral coat protein (such as the M13 Gene III coat protein, or a lambda coat protein). The phage vectors are then grown to form a library of phage that possess different fusion proteins. The library is then incubated in the presence of immobilized SDI-1 fusion protein having a glutathione S-transferase glutathione binding sequence as its amino terminus. Phage that display cellular receptors of SDI-1 are retained by the immobilized SDI-1 fusion protein, and can be recovered by washing the column with glutathione.

In an alternate method of obtaining the SDI receptor, a cellular extract is obtained and incubated in the presence of SDI-1, especially an SDI-1 fusion protein having a glutathione S-transferase glutathione binding sequence as its amino terminus. Proteins that bind to SDI-1 comprise cellular receptor protein.

When desired, the receptor molecule can be solubilized to form a soluble (i.e. not membrane bound) receptor molecule by truncating the protein domains responsible for anchoring the receptor to the cellular membrane.

IV. Uses of the SDI Molecules of the Present Invention and their Inhibitors

A. Induction of Senescense or Quiescence

Molecules capable of inhibiting SDI function, when provided to a recipient cell cause the immortalization of the cell, and thereby permit the establishment of a permanent cell line. The antisense, ribozyme and other SDI inhibitor molecules of the present invention may thus be used to immortalize valuable cell types (such as primary tissue culture cells, etc.) which would otherwise have a transient period of proliferative viability. They may thus be used for research or to permit or facilitate the accumulation of large numbers of cells, as for organ or tissue grafts or transplants. In one embodiment, therefore, the agents of the present invention may be used in conjunction with methods for organ or tissue culture to facilitate such methods. Such molecules may alternatively be used to effect the immortalization of immunoglobulin producing cells, or cells that produce important biologicals, such as hormones (insulin, growth hormone, IGF, etc.), immune system modifiers (such as interferons, adhesion molecules, lymphokines, etc.).

Such inhibitory nucleic acid molecules will preferably have nucleotide sequences that are complementary to the sequences of the SDI molecules, and most preferably will be complementary to the sequence of regions or all of the SDI-1 gene. When such oligo-nucleotides are provided to recipient cells, the immortalization of the cell line occurs. Alternatively, the antibodies of the present invention may be used to inhibit SDI activity (e.g., to prevent SDI in a fluid (such as blood) from mediating the quiescence of cells that are in contact with the fluid).

B. Diagnostic Uses

A major use of the molecules of the present invention lies in their capacity to diagnose the presence and predisposition to cancer. Since the absence of SDI-1 expression is the mechanism through which p53-dependent cancers mediate tumorigenicity, assays of cellular SDI-1 expression can be used to diagnose the presence and severity of human cancers. For example, the Li-Fraumeni Syndrome is associated with a particular set of mutations in exon 7 of the p53 gene (Malkin, D. et al., *Science* 250:1233–1238 (1990), herein incorporated by reference). Cells of Li-Fraumeni patients do not produce detectable SDI-1 mRNA or SDI-1 protein. Thus, a diagnosis of this disease may be made using hybridization assays, or immunoprecipitation protocols that measure SDI-1 mRNA or protein levels.

As indicated, approximately 50% of human tumors fail to express normal p53 protein. Thus, assays for p53 activity in biopsy samples is can be used to assess the presence of tumors. Such assays can be readily accomplished using the SDI molecules of the present invention, especially the SDI-1 gene sequences, and their fragments. Since p53 is an inducer of SDI expression, the detection of SDI-1 molecules or mRNA in a biopsy material is suggestive of the normal expression of the p53 gene.

The anti-SDI antibodies of the present invention may be used in an immunoassay to assess the presence of SDI in a cell, tissue or fluid. Any of a wide array of immunoassays formats may be used for this purpose (Fackrell, *J. Clin. Immunoassay* 8:213–219 (1985)), Yolken, R. H., *Rev. Infect. Dis.* 4:35 (1982); Collins, W. P., In: *Alternative Immunoassays*, John Wiley & Sons, NY (1985); Ngo, T. T. et al., In: *Enzyme Mediated Immunoassay*, Plenum Press, NY (1985)). The capacity to detect and/or measure SDI presence provides a highly desirable means for assessing the presence or severity of a tumor. Thus, for example, the absence of SDI in a particular tumor indicates that the tumor is more susceptible to metastasis than an SDI-expressing tumor. In one embodiment, the antibodies of the present invention are employed to measure the solubilized SDI molecules of a sample. The methods of the present, invention may, however, be used in situ to permit the detection and analysis of SDI present within a biopsied sample.

The simplest immunoassay involves merely incubating an antibody that is capable of binding to a predetermined target molecule with a sample suspected to contain the target molecule. The presence of the target molecule is determined by the presence, and proportional to the concentration, of any antibody bound to the target molecule. In order to facilitate the separation of target-bound antibody from the unbound antibody initially present, a solid phase is typically employed. Thus, for example the sample can be passively bound to a solid support, and, after incubation with the antibody, the support can be washed to remove any unbound antibody.

In more sophisticated immunoassays, the concentration of the target molecule is determined by binding the antibody to a support, and then permitting the support to be in contact with a sample suspected of containing the target molecule. Target molecules that have become bound to the immobilized antibody can be detected in any of a variety of ways. For example, the support can be incubated in the presence of a labeled, second antibody that is capable of binding to a second epitope of the target molecule. Immobilization of the labeled antibody on the support thus requires the presence of the target, and, is proportional to the concentration of the target in the sample. In an alternative assay, the target is incubated with the sample and with a known amount of labeled target. The presence of target molecule in the sample competes with the labeled target molecules for antibody binding sites. Thus, the amount of labeled target molecules that are able to bind the antibody is inversely proportional to the concentration of target molecule in the sample.

In general, immunoassay formats employ either radioactive labels ("RIAs") or enzyme labels ("ELISAs"). RIAs have the advantages of simplicity, sensitivity, and ease of use. Radioactive labels are of relatively small atomic dimension, and do not normally affect reaction kinetics. Such assays suffer, however, from the disadvantages that, due to radioisotopic decay, the reagents have a short shelf-life, require special handling and disposal, and entail the use of complex and expensive analytical equipment. RIAs are described in *Laboratory Techniques and Biochemistry in Molecular Biology*, by Work, T. S., et al., North Holland Publishing Company, NY (1978), with particular reference to the chapter entitled "An Introduction to Radioimmune Assay and Related Techniques" by Chard, T., incorporated by reference herein.

ELISAs have the advantage that they can be conducted using inexpensive equipment, and with a myriad of different enzymes, such that a large number of detection strategies—calorimetric, pH, gas evolution, etc.—can be used to quantitate the assay. In addition, the enzyme reagents have relatively long shelf-lives, and lack the risk of radiation contamination that attends to RIA use. ELISAs are described in *ELISA and Other Solid Phase Immunoassays* (Kemeny, D. M. et al., Eds.), John Wiley & Sons, NY (1988), incorporated by reference herein.

C. Therapeutic Uses

The molecules of the present invention also posess theraputic utility. A use is said to be therapeutic if it alters a physiologic condition. A non-therapeutic use is one which alters the appearance of a user. The agents of the present invention may be used topically or systemically for a therapeutic or non-therapeutic purpose, such as, for example, to counter the effects of aging, for example on skin tone, color, texture, etc., or on the degeneration of cells, tissue or organs, such as lymphocytes, vascular tissue (such as arteries, arterioles, capillaries, veins, etc.), liver, kidney, heart and other muscle, bone, spleen, etc. The agents of the present invention may be employed to rejuvenate such cells, tissue or organs. Thus, they may be used in pharmaceuticals, and the like, which may comprise, for example, an antisense oligonucleotide, or its equivalent, and a lipophilic carrier or adjunct, preferably dissolved in an appropriate solvent. Such a solvent may be, for example, a water-ethanol mixture (containing 10% to 30% v/v or more ethanol. Such preparations may contain 000.1% to 1.0% of the antisense oligonucleotide. Suitable carriers, adjuncts and solvents are below.

1. Treatment of Cancer and Other Diseases

SDI nucleic acid molecules, their fragments, encoded proteins and polypeptides, and analogs have use in inducing a senescent or quiescent state in a recipient cell. Such induction is desirable in the treatment of age-related disorders (Martin, G. M., *Genome* 31:390 (1989); Roe, D. A., *Clin. Geriatr. Med.* 6:319 (1990); Mooradian, A. D., *J. Amer. Geriat. Soc.* 36:831 (1988); Alpert, J. S., *Amer. J. Cardiol.* 65:23j (1990)); Alzheimer's disease (Terry, R. D., *Monogr. Pathol.* 32:41 (1990); Costall, B. et al., *Pharmacopsychiatry* 23:85 (1990)); asthenia and cachexia (Verdery, R. B., *Geriatrics* 45:26 (1990)), or diseases or conditions in which rapid cellular proliferation is undesirable. In this respect, the agents of the present invention can be used therapeutically to suppress the rapid proliferation of tumor or tumorigenic cells. Thus, in particular, the molecules of the present invention may be used in the treatment of cancer, particularly liver, pancreatic, kidney, lung, stomach, breast, uterine, colon, skin, gliomal, lymphatic, prostate, hepatobiliary cancer and malignant melanoma. Indeed, as discussed below, SDI-1 has broad activity in suppressing the proliferation of tumor cells, such as breast, lung, hepatic and glioma tumor lines. Remarkably, the SDI molecules of the invention have the ability to mediate the differentiation of cancer cells (especially malignant melanoma cells) into non-cancerous cells.

In one embodiment,, such treatment is accomplished by providing SDI-1 protein or protein fragments to tumor cells. Such protein may be provided directly, since SDI-1 appears to be capable of directly entering tumor cells. Alternatively, SDI-1 may be provided in liposomes,: viral sheaths, or other vehicles. In a second embodiment, gene sequences that encode SDI-1 or fragments of SDI-1 may be provided as a gene therapy for cancer.

In the case of melanoma or other skin cancers, the SDI molecules of the present invention may be provided topically, in an emollient, etc. (preferably formulated with a UV-adsorbing compound, such as p-aminobenzoic acid (PABA).

The SDI molecules of the present invention, particularly when formulated in a liposomal drug delivery vehicle, can be used to treat bladder cancer. Additional cancer applications for the SDI molecules of the invention include the inhibition of endothelial cell replication (antiangiogenesis) to prevent neovascularization of tumors, and targeted gene delivery via tumor specific molecules to halt cell growth or induce apoptosis.

The SDI molecules of the present invention may be used alone, or in combination with other conventional chemotherapeutic agents to decrease the effective concentrations that would otherwise be required in order to achieve a therapeutic effect.

Indeed, the SDI-1 protein and nucleic acid molecules of the present invention have significant utility when used as an adjunct to conventional chemotherapeutic agents. In one embodiment, the SDI-1 molecules are administered to tumor cells, thereby enhancing the efficacy of the chemotherapeutic agents. In an alternate or complementary embodiment, the SDI-1 molecules are provided (or additionally provided) sub-sytemically (e.g., locally, or to specific organs or tissue, or regionally) in order to insulate non-tumor cells from the cytotoxic effects of the chemotherapeutic agents.

The premise of chemotherapy is that cancer cells grow more rapidly than normal cells, and hence are more sensitive to cytotoxic agents than normal cells. Each administration of a chemotherapeutic agent kills a percentage of the existing tumor cells, such that multiple administrations are generally needed in order to completely eliminate a tumor (Tenenbaum, L., In: "Cancer Chemotherapy and Biotherapy A Reference Guide," W. B. Saunders Company, Philadelphia, pp. 3–13 (1994)).

As indicated above, in one embodiment, the SDI-1 molecules of the present invention may be used to increase the sensitivity of cancer cells to chemotherapeutic agents, and thus permit the elimination of a tumor using lower doses and/or fewer doses of the chemotherapeutic agent/ Such increased sensitivity can be obtained, for example, by providing a SDI-1 protein (or nucleic acid molecules that express SDI-1) to a patient in concert with the administration of the chemotheraputic agent. Such administration serves to inhibit the replication of the cancer cells (the replication of normal, cells is also inhibited by the SDI-1 molecules, however, such inhibition is largely immaterial since normal cells proliferate far more slowly than cancer cells). After the SDI-1 molcules are provided to the patient, such administration is terminated or diminished. The effect of such transient or diminishing administration is to synchonize the cancer cells to the same stage in the cell cycle (i.e. to freeze the cells, for example, in the $G_1$ phase of the cell cycle). Such synchonization significantly increases the sensitivity of the cancer cells to chemotherapeutic agents.

Because such synchronization provides a means for mazimizing the percentage of cells that are in a particular phase of the cell cycle at the time of the administration, the administration of SDI-1 molecules enhances the clinical efficacy of chemotherapeutic agents that exert their effect during a specific phase or set of phases of the cell cycle. For example, mitotic inhibitors such as vinca alkaloids (e.g., vincristine, vinblastine, vindesine, etc.), podophyllum derivatives (e.g., etoposide, teniposide, etc.), taxoids (e.g., taxol, docetaxel, etc.) act during the M phase of the cell cycle by interfering with the formation of the mitotic spindle. Because only a fraction of tumor cells are in M phase at any given time, such drugs must generally be provided in repeated administrations rather than in a single large dose. By treating the cells with SDI-1 molecules, it is possible to synchronize the tumor cells, such that all (or a large fraction) of the cells will be at M phase at the same time. Hence, such SDI-1 administration permits one to employ mitotic inhibitors more effectively.

In a similar manner, antimetbolites such as the tolate antagonists (e.g., methotrexate, etc.), purine analogs (e.g., cladribine, fludarabine phosphate, pentostatin, etc.), purine antagonists (e.g., 6-mertcaptopurine, 6-thioguanine, etc.) and pyrimidine antagonists (e.g., 5-fluorouracil, 5-fluorodeoxyuridine, cytarabine, etc.) act on cells in S phase. The efficacy of these agents may be enhanced through the adjunct use of SDI-1 molecules.

Such adjunct administration may also be used to improve the selectivity or efficacy of cell cycle phase non-specific chemotherapeutic agents (such as antitumor antibiotics, hydroxyurea, procarbazine, hormones or hormone antagonists, etc.) Despite the observed non-specificity of such agents relative to the cell cycle phase of tumor cells, it is highly probable that synchronization of tumor cell phase will increase the effectiveness of the chemotherapy.

In accordance with the second embodiment, the SDI-1 molecules of the present invention may be used sub-systemically to prevent or to attenuate damage to normal cells. For example, one side effect of conventional cancer chemotherapy is the damage to rapidly growing tissue such as the hair follicles. This damage results in hair loss (alopecia) to affected patients. Despite the transience of such loss, it exacerbates the pyschological trauma, discomfort and depression associated with cancer chemotherapy. Such hair loss is thus of significant clinical interest.

The SDI-1 protein or nucleic acid molecules of the present invention may be used to attenuate or prevent damage or death of hair follicles, and thus provide a treatment for hair loss incident to chemotherapy or age. In this embodiment, the SDI-1 molecules would be locally applied (e.g., topically, transdermally, or intradermally to the scalp, etc.), and preferably via liposomes. Such administration will inhibit follicular growth, and arrest the cells, for example, at G1. The administration will thus desensitize the hair follicules to damage caused by a subsequent administration of a conventional chemotherapeutic agent.

The capcity to deliver SDI-1 to hair follicles provides a means for treating microbial (i.e., fungal, bacterial, or viral) infections of the skin which result from the colonization and infection of the tissue and cells that surround the hair follicles. Examples of such conditions include folliculitis (e.g., boils, carbuncles, etc.), impetigo, fascitis, etc. In particular, SDI-1 (especially when provided in liposomes) can be used to treat acne. Acne results from the colonization and infection of hair follicles by microorganisms such as *Proprionobacterium acne*, staphylococci, micrococci, and pityrosporum yeasts. The symptoms of acne arise from and are exacerbated by the production of sebum by actively, proliferating sebaceous cells of the follicles. The administration of SDI-1 would be convert such actively proliferating sebaceous cells of the follicle to a quiescent state, and thereby attenuate the production of sebum.

The SDI molecules of the present invention may also be used to treat mucositis (mouth ulcers) that arise as an unavoidable side-effect of chemotherapy.

The necessity of providing prompt chemotherapy to pregnant cancer patients jeopardizes their developing fetuses, and hence present medical practice must carefully weigh the benefits of early cancer treatment with the potential harm that such treatment might cause to the fetus. The SDI-1 protein or nucleic acid molecules of the present invention may be used to attenuate or prevent damage to developing fetuses in pregnant women who must undergo chemotherapy during their pregnancy. The SDI-1 protein may be locally provided via injection or infusion into the fetal bloodstream, or into the amnionic fluid which bathes the fetus. Preferably, such local administration is conducted prior to or simultaneously with the administration of a chemotherapeutic agent to the mother. The administration of the SDI-1 molecules insulates the fetus from the cytotoxic effects of the chemotherapy.

A large number of non-cancer diseases can also be treated with the SDI molecules of the present invention. The SDI molecules may be used to treat the skin disorder, psoriasis. Particularly when administered topically to treat psoriasis, the use of the SDI molecules of the present invention can limit the hyperproliferative growth of cells involved in psoriasis with minimal cytotoxic side effects. Rheumatoid arthritis, a debilitating autoimmune disease, may also be treated with the SDI-1 molecules of the invention, The SDI molecules of the invention may be used to mediate or accelerate wound healing of both acute wounds (e.g., lacerations, punctures, surgery, etc.) or chronic wounds (e.g., diabetic ulcers, venous ulcers, decubitus pressure ulcers).

The molecules of the present invention may be used to treat restenosis incident to angioplasty. The term "stenosis" denotes a narrowing or constriction of a duct or canal. A variety of disease processes, such as atherosclerotic lesions, immunological reactions, congenital deformities, etc., can lead to the stenosis of coronary arteries and thus to myocardial ischemia. Percutaneous transluminal coronary angioplasty (PTCA), the insertion and partial inflation of a balloon catheter into a stenotic vessel to effect its repair, has been extensively used to treat stenosis. The major limitation of PTCA is "restenosis" (i.e. the re-constriction) of the vascular lesion (Liu, M. W. et al., *Circulation* 79:1374–1386 (1989), herein incorporated by reference). Restenosis has been found to occur in 30% to 40% of angioplasty patients within 6 months of the procedure (Califf, R. M. et al., *J. Amer Col. Cardiol.* 17:2B–13B (1991), McBride, W. et al., *N. Engl. J. Med.* 318:1734–1737 (1988)). Restenosis develops so rapidly that it may be considered a form of accelerated atherosclerosis induced by injury. The significance of the high restenosis rate is compounded by the present inability to predict with a high degree of certainty which patients, vessels, or lesions will undergo restenosis. Indeed, arteries that are widely patent 2 days after PTCA, free of obstructive thrombus, have exhibited restenosis at catheterization 4–6 months later (Liu, M. W. et al., *Circulation* 79:1374–1386 (1989)).

Glaucomas can also be treated with the SDI molecules of the present invention. "Glaucomas" are a family of debilitating eye diseases that are each characterized by a progressive loss of visual field (i.e. the solid angle of vision that defines whether an object is within view). Unless checked, the impairment of the visual field leads to absolute and irreversible blindness.

Glaucomas are characterized by a disruption in the normal flow of the "aqueous" (i.e., the clear fluid of the eye having a composition similar to that of plasma) through the posterior and anterior chambers of the eye (Vaughan, D. et al., In: *General Ophthamology*, Appleton & Lange, Norwalk, Conn., pp. 213–230 (1992)). The aqueous is produced by the ciliary processes and secreted into the posterior ocular chamber. In normal eyes, it then passes through the pupil and into the anterior chamber of the eye. The aqueous flows out of the anterior chamber into a collagen-elastin filtering structure known as the "trabecular meshwork," and ultimately through the "canal of Schlemm" into the venous blood supply. The,, ability of aqueous to traverse the canal of Schlemm depends upon the presence and extent of transcellular channels and the rate of outflow determines the intra-ocular pressure. The average pressure in normal eyes is about 14 mm Hg. In glaucoma, the outflow of aqueous is disrupted, and intra-ocular pressure increases. Damage usually begins at about 30 mm Hg, and the eye ruptures at about 240 times average pressure values.

The antimitotic agent, 5-fluorouracil, has been proposed as a therapeutic for glaucoma (Sarfarazi, F., U.S. Pat. No. 5,304,561). Unfortunately, 5-fluorouracil is associated with significant adverse side effects. Since the agents of the present invention can prevent cellular proliferation, they may be used to inhibit the proliferation of the cells of the trabecular meshwork, and accordingly provide a therapy for glaucoma, especially, primary open angle glaucoma. For such uses, it is desirable to employ SDI-1 molecules that can be administered by intra-ocular means (such as by eye drops, or ointments). The ability of a drug to traverse the cornea is enhanced if the drug has both lipophilic and hydrophilic regions. Thus, for intra-ocular delivery, it is desirable to modify the SDI-1 molecules of the invention such that they contain such regions. Suitable lipophilic and hydrophilic groups are known in the art (see, Remington's Pharmaceutical Sciences), and comprise aliphatic groups, lipids, etc. (lipophilic groups) and organic acids, esters, ionic groups, etc. (hydrophilic groups). Such groups can be readily added to the SDI-1 molecules of the present invention by, for example, derivatizing the side chain groups of appropriate amino acids.

Cysteinyl residues may be reacted with α-haloacetates (and corresponding amines), such as chloroacetic acid or chloroacet-amide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues may be derivatized by reaction with diethylprocarbonate at pH 5.5–7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues may be reacted with succinic or other carboxylic acid anhydrides. Derivatization with these agents has the effect of reversing the charge of the lysinyl residues. Other suitable reagents for derivatizing a-amino-containing residues include imidoesters such as methyl picolinimidate; pyridoxal phosphate; pyridoxal; chloroborohydride; trinitrobenzenesulfonic acid; O-methylissurea; 2,4 pentanedione; and transaminase-catalyzed reaction with glyoxylate.

Arginyl residues may be modified by reaction with one or at several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

Carboxyl side groups (aspartyl or glutamyl) may be selectively modified by reaction with carbodiimides (R'-N-C-N-R') such as 1-cyclohexyl-3-(2-morpholinyl-(4-ethyl) carbodiimide or 1-ethyl-3(4 azonia 4,4-dimethylpentyl) carbodiimide. Furthermore, aspartyl and glutamyl residues may be converted to asparaginyl and glutaminyl residues by reaction with ammonium ions.

2. Antiviral and Antimicrobial Uses

In an alternative embodiment, the molecules of the present invention may by used as an anti-viral agent to impair the propagation of visurses such as influenza, hepatitis, (e.g., hepatitis B or hepatitis C), Epstein-Barr, rhinovirus, pappilomavirus, papovavirus, etc. In particular, since SDI molecules (especially, SDI-1 and its analogs) act to inhibit cellular proliferation, and since retroviruses preferentially proliferate only in actively dividing cells, the present invention provides an antiviral therapy against HIV, and thus can be used to treat diseases such as AIDS and ARC. Similarly, for conditions such as warts (including venereal warts), larygeal pappilomatosis, progressive multifocal leucoencephalopathy, etc., the administration of such SDI molecules inhibits the proliferation of infected cells, and thus provides symptomatic treatment for the condition.

In another embodiment, the molecules of the present invention may be used as an anti-parasitic agent to treat fungal, yeast, protozoan, helminthic, nematodal and other parasitic infections (e.g., candidiasis, aspergillosis, coccidiomycosis, leishmaniasis, amoebiasis, trichomoniasis, tinea (pedis, crusis, etc.) vaginal monolysis, schistosomiasis and malaria).

In a manner similar to that described above, the administration of SDI-1 molecules can increase the therapeutic efficacy of antiviral or antimicrobial agents. Because SDI-1 molecules inhibit the replication of pathogens, it may be applied topically to skin, or systemically via injection, in order to prevent or attenuate the risk of subsequent infection. Thus, for example, the molecules could be incorporated into a suitable pharmaceutical composition, and applied topically to the hands of surgeons or other medical practitioners prior to their exposure to potentially infected individuals.

In another embodiment, the SDI-1 molecules could be administered as an adjunct to antiviral agents in the treatment of suspected or actual viral infection in order to synchronize the cell cycles of any virally infected cells, and thereby enhance the therapeutic efficacy of the antiviral agent. Likewise, the SDI-1 molecules could be administered as an adjunct to antiparasitic agents in the treatment of suspected or actual parasitic infection in order to synchronize the cell cycles of the cells of the parasite, and thereby enhance the therapeutic efficacy of the antiparasitic agent. Such adjunct administration may be used to treat conditions such as the above-described fungal, yeast, protozoan, helminthic, nematodal or other parasitic infections.

3. Other Therapeutic Uses

The antisense and other SDI inhibitor molecules of the present invention may be used to stimulate the proliferation of spermatocytes, or the maturation of oocytes in humans or animals, and thus, may be used to increase the fertility of a recipient. Conversely, SDI molecules and their analogs can be used to inhibit gametogenesis in males or females, and thus can be used as contraceptive agents to induce infertility in males or females. Such use also provides the benefit of attenuating the replication and proliferation of virally (e.g., HIV, etc.) infected cells, and hence serves to lessen the probability of contracting viral diseases (e.g., AIDS, etc.).

Since the SDI-1 molecules of the present invention are capable of inhibiting DNA replication, they may be used to prevent or attenuate UV-light induced DNA damage (such as that encountered from overexposure to the sun). In individuals who lack normal capacity to repair such damage, the SDI-1 -mediated inhibition of DNA synthesis would provide greater opportunity for repair to occur. Hence, the SDI-1 molecules of the present invention may be used to treat indivduals suffering from deficiencies in DNA repair capacity (e.g., indivduals having xeroderma pigmentosum, ataxia telangiectasia, etc.).

Since the antisense and other inhibitor molecules of the present invention are capable of stimulating cellular proliferation, they may be used to promote wound healing, angiogenesis, endothelial cell proliferation, recovery from burns, or after surgery, or to restore atrophied tissue, etc. The antibodies of the present invention may also be used to effect wound healing, bum recovery, or subsequent to trauma or surgery. Indeed, all such compounds can also be used to suppress general tissue regeneration or vascularization. For such an embodiment, these agents may be formulated with antibiotics, anti-fungal agents, or the like, for topical or systemic administration.

The molecules of the present invention may be used to provide gene therapy for recipient patients. In one embodiment, cells or tissue from a patient may be removed from the patient and treated with a molecule of the present invention under conditions sufficient to permit a restoration of an active growing state. In one preferred embodiment of this use, lymphocytes of an individual (such as, for example, an immune compromised individual, such as an AIDS patient, etc., or an immune-competent individual who will serve as a donor of lymphocytes) can be removed and treated with antisense SDI nucleic acids. The administration of these molecules will derepress the lymphocytes. After administration, the lymphocytes are reintroduced into the patient, and have an enhanced ability to combat infection.

In yet another embodiment of the present invention, the molecules of the present invention can be used to facilitate autologous cell replacement. In this embodiment, the SDI nucleic acid molecules, their fragments, encoded proteins and polypeptides, and analogs can be used to permit the in vitro proliferation of cells (such as bone marrow cells, epithelial cells, muscle cells, hepatic cells, etc.) in order to replenish or augment the amount or concentration of such cells in a patient. Thus, for example, bone marrow cells can be removed, treated with such molecules, and then cultured in vitro until a sufficient mass of cells has been obtained to augment a desired immune response. Alternatively, hepatic cells (such as hepatic cells that are free of a hepatitis virus) can be removed from a patient, treated, cultured and then transplanted back into the patient in order to treat hepatic disease.

In one sub-embodiment, such treated cells may be themselves directly transplanted back into the patient, and thus propagate in vivo. Alternatively, as indicated, such cells may be cultured in vitro, and reintroduced when a desired titer has been attained.

In accordance with the above-described embodiments and sub-embodiments of gene therapy, the SDI-1 cDNA and antisense sequences may be operably linked to tumor-specific or tissue-specific promoters in order to confine the therapeutic effect to a desired site or tissue. Examples of suitable tumor-specific promoters include those that direct the transcription of tumor specific antigens such as α-fetoprotein, carcinoembryonic antigen, amylase, γ-glutamyl transferase, etc. Examples of suitable tissue-specific promoters include the phenylalanine hydroxylase promoter (Wang, Y. et al., *J. Biol. Chem.* 269:9137–9146 (1994); Svensson, E. et al., *Eur. J. Hum. Genet.* 1:306–313 (1993); Konencki, D. S. et al., *Biochemistry* 31:8363–8368 (1992)), the alpha-1-antitrypsin (AAT) promoter (Li, Y. et al., *Molec. Cell. Biol.* 8:4362–4369 (1988); the muscle actin promoter, etc. Of particular interest are promoters that direct expression in breast, liver, lung or colon tissues.

The molecules of the present invention are particularly suitable for use in the creation and/or study of animal models for disease or tissue degeneration. Thus, the molecules of the present invention can be used to study effectors of an animal model that is characterized by abnormal aging or cellular degeneration. Similarly, the administration of the SDI molecules (linked, for example to suitable regulatory sequences in order to permit their expression in a recipient cell) can be used to create animal models of aging or of tissue degeneration.

D. Delivery of Pharmacological Agents

The capacity of SDI-1 to directly enter a cell provides a means for accomplishing the delivery of pharmacological agents to a recipient cell. Thus, in one embodiment, a pharmacological agent will be conjugated to SDI-1 and provided to a recipient patient. The presence of the SDI-1 moiety (which may be the intact SDI-1 protein, or a transport-sufficient fragment of SDI-1) transports the attached pharmacological agent into the recipient cell.

Any of a variety of cross-linking agents may be used to conjugate the pharmacological agent to the SDI-1 moiety. Alternatively, such agents can be provided as fusion proteins (exemplified by the above-discussed GST-SDI-1 fusion proteins). Such fusion proteins can be prepared by, for example, expressing a nucleic acid molecule that encodes such a fusion.

The pharmacological agents that may be administered to cells in this manner may include agents that provide a therapeutic benefit to cells (such as an antihypertensive, anti-inflammatory, anti-arrthymic, etc.). Alternatively, the pharmacological agent may adversely affect recipient cells (such as by comprising a cytokine, a toxin, etc.).

Where it is desired that the pharmacological agents to be delivered is SDI-1, such can be accomplished using the anti-SDI antibodies of the present invention may comprise chimeric binding regions. By selecting the binding portions of such chimeric antibodies to include a binding domain that is specific for a tumor antigen, it is possible to produce an antibody that can bind to both a tumor antigen and to an SDI molecule. Such a molecule can be used to "ferry" an SDI protein into any cell that arrays the tumor antigen. The conveyed SDI molecule can induce the tumor cell to resume a quiescent or senescent state. Such chimeric antibodies thus comprise an anti-cancer treatment.

Alternatively, the SDI molecules of the present invention may be provided to cells by fusing the SDI molecule to a hormone, or other molecule that can bind to a desired subset of recipient cells. Thus, for example by conjugating SDI-1 to a soluble CD4 molecule, or to an insulin molecule, one coud target the administration of SDI-1 to leukocytes that array CD4, or to cells that array the insulin receptor. Although such conjugates can be produced using a variety of methods, it is preferred to produce such conjugates by expressing nucleic acid molecules that encode the fusion proteins.

As indicated, a GST-SDI fusion is a particularly preferred fusion. The N-terminal domain of rat GST exhibits significant homology to human migration inhibition factor (MIF) (David, J. R., *Parisitology Today* 9:315316 (1993); Mikayama, T. et al., *Proc. Natl. Acad. Sci.* (*U.S.A.*) 90:10056–10060 (1993), herein incorporated by reference). Thus, distinct from any action of SDI, GST thus has the potential for binding to cellular receptor that are capable of binding MIF and related molecules. Indeed, one aspect of the present invention involves the recognition that a GST-pharmacological agent fusion protein can bind to cellular receptors and effect the delivery of the pharmacological agent to the target cell. Thus, molecules other than SDI could be fused to GST sequences (such as those described above) in order to effect their delivery into a desired target cell.

E. Preparatory Uses

The anti-SDI antibodies of the present invention provide a facile means for purifying and recovering SDI protein from solution. In this embodiment, cellular lysates or extracts are incubated in the presence of an anti-SDI antibody, preferably immobilized to a solid support. The SDI molecules bind to the antibody, and can thus be recovered in purified form.

F. Uses of the SDI Cellular Receptor and Its Solubilized Derivatives

The SDI cellular receptor and its solubilized derivatives can be used to facilitate the recovery of SDI from SDI protein-containing preparations. In this manner, the receptor may be used as a pseudo-antibody. The receptor may also be used therapeutically to modulate cellular expression and responses to SDI protein. Thus, receptor molecules can be provided to tumor cells (via liposomes, or by providing such cells with nucleic acid that encodes the receptor). Such molecules will increase the capacity of the tumor cells to respond to SDI presence, and will thereby ameliorate the cancer.

V. Methods of Administration

The SDI molecules of the present invention can be formulated according to known methods to prepare pharmaceutically useful compositions, whereby these materials, or their functional derivatives, having the desired degree of purity are combined in admixture with a physiologically acceptable carrier, excipient, or stabilizer. Such materials are non-toxic to recipients at the dosages and concentrations employed. The "SDI molecule" of such compositions may be SDI-1 protein, fusions (e.g., GST-fusions, etc.) or fragments of SDI-1 protein or mimetics of such molecules. The SDI molecules may be sense, antisense or triplex oligonucleotides of the SDI-1 cDNA or gene. A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

In some instances, the presence of an intervening sequence upstream of a protein-encoding nucleic acid sequence can enhance the transcription or expression of specified polynucleotides (Brihster, R. L. et al., *Proc. Natl. Acad. Sci.* (*U.S.A.*) 85:836–840 (1988); Palmiter, R. D. et al., *Proc. Natl. Acad. Sci.* (*U.S.A.*) 88:478–482 (1991); Huang, M. T. F. et al., *Nucl. Acids Res.* 18:937–947 (1990); GRuss et al., *Proc. Natl. Acad Sci.* (*U.S.A.*) 76:4317 (1979); Hamer, D. et al., *Cell* 18:1299 :(1979); Gasser, et al., *Proc. Natl. Acad. Sci.* (*U.S.A.*) 79:6522 (1982); Calles, et al., *Genes & Devel.* 1:1183 (1987)). Where the SDI molecules that are to be administered comprise nucleic, acid molecules, such as SDI-1-encoding molecules or SDI-1 antisense sequences, it is particularly preferred to employ nucleic acid molecule that include at least one non-translated intervening sequence within, or adjacent to the relevant SDI sequence. Such use is particularly desirable in transfections of cells in culture, when producing transgenic animals, or when mediating genetic therapy. Since expression is obtained in the absence of such intervening sequences, the relative position or number of intervening sequences is not critical to the invention. The presence of such a non-translated intervening sequence can, however, increase the extent of transcription and/or expression of SDI nucleic acid molecules. A preferred construct contains the SDI sequences adjacent to, but not interrupted by, the intervening sequences. An example of a suitable vector is pOPRSVICAT (Stratagene), which contains Rous Sarcoma Virus LTR (long terminal repeat) promoter that is operably linked (i.e., capable of transcribing) nucleic acid sequences that encode a chloramphenicol acetyl transferase (CAT). An intervening untranslated sequence from SV40 is present between the promoter and the CAT-encoding gene sequences.

Suitable vehicles and their formulation, inclusive of other human proteins, e.g., human serum albumin, are described, for example, in Remington's Pharmaceutical Sciences (16th ed., Osol, A., Ed., Mack, Easton Pa. (1980)). In order to form a pharmaceutically acceptable composition suitable for storage or administration, such compositions will contain an effective amount of one or more "SDI molecule."

If the composition is to be water soluble, it may be formulated in a buffer such as phosphate or other organic acid salt preferably at a pH of about 7 to 8. If the composition is only partially soluble in water, it may be prepared as a microemulsion by formulating it with a nonionic surfactant such as Tween, Pluronics, or PEG, e.g., Tween 80, in an amount of, for example, 0.04–0.05% (w/v), to increase its solubility. The term "water soluble" as applied to the polysaccharides and polyethylene glycols is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

Optionally other ingredients may be added such as antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic, acid, or arginine; monosaccharides, disaccharides, and other carbohydrates including cellulose or its derivatives, glucose, mannose, or dextrins; chelating agents such as EDTA; and sugar alcohols such as mannitol or sorbitol.

Additional pharmaceutical methods may be employed to control the duration of action. Controlled or sustained release preparations may be achieved., through the use of polymers to complex or absorb the SDI molecule(s) of the composition. The controlled delivery may be exercised by selecting appropriate macromolecules (for example polyesters, polyamino acids, polyvinyl pyrrolidone, ethylenevinylacetate, methylcellulose, carboxymethylcellulose, or protamine, sulfate) and the concentration of macromolecules as well as the methods of incorporation in order to control release.

Sustained release formulations may also be prepared, and include the formation of microcapsular particles and implantable articles. For preparing sustained-release compositions, the SDI molecule(s) of the composition is preferably incorporated into a biodegradable matrix or microcapsule. A suitable material for this purpose is a polylactide, although other polymers of poly-(α-hydroxycarboxylic acids), such as poly-D-(-)-3-hydroxybutyric acid (EP 133,988A), can be used. Other biodegradable polymers include poly(lactones), poly(orthoesters), polyamino acids, hydro-gels, or poly(orthocarbonates) poly(acetals). The polymeric material may also comprise polyesters, poly(lactic acid) or ethylene vinylacetate copolymers. For examples of sustained release compositions, see U.S. Pat. No. 3,773,919, EP 58,481A, U.S. Pat. No. 3,887,699, EP 158,277A, Canadian Patent No. 1176565, U. Sidman et al., "Biopolymers" 22:547 [1983], and R. Langer et al, "Chem. Tech." 12:98 [1982].

Alternatively, instead of incorporating the SDI molecule(s) of the composition into polymeric particles, it is possible to entrap these materials in microcapsules prepared, for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

Liposomes are a particularly preferred means for accomplishing the delivery of SDI (protein or nucleic acid or other) molecules. Such a delivery means is particularly preferred when administering SDI molecules to skin as by topical administration. Although a wide variety of liposome compositions can be employed, a preferred liposome composition is composed of a mixture of positively charged and neutral lipids, such as those disclosed by Eppstein, D. A. et al. (U.S. Pat. No. 4,897,355), herein incorporated by reference. An alternative preferred liposome composition is described by Yarosh, D. B. (U.S. Pat. No. 5,190,762, herein incorporated by reference), and in particular the pH-sensitive liposomes discussed therein. Such sensitivity causes the liposomes to destabilize at a pH of less 4.5 Such sensitivity is produced by using phospholipids (such as phosphatidylethanolamine) which form lipid bilayers when charged, but fail to stack in an ordered fashion when neutralized. The net charge of such phospholipids can be maintained at a pH which would otherwise neutralize the phospholipid's head groups by including charged molecules in the lipid bilayer which themselves can become neutralized. Examples of suitable charged molecules include oleic acid and cholesteryl hemisuccinate (CHEMS) (U.S. Pat. No. 5,190,762).

A particularly preferred liposome formulation contains a 3:1 (w/w) mixture of the polycationic lipid 2,3-dioleyloxy-N-[2(sperminecarboxamido)ethyl]-N,N-dimethyl-1-propanaminium-trifluoroacetate (DOSPA) [Chemical Abstracts designation: N-[2-({2,5-bis(3-aminopropyl)amino-1-oxypentyl}amino)ethyl]-N-,N-dimethyl-2,3-bis(9-octadecenyloxy)-1-propanaminium-trifluoro-acetate, and the neutral lipid dioleolyphosphatidylethanolamine (DOPE) in water. A particularly preferred liposome having such a composition is Lipofectamine™ Reagent (Life Technologies, Inc., Gaithersburg, Md.). The positively charged and neutral lipids form liposomes that can complex with either acidic protein or nucleic acids (see, Lin, M. F. et al., *Biochem. Biophys. Res. Commun.* 192:413–419 (1993); Wizel, B. et al., *Eur. J. Immunol.* 24:1487–1495 (1994)). The capacity of such liposomes to deliver a basic protein such as SDI-1 (predicted pI=8.4) is quite unexpected.

"Transferosomes" are also preferred liposomes for the purposes of the present invention. Methods for producing and using transferosomes are provided by Planas, M. E. et al. (*Anesth. Analg.* 75:615–621 (1992)), Cevc, G. et al. (*Biochim Biophys. Acta* 1104:226–232 (1992)), Blume, et al. (*Biochim Biophys. Acta* 1146:157–168 (1993)), Blume, et al. (*Biochim Biophys. Acta* 1149:180–184 (1993)), all herein incorporated by reference.

Another preferred liposome composition is provided by Weiner, N. D. (PCT Application WO 91/01719), Egbaria, K. et al. (*Antimicrob. Agents Chemother.* 33:1217–1221 (1989)), Egbaria, K. et al. (*Antimicrob. Agents Chemother.* 34:107–110 (1990)), all herein incorporated by reference.

Additionally preferred liposome formulations are disclosed by Handjani, R. M. et al. (U.S. Pat. No. 4,830,857), Hope, M. J. et al. (U.S. Pat. Nos. 5,204,112; 5,252,263), and by Vanlerberghe, G., et al. (U.S. Pat. Nos. 5,164,488; 4,827,003; 5,008,406; 4,247,411), all herein incorporated by reference.

In one embodiment, particularly performed using the above-described preferred liposome compositions, preformed liposomes are incubated with SDI protein molecules. Without limitation to the invention, the protein is believed to unexpectedly adsorb to (or dissolve into) the external surface of the liposome, and to thus become arrayed on or in the liposome surface. The protein may traverse the surface of the liposome.

The liposome formulations can be administered to cells in culture (so as to achieve immortalization, or to induce the cessation of proliferation), or, therapeutically, to treat disease or hyper- or hypo-proliferative conditions.

In one embodiment, such formulations will contain an SDI-1 molecule (e.g., a GST-SDI-1 fusion, etc.) that can mediate its own intracellular uptake. Suitable methods are known in the art, see, for example, for example, by Biessen, E. A. L. et al. (PCT Application WO94/04545), Felgner, P. L. (PCT Patent Application WO91/17424), Akiyama, K. et al. (PCT Application WO93/20801), Blum, A. et al. (PCT Application WO93/04672), Abai, A. M. et al. (PCT Application WO93103709), Hosokawa, S. et al. (U.S. Pat. No. 5,264,221), Cullis, P. R. et al. (U.S. Pat. Nos. 5,204,112; 5,252,263), Japanese Patent No. 4,082,893, Phillips, W. T. et al. (U.S. Pat. No. 5,158,760), Weiner, N. D. (PCT Application WO91/01719), Hostetler, K. Y. et al. (U.S. Pat. No. 5,223263), Kobayashi, Y. et al. (European Patent 335597); Weiner, A. L. et al. (PCT Application WO89/05151); Hope, M. J. et al. (PCT Application WO87107530), all herein incorporated by reference.

In a second embodiment, liposome formulations and methods that permit intracellular uptake of the SDI-1 molecule will be employed. Suitable methods are known in the art, see, for example, Chicz, R. M. et al. (PCT Application WO 94/04557), Jaysena, S. D. et al. (PCT Application WO93/12234), Yarosh, D. B. (U.S. Pat. No. 5,190,762), Callahan, M. V. et al. (U.S. Pat. No. 5,270,052) and Gonzalezro, R. J. (PCT Application 91/05771), all herein incorporated by reference.

The SDI pharmaceutical compositions used for therapeutic administration may be sterilized, as by filtration through sterile filtration membranes (e.g., 0.2 micron membranes). The compositions may be stored in lyophilized form or as a liquid solution. It will be understood that use of certain of the foregoing excipients, carriers, or stabilizers will result in the formation of salts of the SDI molecules.

The compositions of the present invention can be applied topically as to the skin, or to gastrointestinal, vaginal, oral, etc. mucosa. When applied topically, the SDI molecule(s) of the composition may be suitably: combined with other ingredients, such as carriers and/or adjuvants. There are no limitations on the nature of such other ingredients, except that they must be pharmaceutically acceptable and efficacious for their intended administration, and cannot degrade the activity of the active ingredients of the composition. Examples of suitable vehicles include ointments, creams, gels, or suspensions, with or without purified collagen. The compositions also may be impregnated into transdermal patches, plasters, and bandages, preferably in liquid or semi-liquid form.

For obtaining a gel formulation, the SDI molecule(s) of the composition formulated in a liquid composition may be mixed with an effective amount of a water-soluble polysaccharide or synthetic polymer such as polyethylene glycol to form a gel of the proper viscosity to be applied topically. The polysaccharide that may be used includes, for example, cellulose derivatives such as etherified cellulose derivatives, including alkyl celluloses, hydroxyalkyl celluloses, and; alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, nontoxic, simple to prepare, and not too runny or viscous, and will not destabilize the SDI molecule(s) held within it. Preferably the polysaccharide is an etherified cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low and high molecular weight polyethylene glycols to obtain the proper viscosity. For example, a mixture of a polyethylene glycol of molecular weight 400–600 with one of molecular weight 1500 would be effective for this purpose when mixed in the proper ratio to obtain a paste.

The compositions of the present invention can also be formulated for administration parenterally by injection, rapid infusion, nasopharyngeal absorption (intranasopharangeally), dermoabsorption, or orally. The compositions may alternatively be administered intramuscularly, or intravenously. Compositions for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers, adjuncts or occlusive dressings can be used to increase tissue permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include wetting agents, emulsifying and suspending agents, or sweetening, flavoring, coloring or perfuming agents.

If methylcellulose is employed in the gel, preferably it comprises about 2–5%, more preferably about 3%, of the gel and the SDI molecule(s) of the composition is present in an amount of about 300–1000 $\mu$g per ml of gel. The dosage to be employed is dependent upon the factors; described above. As a general proposition, the SDI molecule(s) of the composition is formulated and delivered to the target site or tissue at a dosage capable of establishing in the tissue a maximum dose that is efficacious but not unduly toxic.

Generally, the dosage needed to provide an effective amount of the composition will vary depending upon such factors as the recipient's age, condition, sex, and extent of disease, if any, and other variables which can be adjusted by one of ordinary skill in the art.

Effective amounts of the compositions of the invention can vary from 0.01–1,000 mg/ml per dose or application, although lesser or greater amounts can be used.

When SDI-1 nucleic acid molecules are employed (as in antisense or triplex repression), methods of "gene therapy" are employed. The principles of gene therapy are disclosed by Oldham, R. K. (In: *Principles of Biotherapy*, Raven Press, NY, 1987), and similar texts. Disclosures of the methods and uses for gene therapy are provided by Boggs, S. S. (Int. *J. Cell Clon.* 8:80–96 (1990)); Karson, E. M. (*Biol. Reprod.* 42:39–49 (1990)); Ledley, F. D., In: *Biotechnology, A Comprehensive Treatise, volume 7B, Gene Technology*, VCH Publishers, Inc. NY, pp 399–458 (1989)); all of which references are incorporated herein by reference. Such gene therapy can be provided to a recipient in order to treat (i.e. suppress, or attenuate) an existing condition, or to provide a prophylactic gene therapy to individuals who, due to inherited genetic mutations, or somatic cell mutation, carry a predisposition to glaucoma.

Most preferably, viral or retroviral vectors are employed for this purpose. Examples of suitable vectors are discussed by Fletcher, F. A. et al. (*J. Exper. Med.* 174:837–845 (1991)), Mäkelä, T. P. et al (*Gene* 118:293–294 (1992)), Porgador, A. et al (*Canc. Res.* 52:3679–3686 (1992)), Yoshimura, K. et al. (*Nucl. Acids Res.* 20:3233–3240 (1992)), Lim, B. et al. (*Proc. Natl. Acad. Sci.* (*U.S.A.*) 86:8892–8896 (1989)), Ohi, S. et al. (*Gene* 89:279–282 1990)), and Russel, S. J. et al. (*J. Virol.* 66:2821–2828 (1992)).

Having now generally described the invention, the same will be more readily understood through reference to the following examples which are provided by way of illustration, and are not intended to be limiting of the present invention, unless specified.

EXAMPLE 1

Creation of the cDNA Library

A cDNA library was obtained using RNA from normal human neonatal foreskin fibroblasts, such as the cell line HCA2. To do this, the cells were grown in minimal essential medium with either Earle's or Hanks' balanced salt solution supplemented with 10% fetal bovine serum (GIBCO or Hyclone). Cells were cultured, and their in vitro life span was determined, under the conditions disclosed by Smith, J. R., and Braunschweiger, K. I., *J. Cell Physiol.* 98:597–601 (1979), hereby incorporated by reference. Quiescent cells were made by replacing the normal culture medium with culture medium containing 0.5% serum before the cells become confluent. The cells were maintained in low serum culture for up to 3 weeks.

Total cellular RNA was isolated either by the guanidinium thiocyanate/CsCl method (Garger, S. J. et al., *Biochem. Biophys. Res. Commun.* 117:835–842 (1983)) or a guanidinium thiocyanate/phenol method (Chomczynski, P., and Sacchi, N., *Anal. Biochem.* 162:156–159 (1987), RNAzol B, Biotecx Lab. Inc. TX). Poly A+ RNA was isolated by oligo (dT) cellulose column chromatography (Collaborative Res. MA).

10 µg of the poly A+ RNA derived from senescent cells, as described above, was converted to double-stranded cDNAs by using RNase H⁻/MMLV reverse transcriptase according to the instructions of the supplier (BRL, MAD), and blunt-ended by T4 polymerase treatment. The double-stranded cDNA preparations were size fractionated by agarose gel electrophoresis, and the 2–4.5 kb fraction isolated, for insertion into an expression vector.

The expression vector used for this purpose was a 3.4 kb plasmid, designated pcDSRαΔ (FIG. 1). Plasmid pcDSRαΔ is a derivative of the plasmid pcDSRα296, which includes the Okayama-Berg SV40 promoter and the LTR from HTLV-1 (Takebe, Y. et al., *Mol. Cell. Biol.* 8:466–472 (1988); provided by Dr. M. Yoshida (Cancer Inst. of Japan)). Plasmid pcDSRαΔ was formed by removing a 336 base pair (bp) segment of the Pstl-Kpnl fragment of pcDSRα296 and replacing it with 28 bp of a Pstl-Kpnl fragment from pUC19. The resulting plasmid (pcDSRαΔ) was used as a cloning and expression vector.

Plasmid pSV2cat (Gorman, C. et al., *Mol. Cell. Biol.* 2:1044–1051 (1982)) was provided by Dr. Gretchen Darlington (Texas Children's Hospital). The pcD-vector (Okayama, H., and Berg, P., *Mol. Cell. Biol.* 3:280–289 (1983)) was provided by Dr. H. Okayama (Osaka University, Japan); the plasmid has the chloramphenicol acetyltransferase ("CAT") gene inserted between the SV40 promoter and SV40 poly A signal. pcDSRαΔ-cat was constructed from pcDSRαΔ by the insertion of 0.8 Kb of a HindIII-Smal digested SRa promoter fragment into HindIII digested pSVOcat via a two step ligation. A very strong promoter was desired in order to allow for efficient expression screening of the cDNA library. From an analysis of several mammalian expression vectors (pSV2cat, pcD-cat and pcDSRαΔ-cat, transfected into young cells), the SRa promoter was found to drive the expression of the CAT gene at high efficiency in young cycling cells. The relative CAT activities of these plasmids were calculated by normalizing to the amount of protein used for each reaction. The transcriptional efficiency was about 20-fold greater than that of the conventional pSV2 promoter, which utilizes the SV40 early gene promoter.

pCMVβ carries the *E. coli* β-galactosidase gene driven by the human cytomegalovirus immediate early gene promoter (MacGregor, G. R., and Caskey, C. T., *Nucleic Acids Res.* 17:2365 (1989); provided by Dr. Grant MacGregor, Baylor College of Medicine, TX). Plasmid pβ440, which carries 443 bp of the human β-actin sequence (Nakajima-lijima, S. et al., *Proc. Natl. Acad. Sci.* 82:6133–6137 (1985); provided by Dr. Kozo Makino, Osaka University, Japan). Plasmid pHcGAP (Tso, J. Y. et al., *Nucleic Acids Res.* 13:2485–2502 (1985)), which carries a full length human glyceraldehyde 3 phosphate dehydrogenase (GAPDH) cDNA, was obtained from the American Type Culture Collection, Rockville, Md.

For cDNA antisense expression, full length cDNA fragments were excised by BamHI digestion from the originally cloned pcDSRαΔ vector, and re-ligated in the reverse direction.

cDNAs recovered from the agarose gel were directly inserted into a calf intestine alkaline phosphatase treated Smal site of pcDSRαΔ, and transformed into *E. coli* MC1061 or DH-1. Ampicillin resistant colonies were picked randomly and plasmid sizes determined. These procedures were repeated until 2–4.5 kb cDNA insertions were achieved in more than 90 percent of the plasmids tested. Then each *E. coli* colony was picked with toothpicks and 5 colonies combined into one cDNA pool. More than 400 cDNA pools were prepared, grown in 96 well microtiter plates and stored in 14% glycerol at −70° C. For DNA isolation, *E. coli* from each cDNA pool was cultured in 200 ml, and treated by the standard methods of ethydium bromide/CsCl ultracentrifugation (Garger, S. J. et al., *Biochem. Biophys. Res. Commun.* 117:835–842 (1983)) one or two times, followed by dialysis against TE (10 mM Tris pH 8.0, 1 mM EDTA) solution.

EXAMPLE 2

DEAE-Dextran Mediated Transfection and Transient Expression Screening

Young, cycling fibroblast cells were seeded at a density of 0.9–1.2×10⁵ per well in 6 well tissue culture plates or 35 mm tissue culture dishes 18 h prior to transfection. Transfection was done as described by Cullen, B. R., In: *Guide to Molecular Cloning Techniques. Methods in Enzymology.*, S. L. Berger and A. R. Kimmel (ed.) Academic Press, pp. 684–704 (1987); herein incorporated by reference with minor modifications as described below.

For each transfection, 100 ng of pCMVβ and 400 ng of a cDNA pool were mixed and suspended in 190 μl of phosphate buffered saline (PBS) solution and 10 μl of 10 mg/ml of DEAE-dextran (Pharmacia, MW~500,000) was added. 400 ng of the cloning vector plasmid, pcDSRαΔ, was used with pCMVβ as a control. After washing the cells with PBS once, DNA solutions were added and the cells incubated for up to 45 min at 37° C. in a $CO_2$ incubator. Then 2 ml of cell culture medium with serum, containing 64 μM chloroquine (Sigma, MO) was added directly and incubated for another 2.5 h. After the chloroquine treatment, the transfection mixture was removed and the cells treated with 10% dimethyl sulfoxide in cell culture medium with serum for 2 min. Cells were then returned to fresh cell culture medium with serum and incubated to allow for expression of the transfected DNA.

18 h after transfection, 0.5 μCi/ml of $^3$H-thymidine was added and the incubation continued for another 48 h. Cells were fixed by adding 25 μl of 25% of glutaraldehyde solution to the culture medium and incubated for 5 min at room temperature, followed by three washings with PBS. Immediately after washing, cells were treated with the X-gal reaction mixture (1 mM $MgCl_2$, 3 mM $K_4[Fe(CN)_6]$, 3 mM $K_3[Fe(CN)_6]$, 0.1% triton X-100, and 1 mM X-gal dissolved in 0.1 M sodium phosphate buffer (pH 7.5) containing 10 mM KCl) for up to 20 min to allow light-blue staining of the cells. After the X-gal staining, the cells were washed with water, dried and processed for autoradiography using Kodak NTB nuclear track emulsion (Kodak, NY). DNA synthesis activity in X-gal positive cells was then determined. The percent inhibition of DNA synthesis was calculated using the formula:

$$\frac{\begin{bmatrix}\text{\% labeled nuclei in} \\ \text{blue cells in which} \\ \text{control plasmids} \\ \text{were transfected}\end{bmatrix} - \begin{bmatrix}\text{\% labeled nuclei in} \\ \text{blue cells in which} \\ \text{cDNA plasmids} \\ \text{were transfected}\end{bmatrix}}{\begin{bmatrix}\text{\% labeled nuclei in blue cells in which} \\ \text{control plasmids were transfected}\end{bmatrix}} \times 100$$

Candidate cDNA pools were divided into individual cDNAs and screened further for the identification of specific DNA synthesis inhibitory cDNA sequences.

Nuclear microinjection of young cycling cells was performed as described by (Lumpkin, C. K. et al., *Mol. Cell Biol.* 6:2990–2993 (1986), herein incorporated by reference). Briefly, 5,000–10,000 cells were plated onto 22 mm square etched grid coverslips (Belico) in 35 mm tissue culture dishes. Three or four days later, nuclear microinjections were performed on a minimum of 300 cells, using either pCMVβ+cDNA plasmid or pCMVβ+pcDSRαΔ (which served as the control). Plasmids were co-microinjected at a concentration of 50 ng/μl each. 18 hours after microinjection, the cells were labeled with $^3$H-thymidine for 24 h, fixed, stained with X-gal and processed for autoradiography. The percent inhibition of DNA synthesis was calculated as above.

Northern blot analysis was performed using either 5 μg of total RNA or 1 μg poly A+ RNA. The RNA was size fractionated by electrophoresis on formaldehyde-agarose gels and transferred to nylon membranes (ICN; Biotrans, formerly Pall Biodyne A) as described by Maniatis, T. et al., Molecular cloning: A Laboratory Manual; Cold Spring Harbor Laboratory, Cold Spring Harbor, N.Y. (1982), herein incorporated by reference. Radioactive probes were prepared by the random primer method, and blots hybridized as described by Maniatis, T. et al., Molecular cloning: A Laboratory Manual; Cold Spring Harbor Laboratory, Cold Spring Harbor, N.Y. (1982).

The northern blot analyses revealed that the sizes of the cellular transcripts of the SDIs were compatible with the sizes of the SDI cDNAs. This was expected since successful expression screening requires full-length cDNA insertions into the vector.

For rehybridization with β-actin or glyceraldehyde phosphate dehydrogenase (GAPDH) probe, filters were repeatedly stripped of the labelled probes following the manufacturer's instructions. The data were quantitated by an Ambis Radioanalytic Scanning System.

An assay of CAT activity was determined as follows: Young cycling cells were seeded into 35 mm dishes and 500 ng of plasmid transfected as described above. 24 hours after the transfection, the cells were scraped from the dish, and CAT assay performed as described by Gorman (Gorman, C., In: DNA Cloning, A Practical Approach. IRL Press, Oxford, England, pp. 143–164 (1985), herein incorporated by reference).

EXAMPLE 3 cDNA Cloning of the Senescent Cell Derived Inhibitors (SDI) of DNA Synthesis

Double-stranded cDNAs were synthesized from senescent cell derived poly A+ RNA, which has been shown to inhibit DNA synthesis in young cells when microinjected into the cytoplasm (Lumpkin, C. K. et al., *Science* 232:393–395 (1986)). The cDNAs were size fractionated, inserted into pcDSRαΔ The resulting *E. coli* clones were divided into small pools. Plasmids from each pool were co-transfected with the transfection marker plasmid, pCMVβ, which allowed a determination of the labelling index of transfected cells specifically, since even in high efficiency transfection, frequencies varied from experiment to experiment. Transfection frequencies of the marker plasmid ranged from 30–90%. About 200 cDNA pools were screened and four pools remained positive for DNA synthesis inhibitory activity after five repeated transfections. The candidate pools were then divided into individual plasmids and screened further.

Three independent positive plasmid clones were obtained. In the cDNA pool A, only one plasmid, No. 2, exhibited strong DNA synthesis inhibitory activity. Similarly, in pools B and C only one cDNA clone caused inhibition. The size of inserted cDNAs was 2.1 kb, 1.2 kb and 2.7 kb, respectively. These cDNA sequences have been designated as senescent cell derived inhibitors, SDI-1, SDI-2 and SDI-3, respectively.

The nucleotide sequence of the SDI-1 cDNA clone (SEQ ID NO: 1), and the amino acid sequence of SDI-1 (SEQ ID NO: 2) have been determined. The cDNA sequence presented herein for SDI-1 differs from that described in U.S. patent application Ser. No. 07/808,523 now abandoned, in possessing an unrecited G at position 286, and in having the sequence CG rather than GC at position 1843–1844. The presently disclosed sequence was obtained through the re-sequencing of the pcDSRαΔ-SDI-1 plasmid whose isolation and characteristics were described in U.S. patent application Ser. No. 07/808,523 now abandoned E. coli DH5 transformed with the pcDSRαΔ-SDI-1 plasmid was deposited with the American Type Culture Collection, Rockville, Md., USA, on Oct. 1, 1992, and has been accorded accession number ATCC 69081.

A nucleic acid molecule whose sequence coresonds to a portion of the SDI-1 nucleotide sequence reported herein has been identified among the 2375 random gene sequence fragments reported by Adams, M. D. et al. (*Nature* 355:632–634 (1992)).

EXAMPLE 4

Microinjection of SDI Sequences into Young Cycling Cells

In order to verify the functional activity of SDI sequences, microinjections were performed. A plasmid carrying either SDI-1 or SDI-2 was co-microinjected with the marker plasmid into the nuclei of young cycling cells. The labelling index of the resulting blue cells was determined (Table 1). These plasmids showed strong inhibitory activity on DNA synthesis of young cells. For control experiments, the empty vector was co-microinjected with the marker plasmid. This caused slight inhibition when the labelling index was compared with uninjected cells, a phenomenon also observed in transfection experiments. Microinjections with SDI-3 were not performed because the inhibitory activity was lower than SD-1 and SD-2 transfection experiments.

In addition to normal human fibroblasts, the SDI-1 molecules were also found to be capable of inhibiting the synthesis of DNA in several tumor cell types (melanoma, lung carcinoma, and ovarian tumor), and in immortalized SV40-transformed fibroblasts, and CHO cells. SDI-1 molecules were also capable of inhibiting the synthesis of DNA in normal bovine pulmonary artery smooth muscle.

TABLE 1

|  | Plasmids Injected | No. of Cells Injected | No. of Labelled Nuclei per Total Blue Cells* | Labelling Index (%) | % Inhibition |
|---|---|---|---|---|---|
| Exp. 1 | pCMVβ + pcDSRαΔ† | 335 | 58/97 | 59.8 | 0 |
|  | pCMVβ + SDI-1 | 380 | 20/89 | 22.5 | 62.4 |
|  | pCMVβ + SDI-2 | 380 | 6/82 | 7.3 | 87.8 |
| Exp. 2 | pCMVβ + pcDSRαΔ† | 423 | 68/109 | 62.3 | 0 |
|  | pCMVβ + SDI-1 | 465 | 26/98 | 26.5 | 57.5 |
|  | pCMVβ + SDI-2 | 475 | 27/118 | 22.9 | 63.2 |

Notes:
†Control;
*The number of cells expressing detectable levels of β-galactosidase; The concentration of each DNA was 50 μg/ml.

EXAMPLE 5

Antisense DNA Transfection

Figure 3:
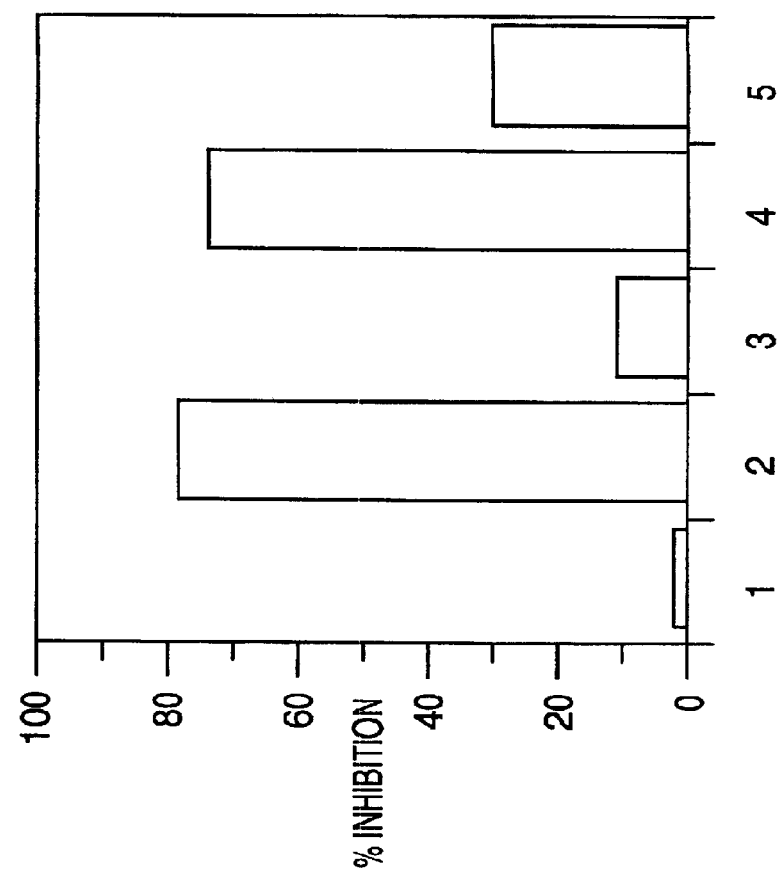
FIG. 3 shows antisense SDI cDNA transfection. Antisense cDNA expression plasmids were made and co-transfected with pCMVβ into young cells. Lane 1: control pcDSRαΔ, lane 2: pcDSRαΔ-SDI-1, lane 3: pcDSRαΔ antiSDI-1, lane 4: pcDSRαΔ-SDI-2, lane 5: pcDSRαΔ-antiSDI-2.

In order to examine whether any inhibitory activities are sequence orientation specific, antisense expression vectors of SDI-1 and SDI-2 sequences were constructed. Since both sequences lacked BamHI sites and since BamHI sites were present at both ends of the cDNA (FIG. 1), the sequences were easily excised and religated in the opposite orientation. Transfection of antisense sequences resulted in no inhibition of DNA synthesis in young cells (FIG. 3). In addition, no enhancement was observed. The results clearly indicate the sequence orientation specificity of the SDI activity, and suggest the presence of specific gene products coded by the cDNA sequences.

Normal human fibroblasts and many other cells cease to synthesize DNA in the absence of appropriate growth factors. Since SDI-1 is a key negative regulator of initiation of DNA synthesis, molecules that are antisense to SDI-1 are able to cause cells to enter S phase. To demonstrate this ability, several normal human cell lines were isolated and provided with SDI-1 antisense molecules (expressed by cloning the SDI-1 cDNA in and antisense orientation into a vector having a metallothionein promoter).

For this purpose, antisense expression vectors were constructed by cloning SDI-1 antisense sequences into PMET, an inducible expression vector containing an altered human metallothionine promoter. The metallothionine promoter in PMET was derived from pM26 and contains a deletion in the basal promoter and the addition of synthetic metal response elements in triplicate (McNeall, J. et al., *Gene* 76:81–88 (1989)). For construction of PMET, adenovirus sequences containing E1A gene 12S and 13S introns (nucleotides 917–1673) were first cloned into the mammalian expression vector PRC/CMV (Invitrogen) at the Not I/Apa I sites of the multiple cloning region of this plasmid to create pRc/CMV-Ad. To ensure that no translation of E1A sequences occurred and to create an Spe I cloning site in this vector, an SpeI linker containing a stop codon was inserted between the CMV promoter and E1A splice sequence in-frame with the E1A sequence. The CMV promoter of plasmid Rc/CMV-Ad was then replaced with the pM26 promoter to create PMET. To accomplish this, the metallothionine promoter was excised from pM26 by BglII digestion and inserted into the BamHI site of pBlueScript (pBS; Stratagene). An EcoRV and NotI fragment containing the promoter was then subcloned from pBS into a filled-in BglII site and NotI site of Rc/CMV-Ad. Antisense sequences from the SDI-1 CDNA were derived from the full-length CDNA cloned into the BamHI site of pBS. The StuI site at nucleotide 127 was converted to an SpeI site by insertion of an SpeI linker to make SDISPE127. An SpeI linker was also inserted at the ApaI site at nucleotide 318 to create SDISPE318. These constructs were digested with SpeI and inserted in antisense orientation into the SpeI cloning site of PMET, thus creating pMET-AS127 and pMET-AS318.

Cell lines expressing SDI-1 antisense were obtained by calcium phosphate transfection using the BES/CaPO$_4$ procedure described by Chen, C. et al., *Molec. Cell. Biol.* 7:2745–2752 (1987)) except that the cells were not replated after transfection. HCA2 cells (3×10$^5$) at PD10 were transfected with 20 μg PMET, pMETAS127 or pMETAS318 DNA. Following two weeks of G418 selection, colonies were picked and expanded. Inducibilty and integrity of the inserted sequence was examined by the addition of 100 μM ZnCl$_2$ and 2 μM CdCl$_2$ followed by RNA analysis. RNA analysis of total cell RNA from stable transformants was performed by RNAse protection using antisense RNA probes internally labeled with [$^{32}$P]-UTP as described by Adami, G. et al., *EMBO J.* 10:3457–3465 (1991)). The probe pMET+SDI-1, containing SDI-1 nucleotides 444–686, was used to measure expression of SDI-1 from both the transfected genes and endogenous mRNA. After EcoNI digestion, transcription from the SP6 promoter in the PMET vector results in a antisense labelled probe that hybridizes to both RNA from the expression expression vector and to endogenous SDI-1 mRNA. This allows a comparison of relative levels of expression from the introduced construct and SDI-1 endogenous RNA. As a control β-actin mRNA was measured in all assays. The actin probe contains nuclotides 2124–2189 inserted between the Eco Ri and the filled-in Bam HI sites of pBS.

When the stably transfected cells were placed in medium containing lowered amounts of growth factors (0.5% fetal bovine serum) for 7–10 days and pulse labelled for 24 hours with tritiated thymidine, fewer than 5% incorporated label. However, when antisense SDI-1 was induced by the addition of $ZnCl_2$ and $CdCl_2$ 24 hours prior to the addition of the tritiated thymidine, more than 25% of the cells were found, by incorporation of label, to have initiated the synthesis of new DNA, and thus to have regained the capacity to proliferate.

This experiment shows that the antisense sequences of the present invention can be used to immortalize cells that would absent such treatment undergo sensecnece.

EXAMPLE 6

Expression of SDI mRNAs During Cellular Senescence

To examine the changes in SDI mRNA expression during cellular senescence, total RNA from young and senescent cells was hybridized to 32P-labelled SDI cDNA probes. The SDI-1 probe hybridized to a 2.1 kb cellular transcript, SDI-2 hybridized to a 1.4 kb transcript, and SDI-3 hybridized to a 2.5 kb transcript (Table 2). Table 2 provides a quantitation of the total RNA northern analysis of expression of SDI genes in young (Y) and senescent (S) cells. 5 µg each of total RNA from young and senescent cells were hybridized with SDI probes. The filters were repeatedly stripped of the radioactive, probe and rehybridized with the probes for the internal controls. The relative amount of SDI mRNA in each sample was normalized by the amount of GAPDH detected on the same filter and by the relative amount of SDI/GAPDH.

TABLE 2

Quantitation of the Northern Analysis

| ATTRIBUTE | SDI-1 | | SDI-2 | | SDI-3 | |
|---|---|---|---|---|---|---|
| | Y | S | Y | S | Y | S |
| Relative Amount of SDI | 1.0 | 3.3 | 1.0 | 0.31 | 1.0 | 0.31 |
| Relative Amount of GAPDH | 1.0 | 0.37 | 1.0 | 0.36 | 1.0 | 0.38 |
| Relative Amount of SDI/GAPDH | 1.0 | 9.3 | 1.0 | 0.86 | 1.0 | 0.82 |

During cellular senescence, the SDI-1 message increased about 3-fold, while SDI-2 and SDI-3 messages decreased 3-fold. The same filters were rehybridized with a β-actin, and then to a GAPDH probe as internal controls. The results demonstrated that expression of both control genes decreased about 3-fold during cellular senescence. In previous studies, a 2–3 fold decrease of β-actin expression during cellular senescence had been observed (Kumazaki, T. et al., *Exp. Cell Res.* 195:13–19 (1991); Seshadri, T., and Campisi, J., *Science* 247:205–209 (1990); Furth, J. J., *J. Gerontol.* 46:B122–124 (1991)). The decreased expression of both β-actin and GAPDH genes in senescent cells led to the use of poly A+ RNA for northern analysis. Poly A+ RNA was isolated from the total cellular RNA preparations used for Table 2, and hybridized to SDI cDNA, followed by probing with β-actin and GAPDH respectively (Table 3). Table 3 discloses the results of a poly A+ RNA Northern analysis of SDI gene expression in young (Y) and senescent (S) cells. 1 µg each of poly A+ RNA from young and senescent cells were used for the analyses. The relative amount of SDI mRNA in each sample was calculated as in Table 2.

TABLE 3

Quantitation of the Northern Analysis

| | ATTRIBUTE | | | | | |
|---|---|---|---|---|---|---|
| | SDI-1 | | SDI-2 | | SDI-3 | |
| | Y | S | Y | S | Y | S |
| Relative Amount of of GAPDH | 1.0 | 0.83 | 1.0 | 0.87 | 1.0 | 0.87 |
| Relative Amount of SDI/GAPDH | 1.0 | 11.4 | 1.0 | 1.0 | 1.0 | 1.0 |

The results clearly indicated that the expression of both β-actin and GAPDH was equal in young and senescent cells when they were compared on the basis of mRNA, consistent with previous observations. When SDI gene expression was compared at the mRNA level, SDI-1 mRNA was increased 11-fold in senescent cells, whereas expression of SDI-2 and SDI-3 remained constant throughout the in vitro lifespan (Table 3). This result suggests that SDI-1 is a senescent cell specific inhibitor of DNA synthesis, whereas SDI-2 and SDI-3 are most likely more general inhibitors involved in cell cycle regulation.

EXAMPLE 7

Changes of Poly A RNA Content During Cellular Senescence

The observation that the results of the total versus poly A+ RNA northern analyses were quantitatively different, indicated that the poly A+ RNA content in total RNA preparations might change during cellular senescence. To test this hypothesis, cells were cultivated serially and total RNA was harvested at different population doubling levels. Poly A+ RNA was isolated from each sample.

Figure 4:
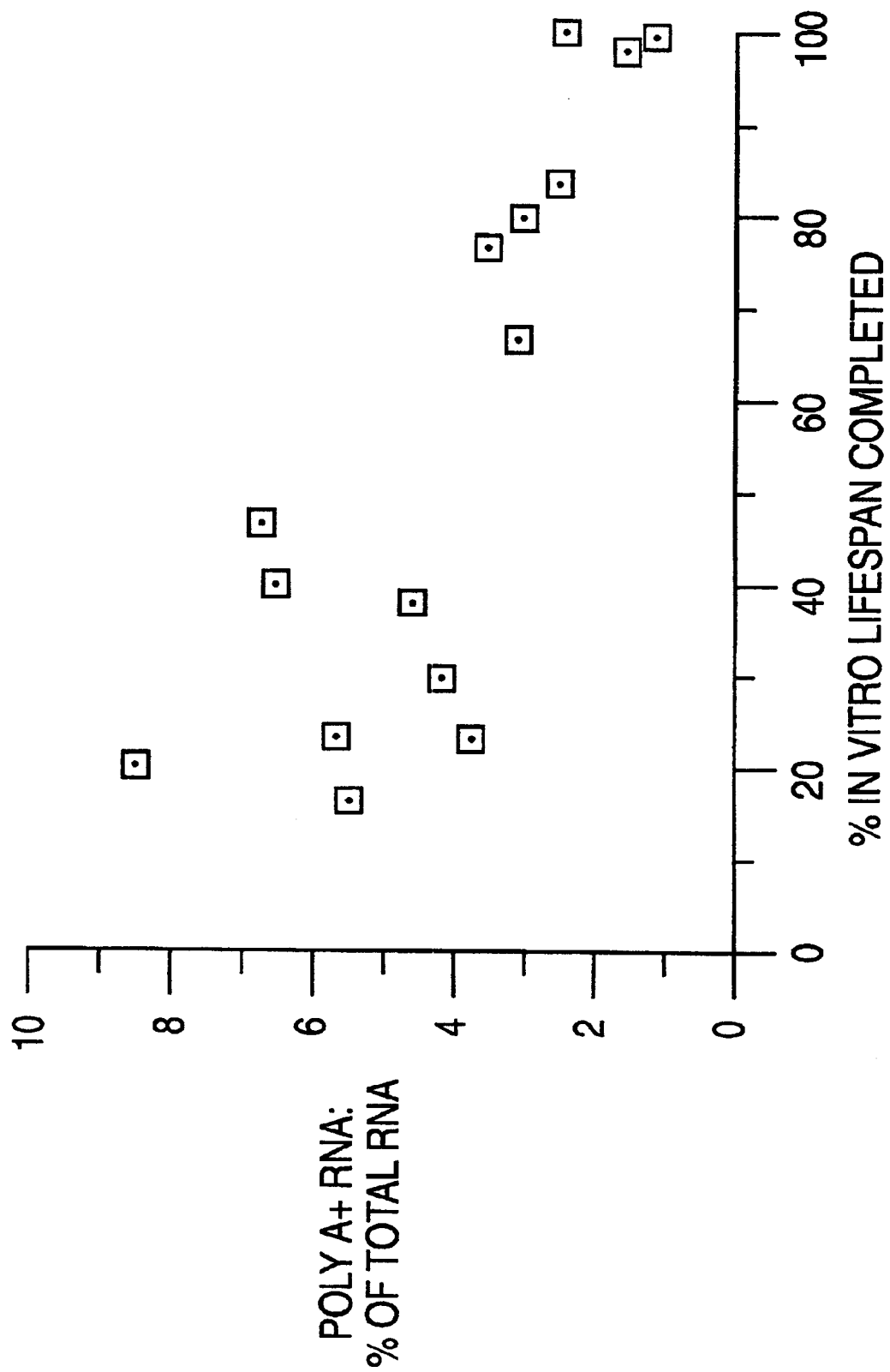
FIG. 4 shows the changes in poly A+ RNA recovery from total RNA during cellular aging.

The result clearly indicated that poly A+ RNA content decreased gradually during cellular senescence (FIG. 4). In FIG. 4, cells were cultivated serially and total RNA was harvested. Poly A+ RNA: % of total RNA was plotted against the culture's age (% in vitro life span completed). Senescent cells had 3–4 fold less poly A+ RNA when compared with very young cells. However, when total RNA content per cell was calculated, senescent cells had 1.3–1.5 fold more than young cells (see, Cristofalo, V. J., and Kritchevsky, D., *Med. Exp.* 19:313–320 (1969)).

In order to determine whether SDI-1 message increased gradually during subcultivation or whether a rapid increase occurred near the end of the in vitro life span, poly A+ RNA from cultures at different population doublings was hybridized with the 32p labelled SDI-1 probe. This analysis revealed that SDI-1 expression increased as the cultures became senescent, with a major change occurring during the final few passages (Table 4). Table 4 shows the accumulation of SDI-1 mRNA during cellular aging process. One microgram each of poly A+ RNA from the cells of different population doublings were hybridized to SDI-1 probe. The relative amount of SDI-1 mRNA in each sample was calculated as in Table 2.

TABLE 4

Quantitation of % Lifespan Completed

| | ATTRIBUTE | | | | | | |
|---|---|---|---|---|---|---|---|
| | 24% | 37% | 46% | 66% | 78% | 88% | 100% |
| Relative Amount of GAPDH | 1.0 | 1.6 | 1.5 | 1.3 | 1.4 | 1.3 | 0.9 |
| Relative Amount of SDI/GAPDH | 1.0 | 2.2 | 2.1 | 4.0 | 3.5 | 6.2 | 20.5 |

Changes in SDI-1 expression during quiescence were also examined. Young, quiescent cells were maintained in 0.5% fetal bovine serum (FBS)-containing medium for up to three weeks. Total RNA was harvested each week and the amount of RNA hybridizing to the SDI-1 probe was analyzed. SDI-1 message increased significantly during cellular quiescence (Table 5). Table 5 shows the accumulation of SDI-1 mRNA during cellular quiescence. 4 μg each of total RNA was obtained from the young cells cultured with 0.5% FBS containing medium for 1, 2, 3 weeks, was hybridized with SDI-1 probe. The relative amount of SDI-1 mRNA was calculated as in Table 2 (C: control culture with 10% FBS medium). When the result was normalized to GAPDH expression, SDI-1 expression was found to have increased 18-fold after two weeks in low serum medium compared to that of a control dividing culture in 10% FBS medium.

TABLE 5

Accumulation of SDI-1 mRNA During Cellular Quiescence

| ATTRIBUTE | C | 1 wk | 2 wk | 3 wk |
|---|---|---|---|---|
| Relative Amount of GAPDH | 1.0 | 0.72 | 0.88 | 0.37 |
| Relative Amount of SDI/GAPDH | 1.0 | 12.2 | 18.4 | 14.9 |

The fact that the cellular representation of mRNA vs total RNA was found to change during cellular senescence is significant. During the in vitro aging process, the content of mRNA was found to decrease gradually (FIG. 4), in spite of, the slight increase of the total RNA per cell. This phenomenon indicates that a gradual decline of the overall gene expressions during the cellular aging process, and explains the decreased expression of β-actin and GAPDH genes in senescent cells when Northern blot analysis was done with total RNA (Table 2). However, the expression levels of these housekeeping genes between young and senescent cells were almost constant when the Northern blot analysis was done with poly A+ RNAs (Table 3). This analysis revealed the strong expression of SDI-1 message in senescent cells, and unchanging expression of SDI-2 and 3 genes throughout the in vitro life span.

EXAMPLE 8

The SDI-1 Gene

The SDI-1 gene codes for a senescent, cell specific inhibitor of DNA synthesis. Increased expression of this gene occurred when the cells entered their final few divisions (Table 4). The expression kinetics correlated well with the phenotypic expression of senescence cells. SDI-1 gene expression was also found to increase after young cells were made quiescent and nondividing by serum deprivation (Table 5). This result demonstrates the involvement of this gene in the inhibition of DNA synthesis of cellular quiescence as well as senescence. Cells made quiescent by deprivation of serum growth factors have been shown to produce an inhibitor of DNA synthesis with characteristics similar to the inhibitor from senescent cells (Pereira-Smith, O. M. et al., *Exp. Cell Res.* 160:297–306 (1985); Stein, G. H., and Atkins, L., *Proc. Natl. Acad. Sci. USA.* 83:9030–9034 (1986)).

The fact that SDI-1 expression increases during both senescence and quiescence indicates that it is an inhibitor of DNA synthesis (Smith, J. R., J. *Gerontol.* 45:B32–35 (1990); herein incorporated by reference). Alternatively, SDI-1 sequences might be related to the growth arrest-specific genes recently cloned from mouse cells (Schneider, C. et al., *Cell* 54:787–793 (1988); Manfioletti, G. et al., *Mol. Cell. Biol.* 10:2924–2930 (1990)).

EXAMPLE 9

The Expression of the SDI-1 Gene Product

SDI-1 cDNA has been expressed in two different bacterial expression systems, has been transcribed in vitro and translated in two different in vitro systems. Two bacterial expression systems were used in order to maximize the probability of obtaining sufficient amounts of SDI-1 protein. In the first expression system, SDI-1 protein was expressed as a glutathione S-transferase fusion protein at yields of 5–10 μg per liter of bacterial culture. The recombinant protein could be cleaved with thrombin and purified in order to give an SDI-1 protein with a few extra amino acids. The GST fusion was formed by cleaving a *Schistosoma japonicum* GST-encoding polynucleotide with BamHI so as to produce a cleavage fragment that contained nucleotides 1–673 of the GST-coding sequence. The free BamHI site at position 673 generated via such treatment was then ligated to the SDI-1 encoding polynucleotide in order to form the GST-SDI-1 gene fusion. The GST-SDI-1 fusion protein was produced via recombinant expression of this gene fusion.

In the second expression system, a 6 histidine amino terminal tag was utilized in order to aid in purification. This recombinant protein may be used without further modification. Both systems permitted the isolation of pure preparations of protein.

In the course of this experiment, in vitro transcription and translation systems were used to confirm the open reading frame deduced from the nucleic acid sequence of the SDI-1 cDNA. The calculated molecular weight of the SDI-1 protein is approximately 16,000 daltons. The in vitro synthesized protein migrates, by SDS PAGE, with a relative mobility of approximately 21,000 daltons. This small difference may be due to a slightly unusual charge or conformation of the SDI-1 protein. A partial amino acid sequence of the bacterially expressed protein verified the open reading frame (SEQ ID NO:2).

The bacterially expressed proteins were used to generate polyclonal antisera and monoclonal antibodies to the intact native protein. Such antibodies may be more effective in immunoprecipitation of SDI-1 protein and SDI-1 protein complexes than the antisera produced from synthetic peptides. Preliminary immunocytochemical studies, using an antisera of highest affinity (antisera #55) which reacted strongly with the fusion protein on a western transfer at a 1:20,000 dilution, suggested that the SDI-1 protein was relatively abundant in senescent cells compared to dividing young cells. In senescent cells the location appears to be perinuclear, whereas in young cells there appears to be a small amount of SDI-1 protein located in the nucleus. In order to obtain specific staining it was necessary to pre-absorb the antisera against a fixed cell monolayer of cells which do not express detectable levels of SDI-1 mRNA (TE85). The cells were fixed with 4% paraformaldehyde followed by methanol.

In order to study the cellular phenotype resulting from the induced expression of SDI-1 mRNA in cells which normally express the gene at low levels and to examine the effect of antisense SDI-1 constructs it is desirable to obtain cell lines in at which the SDI-1 gene is stably integrated under the control of an inducible promoter. Toward this goal, a functional vector containing SDI-1 under the control of the metallothionine promoter was constructed. Following transfection of this construct into young proliferation competent cells and incubation in the presence of 100 $\mu$M zinc chloride and 2 $\mu$M cadmium chloride, initiation of DNA synthesis was inhibited by about 50%. In the absence of metals there was no inhibition of DNA synthesis. The inhibitory activity observed is not due to metal toxicity since cells transfected with the control vector (pcDSR$\alpha$) and grown in the presence of metals were found to have approximately 90% of the DNA synthetic capacity of cells transfected with the same plasmid grown in the absence of metals.

In order to demonstrate that the inhibitory effects observed with SDI-1 were not related to the nature of the specific promoter used to drive expression, the capacity of SDI-1, expressed from other promoters, to inhibit DNA synthesis was investigated. Young proliferating human fibroblasts were therefore co-transfected with CMV-$\beta$-gal and CMV-SDI-1. Transfection of cells with CMV-$\beta$-gal had little effect on DNA synthesis while CMV-SDI-1 was even more effective than SDI-1 in the pcDSR$\alpha$ vector in these particular experiments.

The SV40 large T antigen is capable of inducing senescent cells to synthesize DNA. It was therefore of interest to determine whether the inhibitory action of SDI-1 could be overcome by the expression of T antigen. Moreover, it was desirable to determine that the action of SDI-1 was not due to the induction of a general metabolic imbalance in cells. If such were the case, one would not expect large T antigen to antagonize its effect. For these reasons, cells were co-transfected with SDI-1 cDNA and vectors in which T antigen was driven by the CMV promoter. Such co-transfection experiments revealed that the inhibitory activity of SDI-1 was largely abolished by the co-expression of the SV40 large T antigen.

Transient transfection assays were performed using an additional normal human fibroblast cell line (neonatal foreskin cell line (CSC303) and the WI38 immortal cell line in order to determine the generality of the inhibitory effect of SDI-1. In both cases, significant inhibition (40–50%) was observed. Furthermore, SDI-1 was found to inhibit SUSMI (40%) but not an SV40 transformed cell line GM639 or HeLa cells (<20%). The results thus far are consistent with earlier results obtained from heterokaryon experiments in which HeLa cells and cells transformed with SV40 virus were not inhibited by fusion with senescent cells. This provides further evidence that SDI-1 behaves like the inhibitor previously detected in senescent cells.

EXAMPLE 10

Southern Analysis of the SDI-1 Gene

In order to determine whether the absence or inactivity of SDI-1 was responsible for cellular immortality in any of the four complementation groups for indefinite division, genomic DNA and mRNA was examined from cell lines representative of the four groups. Southern analysis revealed the expected 5 and 10 kb bands after digestion with EcoRI. Therefore, no gross deletions or rearrangements have occurred in the SDI-1 gene in these cell lines. By Northern analysis, it was determined that SDI-1 mRNA was lower or absent in the cell lines that had been assigned to complementation groups B and C. SDI-1 was present at higher levels in cell lines representative of complementation groups A and D. This results suggests that part of the mechanism by which the cell lines may have escaped, cellular senescence is through the loss of ability to express sufficient levels of the active SDI-1 gene.

EXAMPLE 11

Characterization of SDI Sequences

Using a functional screening method, a novel DNA synthesis inhibitory gene, SDI-1, was identified. The gene is expressed at high levels in nonproliferating human diploid fibroblasts. Message levels of SDI-1 increased 10 to 20-fold as normal human cell cultures were aged in vitro, with the expression kinetics correlating closely with the phenotypic expression of cellular senescence. In addition, SDI-1 message increased when cells were made quiescent by growth factor deprivation.

The results described above demonstrate that SDI-1 codes for a novel, physiologically active gene product that is important for cell cycle control. Expression of the gene is modulated during exit from $G_0$ and entry into S phase in cells that have been stimulated to enter the cell cycle. In addition, expression of antisense SDI-1 message stimulates cells to enter the cell cycle in the absence of growth factors. The observation that SV40 T antigen can counteract the inhibitory activity of SDI-1 in a manner similar to that observed with the negative growth regulators p53 and Rb (Lane, D. P. et al., *Nature* 278:261–263 (1979); Linzer, D. I. H. et al., *Cell* 17:43–52 (1979); De Caprio, J. A. et al., *Cell* 54:275–283 (1988)), underscores the importance of this gene product in the regulation of the cell cycle.

The recombinant SDI-1 protein of the present invention inhibits the phosphorylation of histone H1 by CDK2. Since SDI-1 blocks DNA synthesis, this finding indicates that the phosporylation of histone H1 has a role in the initiation of DNA synthesis.

The SDI-1 gene product is also a potent inhibitor of several cyclin-dependent kinases, including CDC2, CDK2, and CDK4. In similar experiments using human cell extracts, recombinant SDI-1 was found to inhibit CDK2 kinase activity. These results are of particular importance in view of what is known about the various proteins involved in cell cycle progression. Several human G1 cyclin candidates (cyclins C, D, and E), identified by their ability to complement a budding yeast strain that lacked G1 cyclins (Xiong, Y. et al., *Cell* 65:691–699 (1991); Lew, D. J. et al., *Cell* 65:1197–1206 (1991); Xiong, Y. et al., *Curr. Biol.* 1:362–364 (1991); Koff, A. et al., *Cell* 66:1217–1228 (1991)), were found to be cell cycle regulated, with maximal mRNA expression occurring at different points in GI (Lew, D. J. et al., *Cell* 65:1197–1206 (1991)). Since D-type cyclins and cyclin E are associated with active kinase complexes (Koff, A. et al., *Cell* 66:1217–1228 (1991); 1992; Dulic, V. et al., *Science* 257:1958–1961 (1992); Matsushime, H. et al., *Cell* 65:701–7139 (1991); Ewen, M. E. et al., *Cell* 73:487–4976 (1993); Kato, J. Y. et al., *Genes Devel.* 7:331–342 (1993), it is likely that these kinases have a role in the commitment of mammalian cells to a new round of cell division at the "restriction point." (Pardee, A. B., Science 246:603–608 (1989)). Indeed, recent reports indicate that cyclin E-CDK2 kinase complexes have maximal activity in late G1 and early S phase (Dulic, V. et al., Science 257:1958–1961 (1992); Koff, A. et al., Cell 66:1217–1228 (1991)), and also have the ability to phosphorylate the RB protein in cultured human cells (Hinds, P. W. et al., Cell 70:993–1006 (1992)) and in vitro (Ewen, M. E. et al., Cell 73:487–4976 (1993)). This suggests that the kinase may play a pivotal role in the regulation of the G1-to-S phase transition of the cell cycle.

Immunoblots of SDI-1 protein have revealed that levels of this protein do not appear to vary extensively in cells in different growth states (ie. actively growing versus quiescent or senescent cells). However, consistently higher amounts of protein are present in non-dividing compared with proliferating cells. This seems reasonable because SDI-1 is a potent negative regulator of CDK activity, and tight regulation of this inhibitor would be essential for proper cell cycle regulation and progression. Small changes in the amount of inhibitor protein could result in a major impact on the various gene products it controls. At least two CDKs: CDC2 and CDK2, maintain relatively constant steady-state protein levels through the cell cycle despite cell cycle phase-dependent changes in mRNA. SDI-1 may be regulated in a similar manner, such that the level of SDI-1 protein is precisely controlled at a particular level, and that new CDK/cyclin synthesis and activation is needed to overcome the inhibitory effects of SDI-1 to allow for progression through the cell cycle. Thus, SDI-1 would prevent entry into the cell cycle until a required threshold of stimulatory gene products were present, allowing the cell to proceed through the "restriction point" of the cell cycle. Such a dynamic equilibrium between active CDK/cyclin complexes and the inhibitor SDI-1 protein explains the observed stimulation of DNA synthesis in quiescent cells following a small decrease in the steady-state levels of SDI-1 protein due to antisense SDI-1 mRNA expression. Thus, SDI-1 may function in the cell in a manner similar to other cell proliferation inhibitors, such as the tumor suppressor genes p53 and Rb, and the SDI-1 gene may be a target for mutation in various tumors.

Although senescent cells cannot be stimulated to enter S phase by the addition of mitogens, they do express mRNAs for many cell cycle-regulated genes including cyclins D1, cyclin E, CDK2, Rb, p53, c-H-ras, c-myc, c-jun, and jun B. However, several other important cell cycle-regulated genes, including c-fos, histone H3, CDC2, cyclin A, cyclin B1, and PCNA, are not expressed in mitogen-stimulated senescent cells. The lack of phosphorylation of the protein product of the retinoblastoma susceptibility gene Rb in senescent cells could be one cause for the inability of senescent cells to synthesize DNA. However, cyclin E-CDK2 complexes, though relatively abundant in senescent cells, lack the kinase activity which could potentially phosphorylate Rb in vivo.

The SDI molecules of the present invention are expressed at a higher level in senescent than in actively cycling cells. Thus, lack of proper CDK activity through the regulatory action of SDI-1 could be a key reason for the inability of senescent cells to enter S phase. This is supported by the fact that senescent cells are primarily deficient in events downstream of the postulated SDI-1 mediated inhibition of CDK2.

Overexpression of E2F-1, a component of the E2F-1 transcription factor which has a wide range of target genes, was found to be capable of reversing the inhibitory effect of SDI-1. It is well established that the tumor suppressor gene Rb, as well as the related p107 protein complexes with E2F-1 to inhibit transcription. Overexpression of cyclins A and E reverses pRb-mediated suppression of proliferation. In addition, overexpression of E2F-1 can induce quiescent REF-52 cells to synthesize DNA. Thus, in view of the observation that E2F-1 reverses the negative growth activity of SDI-1, E2F-1 may be the last step in a cascade of events controlled by p53, SDI-1 and Rb.

EXAMPLE 12

The Relationship between Cellular Tumor Suppressors and SDI Sequences

A role for SDI-1 in cell cycle arrest is indicated by the fact that in normal human cells made quiescent either by serum deprivation or growth to high density, SDI-1 mRNA levels were increased 10–20 fold compared with cycling cells. However, upon addition of serum, SDI-1 mRNA levels were found to rapidly decrease to low levels just prior to the onset of DNA synthesis. Thus SDI-1 appears to act as a "check point" to inhibit cell proliferation in the presence of unfavorable external conditions. Many immortal cell lines are unable to block initiation of DNA synthesis in response to insufficient growth factors. However, in accordance with the present invention, the overexpression of SDI-1 in various immortal human cells resulted in inhibition of DNA synthesis in several of the cell lines regardless of their ability to arrest cell proliferation in response to lowered growth factors.

The physiological significance between the overexpression of SDI-1 and the inhibition of cell proliferation by overexpression of SDI-1 is strengthened by the finding that SDI-1 can inhibit the kinase activity of cyclin/cdk2 complexes. Indeed, as indicated the addition of 250 ng of purified GST-SDI-1 fusion protein to cyclin/cdk2 complexes (immunoprecipitated from HeLa cell extracts by cdk2 antisera) resulted in half maxial inhibition of histone H1 kinase activity.

In order to further investigate the molecular mechanism through which SDI-1 mediated its anti-proliferative activity, the steady-state levels of SDI-1 RNA were evaluated in a number of immortal cell lines, including MDAH 041. The MDAH 041 cell line was derived from a Li-Fraumeni syndrome patient, and does not synthesize p53. The cells were found to be able to continue to synthesize DNA in the presence of low serum growth factors.

SDI-1 levels were determined by northern analysis and were normalized to either GAPDH or b-actin mRNA. DNA was introduced by electroporation. Rapidly growing cells were trypsinized and $10^6$ cells were resuspended in 0.5 ml phosphate buffered saline along with 10 µg of carrier DNA, 1 µg of pCMVb (MacGregor, G. R. et al., Nucl. Acids Res. 17:2365 (1989)) coding for the b-galactosidase gene and 1 µg pCMVSDI-1 (containing nucleotides 1–685 of SDI-1). Plasmid pCMVb served as a marker to detect cells that were capable of incorporating and expressing exogenous DNA. Following a pulse of 250–350 volts, $3 \times 10^5$ cells were seeded into 35 mm cell culture dishes. Tritiated thymidine (1 µCi/ml) was added to the culture medium 24–30 hours after electroporation and the cells were incubated for an additional 24 hours. The cells were fixed, stained for b-galactosidase activity, and processed for autoradiography to determine the percentage of b-galactosisase positive cells that had synthesized DNA in the presence of the tritiated thymidine. The percent inhibition was determined relative to control cells that were transfected with pCMV vector and pCMVb. Calcium transfection was used in the case of MDAH 041 cells. The correlation between SDI-1 mRNA levels and DNA synthesis is presented in Table 6. The data presented are averages of at least two experiments.

TABLE 6

Correlation between SDI-1 mRNA Level and Inhibition of DNA synthesis

| Cell Line | % Inhibition | SDI-1 mRNA level | P53 Status |
|---|---|---|---|
| MADH 041 | 95 ± 4 | Not Detectable | Mutant |
| SAOS2 | 47 | Not Done | Mutant |
| TE85 | 75 ± 7 | Not Detectable | Mutant |
| T98G | 35 ± 5 | Not Detectable | Mutant |
| Hela | 60 ± 5 | Low | HPV-18 infected |
| A1698 | 15 ± 3 | Normal | Wild-type |
| UABC023 Ser 31 → Arg 31 Homozygous | 57 ± 6 | Low | Unknown |
| GM639 | 78 | Normal | SV40-transformed |
| GM847 Ser 31 → Arg 31 Heterozygous | 21 | Normal | SV40-transformed |
| RN13 | No Inhibition | Normal | Unknown |
| PR282 | No Inhibition | Normal | Unknown |

As indicated in Table 6, SDI-1 mRNA levels were found to be very low or undetectable in several cell lines which also lacked wild type p53 protein. Significantly, SDI-1 RNA and protein was undetectable the MDAH 041 cells. The correlation between p53 level and SDI-1 level suggested that p53 mediated its tumor suppressing activity by inducing a senescent state through the induction of SDI-1, and that cells which lacked p53 were neoplastic due to their inability to induce SDI-1 expression.

In view of the well established role of p53 in cell growth control and as a transcriptional activator or suppressor, and the fact that MDAH 041 cells do not express wild type p53, the finding that they also lacked SDI-1 expression indicated that the introduction of p53 into these cells would result in an induction of SDI-1 expression and thus, in growth arrest.

To further demonstrate the ability of p53 to induce SDI-1 expression, p53 was introduced into MDAH 041 cells. Such introduction resulted in increased expression of SDI-1 and in the inhibition of DNA synthesis, as measured by tritiated thymidine autoradiography. The degree of inhibition increased with the amount of p53 plasmid introduced. If the inhibition of DNA synthesis observed was due to an induction of SDI-1 by p53, rather than by some other effect of p53, the inhibitory activity would be lost following co-transfection of antisense SDI-1 sequences.

Therefore, to demonstrate the direct induction of SDI-1 by p53, the above-described SDI-1 and antisense SDI-1 gene sequences were co-transfected with a p53 gene construct into normal human fibroblasts. As expected, the antisense construct was found to eliminate 80% of the inhibition of DNA synthesis caused by SDI-1 alone. When 4 μg of SDI-1 and increasing amounts of p53 plasmids were co-transfected into MDAH 041 cells, the antisense SDI-1 was found to be capable of effectively counteracting the inhibition of DNA synthesis caused by p53 alone. These findings are summarized in Table 7. This finding verified the conclusion that one manner in which p53 causes inhibition of DNA synthesis is by activating the expression of SDI-1 and that such induction of SDI-1 is a requisite for part of the DNA synthesis-inhibitory activity of p53. Such activation occurs, at (east in part, by the transcriptional activation of the SDI-1 gene. The expressed SDI-1 protein acts, in part, by inhibiting the kinase activities of CDK/cyclin complexes and can therefore act at multiple points in the cell cycle to block progression. Loss of wild type p53 activity would lead to lack of expression of SDI-1 and thereby result in inappropriate cell cycle progression.

TABLE 7

The Induction of SDI-1 by P53

| Amount of P53 DNA Transfected (ng) | DNA Synthesis (as approx. % of control) | |
|---|---|---|
| | P53 Alone | P53 + anti-SDI-1 |
| 0 | 100 | 121 |
| 10 | 25 | 50 |
| 30 | 15 | 45 |
| 100 | 10 | 25 |

Mutations in the gene encoding the p53 protein are common in human tumors with approximately 50% of tumors expressing a mutant p53. This has led to the conclusion that p53 acts as a negative growth regulator and is a tumor suppressor gene. One aspect of the present invention concerns the recognition of the molecular mechanism responsible for the anti-oncogene activity of p53. SDI-1 has been found to be an inhibitor of cell cycle progression which acts at least in part by inhibiting the kinase activities of cdk/cyclin complexes. As such it can act at multiple points in the cell cycle to block progression. Since p53 is required for transcriptional activation of SDI-1, inactivation of this function could allow uncontrolled and inappropriate cell cycle progression. This would allow cells to ignore the normal external signals for cell cycle stasis and permit proliferation in situ. Since SDI-1 is downstream of p53, SDI-1 appears to be the effector of p53 action. Furthermore, mutations have been found in SDI-1 which may contribute to altered cell proliferation in cells without mutated p53.

EXAMPLE 13

Capacity of SDI-1 to Suppress the Proliferation of Tumor Cells

As indicated above, SDI-1 has the capacity to suppress the proliferation of tumor cells. To demonstrate this ability, cells derived from several human tumors were incubated in the presence or absence of a glutathione S-transferase-SDI-1 fusion protein. In the experiment, $5 \times 10^3$ cells were plated overnight at 37° C. (only for adherent cells) and then incubated with the SDI fusion protein. After 48 hours at 37° C., cells were pulsed with thymidine for 24 hours and then harvested. The results of this experiment are shown in Table 8; the thymidine incorporation by untreated cells was expressed as 100%. all determinations were made in quadruplicate.

TABLE 8

Antiproliferative Effects of SDI-1

| Cell Line | Relative Cell (% of Control) | |
|---|---|---|
| | 50 μg/ml | 30 μg/ml |
| Myeloid Cells: | | |
| Promyelocytic (HL-60) | 1 ± 0 | 1 ± 0 |
| Promonocytic (ML-1) | 1 ± 0 | 1 ± 0 |

TABLE 8-continued

Antiproliferative Effects of SDI-1

| Cell Line | Relative Cell (% of Control) | |
|---|---|---|
| | 50 μg/ml | 30 μg/ml |
| Myelogenous (KG-1) | 1 ± 0 | 1 ± 0 |
| Myelogenous (KG-1a) | 1 ± 0 | 1 ± 0 |
| Histiocytic Lymphoma (U-937) | 1 ± 0 | 1 ± 0 |
| Promonocytic (THP-1) | 1 ± 0 | 1 ± 0 |
| B Cell Lymphoma | | |
| Burkitt Lymphoma (Daudi) | 1 ± 0 | 3 ± 0 |
| Burkitt Lymphoma (Raji) | 1 ± 0 | 1 ± 0 |
| Epithelial Cells | | |
| Breast (BT-20) | 1 ± 0 | 1 ± 0 |
| Breast (BT-20 TNF R) | 1 ± 0 | 1 ± 0 |
| Breast (SK-BR3) | 1 ± 0 | 1 ± 0 |
| Breast (MCF-7) | 1 ± 0 | 1 ± 0 |
| Breast (T-47 D) | 2 ± 0 | 2 ± 0 |
| Lung adenocarcinoma (A-549) | 25 ± 3 | 40 ± 1 |
| Hepatocellular (Hep G2) | 12 ± 2 | 21 ± 3 |
| Glioblastoma Cells | | |
| Glial (U-251) | 35 ± 2 | 66 ± 4 |
| Normal Cells | | |
| Human umbilical vein endothelial cells | 2 ± 1 | 5 ± 1 |
| Human foreskin fibroblasts | 1 ± 0 | Not Done |
| Murine Tumor Cells | | |
| Fibroblasts (L-929) | 4 ± 1 | Not Done |

The above experiment indicates that tumor cells treated with SDI-1 exhibited a profound suppression of DNA synthesis.

EXAMPLE 14

Effect of SDI-1 cDNA on the Proliferation of Tumor Cells

The capacity of SDI-1 cDNA to repress the proliferation of tumor cells was evaluated. SDI-1 cDNA was introduced into a number of tumor derived and other cell lines by electroporation. One μg of the CMV-SDI-1 plasmid was mixed with 1 μg of plasmid containing the CMV promoter and the β-galactosidase gene. After electroporation, cells were plated and 24 hours later assayed for the ability to incorporate tritiated thymidine. SDI-1 cDNA caused significant inhibition of DNA synthesis in a number of tumor derived cell lines including a melanoma, lung tumor and a brain tumor. The SDI-1 cDNA also inhibited DNA synthesis in mouse 3T3 cells and in normal bovine smooth muscle cells. Three tumor derived cell lines (one lung tumor cell line, and two kidney tumor cell lines) were unresponsive to the SDI-1 cDNA.

EXAMPLE 15

Effect of SDI-1 Antisense cDNA on the Proliferation of Normal Cells

The effect of SDI-1 on DNA synthesis was also evaluated using antisense expression vectors. SDI cDNA was provided to cells by introducing plasmid pCMVSDI684 which is a derivative of plasmid pCMVβ that lacks the β-galactosidase gene, and which contains nucleotides 1–684 of the SDI-1 cDNA sequence. Antisense vectors were constructed by cloning SDI-1 antisense sequences into pMET, an inducible expression vector containing an altered human metallothionein promoter (CSIRO, Biomolecular Engineering, New South Wales, AU). The promoter contains a deletion in the basal promoter and the addition of synthetic metal response elements in triplicate. For construction of pMET, adenovirus sequences containing E1A gene 12S and 13S introns (i.e. nucleotides 917–1673) were first cloned into the mammalian expression vector pRc/CMV (Invitrogen) at the NotI/ApaI sites of the multiple cloning region of this plasmid to create pRc/CMV-Ad. To ensure that no translation of E1A sequences occurred, and to create an SPEI cloning site in the vector, an SPEI linker containing a stop codon was inserted between the CMV promoter and the E1A splice sequence in-frame with the E1A sequence. The CMV promoter of plasmid Rc/CMV-Ad was then replaced with the pM26 promoter to create pMET.

To accomplish this, the metallothionein promoter was excised from pM26 by BglII digestion and inserted into the BamHI site of pBluescript (Stratagene). An EcoRV and NotI fragment containing the promoter was then subcloned from pBluescript into a filled-in BglII site and NotI site of Rc/CMV-Ad. Antisense sequences from the SDI-1 cDNA were derived from the full length cDNA cloned into the BamHI site of pBluescript. The StuI site at nucleotide 127 was converted to a SpeI site by insertion of an SpeI linker to make SDISPE127. An SpeI linker was also inserted at the ApaI site at nucleotide 319 to create SDISPE319. These constructs were digested with SpeI and inserted in antisense orientation into the SpeI cloning site of pMET, thus creating the SDI antisense expression vectors pMET-AS127 (having the first 127 nucleotides of the antisense strand to SDI-1 cDNA, SEQ ID NO:1) and pMET-AS318 (having the first 319 nucleotides of the antisense strand to SDI-1 cDNA, SEQ ID NO:1).

Cell lines expressing SDI-1 antisense were obtained by calcium phosphate transfection. $3 \times 10^5$ HCA2 cells (human foreskin cells) at population doubling 10 were transfected with 20 μg pMET, pMETAS127, or pMETAS318. Following two weeks of G418 selection, colonies were picked and expanded. Inducibility and integrity of the inserted sequence was determined using stable transformants by addition of 100 μM $ZnCl_2$ and 2 μM $CDCl_2$ followed by RNA analysis of total cell RNA. The analysis was an RNase protection using antisense RNA probes, internally labeled with [$^{32}$P]-UTP. The probe pMET+SDI-1, containing SDI-1 nucleotides 444–686 (of SEQ ID NO:1), was used to measure the expression of SDI-1 from both the transfected genes and endogenous mRNA. After EcoNI digestion, transcription from the SP6 promoter in the pMET vector resulted in an antisense labeled probe that hybridized to both RNA from the expression vector and to endogenous SDI-1 mRNA. This allowed a comparison of relative levels of expression from the introduced construct and SDI-1 endogenous RNA. As a control, β-actin mRNA was measured in all assays.

In order to determine the extent of DNA synthesis, the cells were trypsinized and $1 \times 10^4$ cells were seeded per well in 24 well plates. Four to six hours after plating, the cells were washed 3 times with phosphate buffered saline and the medium was replaced with medium containing 0.5% fetal bovine serum. This serum deprivation induced the cells to become quiescent. Six to ten days later, the medium was replaced and metal was added to induce the metallothionein promoter. The amount of metal added was optimized for each plasmid; optimized amounts were 70 μM $ZnCl_2$ and 1.4 μM $CdCl_2$ for pMET1 and 50 μM $ZnCl_2$ and 1 μM $CdCl_2$ for AS1. Twenty hours later, induction was boosted by the addition of fresh medium. [$^3$H]-thymidine (1.5 μCi/ml) was added to each culture 4 hours later. Twenty-four hours later, cells were fixed and analyzed by autoradiography. The results obtained in a typical experiment are shown in Table 9, and demonstrate the capacity of the antisense molecules of the present invention to induce the proliferation of quiescent cells.

TABLE 9

| Cell Line | % of Cells Labeled | |
|---|---|---|
| | Before Metal Induction | After Metal Induction |
| No Integrant | <5% | 5% |
| Vector Control | <5% | 5% |
| Antisense Construct I | 7% | 49% |
| Antisense Construct II | <5% | 57% |

EXAMPLE 16

Ability of SDI-1 Antisense Oligonucleotides to Repress the SDI-Mediated Inhibition of Proliferation As discussed above, the expression of SDI-1 inhibits DNA synthesis. In some instances, such as to immortalize human cells in culture, it is desirable to repress such inhibition. The SDI-1 antisense molecules of the present invention are capable of mediating such repression.

In order to demonstrate the capacity of SDI-1 antisense oligonucleotides to repress the DNA synthesis-inhibitory effects of SDI-1, cells were provided with an oligonucleotide having the sequence:

SEQ ID NO:3 AGCCGGTTCTGACATGGCG

This oligonucleotide is antisense to SEQ ID NO:1 at nucleotides 75–93.

Cells were cultured in medium containing 10% fetal bovine serum (FBS) for approximately one week, at which time the medium was replaced with medium containing 0.5% FBS. The cells were divided into control cells and experimental cells. On Day 1, experimental cells were provided with either 1, 2 or 5 $\mu$M of the above-described oligonucleotide; Control cells received no oligonucleotide. On Day 3, and again on Day 5, all cells received fresh medium containing 0.5% FBS; experimental cells received additional oligonucleotides (1, 2 or 5 $\mu$M). On Day 6, tritiated thymidine was added to the culture media and the cells were harvested on day 7. Experimental cells (that had received the antisense oligonucleotide) exhibited an increase in the amount of tritiated thymidine incorporated into their DNA, relative to the control cells.

The results indicated that oligonucleotides that contain regions complementary to SDI-1 nucleotides 75–93 can act as antisense repressors of SDI-1 function.

EXAMPLE 17

Effect of DNA Damage and Growth Arrest on the Expression of SDI-1

The above-described experiments demonstrated that p53 induces SDI-1 expression, and that the production of SDI-1 mRNA was induced in contact-inhibited and serum-deprived cells, as well as in senescent human cells. To determine whether the induction of SDI-1 was a general characteristic of growth arrest states, the effect of DNA damage on SDI-1 mRNA levels was evaluated.

Cells are believed to undergo growth arrest in response to DNA damaging agents before entering the S or M phases of the cell cycle. The growth arrest permits the cell to repair any genetic lesions caused by the DNA damaging agents. A failure to repair such damage creates a mutation, and may have severe consequences ranging from cell death to neoplasia. Thus, the capacity of a cell to undergo, growth arrest in response to DNA damage has great importance both in the etiology of cancer and in the response of cancer cells to chemotherapy.

To evaluate the effect of DNA damaging agents on SDI mRNA production, normal human neonatal foreskin fibroblast cells (strain HCA2); an immortalized cell line (TE85, obtainable from the American Type Culture Collection, Rockville, Md., US), and the above-described MDAH 041 cell lines were employed. All cells were cultured in Eagle's minimal essential medium with Earl's salts plus 10% fetal bovine serum (Gibco BRL, Gaithersburg, Md., US) in 5% $CO_2$ at 37° C., or in Hanks salts plus 10% fetal bovine serum at 37° C. HCA2 cells achieve approximately 80 population doublings before becoming senescent. The cells were used at population doubling 27 or less.

Cells were plated at $1 \times 10^4$ cells/cm$^2$ on glass coverslips and grown 24–48 hours to 50–75% confluency and were then treated with one of several DNA damaging agents: γ-rays (4 Gy); bleomycin (75 $\mu$g/ml; 4 hours), etoposide (400 $\mu$M in 4% DMSO; 8 hours), hydrogen peroxide (400 $\mu$M; 1 hour), UV light (30 J/m$^2$), methyl methane sulfonate ("MMS") (100 $\mu$g/ml; 4 hours), mitomycin C ("MMC") (5 $\mu$g/ml; 30 hours) and $CdCl_2$ (250 $\mu$M; 1 hour). For UV irradiation, cells were cultured in 150 cm$^2$ tissue culture dishes. Immediately prior to treatment the medium was removed and the dishes, without lids, were placed in a Stratagene (La Jolla, Calif., US) StratalinkerUV cross-linking device and irradiated with a dose of 30 J/m$^2$. Fresh serum-supplemented medium was then added and the cells were incubated at 37° C., 5% $CO_2$. γ-irradiation was performed on cells in complete cell culture medium in 25 cm$^2$ tissue culture flasks, using a fixed $^{137}$Cs source. The dose rate was 4.21 Gy/min. Exposure was to 4 Gy. In addition, the effects of heat shock (42° C.; 4 hours), hydroxyurea (2 mM; 24 hours) and prostaglandin $A_2$ (10 $\mu$g/ml in 0.1% ethanol; 24 hr) were evaluated.

Tritiated thymidine was added 16 hours following each such treatment and the cells were incubated for 8 hours, fixed and processed for autoradiography; as described above. RNA was harvested 4 or 24 hours post treatment using RNAzol B (Cinna/Biotecx, Houston, Tex.) according to the manufacturer's protocol. 10–20 $\mu$g of RNA was separated on a 1.2% agarose gel with 20% formaldehyde, transferred to a Gene screen plus (EN, Boston, Mass.) membrane, probed, and quantitated. Fold induction was determined by comparing treated samples with untreated controls. Controls were mock treated cells put through the same washing, media change, transportation, and inadvertent temperature fluctuation as those receiving treatment. Controls for agents dissolved in ethanol or dimethyl sulfoxide were exposed to the same concentration of the solvent alone. SDI-1 RNA values were normalized to GAPBH levels. In some cases normalization to actin RNA was also done and revealed no substantial differences in fold induction. The results of this experiment are shown in Table 10.

TABLE 10

Induction of SDI-1 mRNA and Growth Arrest by Various Treatments

| Mechanism of Action | Agent | Dose | SDI-1 Level* | % Growth Arrest |
|---|---|---|---|---|
| Double-Stranded Breaks | γ-ray | 4 Gy | 2.0 | 70% |
| Double-stranded Breaks | bleomycin | 75 μg/ml 4 hr | 11.8 | 100% |
| Protein Associated Double-Stranded Breaks | etoposide | 400 μM 8 hr | 8.0 | 100% |
| Free Radicals | $H_2O_2$ | 400 μM 1 hr | 6.3 | 95% |
| Bulky Adducts (some free radicals) | UV light | 30 J/m$^2$ | 15.2 | 60% |
| Alkylation | MMS | 100 μg 4 hr | 3.27 | 53% |
| Cross-Linking | Mitomycin C | 5 μg/ml 30 hr | 2.8 | 100% |
| Mutagenic Metal | $CdCl_2$ | 250 μM 1 hr | 1.3 | 0% |
| General Stress | Heat Shock | 42° C. 4 hr | 2.3 | Not Done |
| Inhibitor of dNTP Synthesis | hydroxyurea | 2 mM 24 hr | 7.9 | 100% |
| Paracrine Hormone | prostaglandin $A_2$ | 10 μg/ml 24 hr | 6.1 | 100% |

*Fold induction of SDI-1 at 24 hour level

Preliminary studies (El-Deiry, W. S. et al., *Cell* 75:817–825 (1993)) suggested that the production of WAF1 might be induced by UV light. The above experiments demonstrate that the production of SDI-1 mRNA is induced by DNA damage and other growth arrest treatments in both normal cells and cells that lack wild type p53. The results of the above-described experiment demonstrate the role of SDI-1 in the repair of DNA damage or mutations that could lead to neoplasia in mammalian cells.

Every agent studied, with one exception, was found to cause an increase in SDI-1 mRNA in these cells (Table 10). Cadmium chloride, at the concentration used, failed to increase SDI-1 message level. However, itritiated thymidine incorporation analysis revealed that the cadmium chloride treatment did not induce growth arrest (no inhibition of DNA synthesis) (Table 10). In contrast, growth arrest, as measured by tritiated thymidine incorporation, was essentially complete in response to the other agents tested (Table 10). However, in the case of UV irradiation and MMS treatment, an inhibition of only 50–60% was observed. It is possible that growth arrest, in response to these agents, had not reached its maximum at the time DNA synthesis was measured or conversely that cell proliferation had already resumed. The lack of induction by cadmium chloride indicates that SDI-1 message was increased by DNA damage only when the damage caused growth arrest. This is supported by the observation that hydrogen peroxide was unable to further elevate SDI-1 mRNA levels in cells that were already growth arrested by contact-inhibition.

The kinetics of SDI-1 RNA induction by γ-irradiation and hydrogen peroxide treatment was found to differ (FIG. 6), providing further evidence for multiple mechanisms involved in regulating SDI-1 gene expression. Induction of SDI-1 message by γ-irradiation follows a time course for this gene by p53. It has been demonstrated in mouse prostate cells that p53 activity increases rapidly (within 30 minutes) following exposure to ionizing radiation and then declines to baseline level within 3 hours (Lu, X. et al., *Cell* 75:765–778 (1993)). The induction of SDI-1 mRNA observed in normal human cells is similar to this pattern though lagging in time slightly as would be expected. The major difference is that SDI-1 message declined more slowly (over approximately 30 hours) than p53 activity, thus explaining the observation of Lu, X. et al. (*Cell* 75:765–778 (1993)). The induction of SDI-1 mRNA observed in normal human cells is similar to this pattern though lagging in time slightly. The major difference is that SDI-1 message declined more slowly (over approximately 30 hours) than p53 activity. This explains the observation of Lu, X. et al. (*Cell* 75:765–778 (1993)), that ionizing radiation-induced arrest lasts for 20–30 hours, long after p53 activity had declined.

Figure 6:
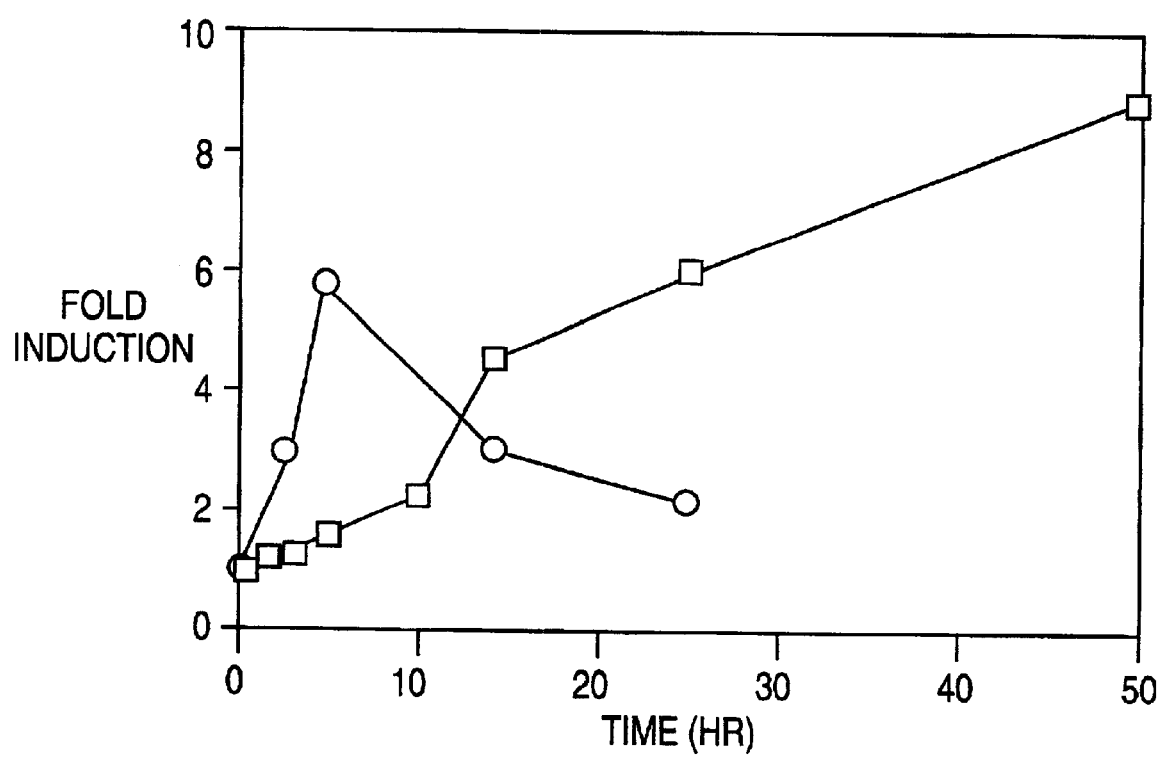
FIG. 6 shows the kinetics of SDI-1 induction in young cells (population doubling 28) obtained following exposure to either 4 Gy of γ-irradiation (open circles) or 400 μM hydrogen peroxide for 1 hour (closed circles).

Induction of SDI-1 message by hydrogen peroxide (FIG. 6) exhibited a very different pattern. It has been proposed that exposure to hydrogen peroxide results in a rapid increase in p53 activity (Tishler, R. B. et al., *Canc. Res.* 53:2212–2216 (1993)), which returns to baseline by 4 hours post-treatment. SDI-1 mRNA level, in contrast, did not rise significantly until 9 hours after treatment and continued to increase for at least 48 hours (FIG. 6). The slow response of SDI-1 RNA level to hydrogen peroxide treatment indicates that while an elevated level of SDI-1 mRNA appears to be universally associated with growth arrest, it may not always be the initial cause of the arrest. A similar pattern of SDI-1 message elevation was observed by serum-deprivation and contact-inhibition of normal human cells and resembles what is observed in cases of mRNA stabilization. A slow increase of mRNA in response to serum-deprivation and contact-inhibition has also been noted for the GADD genes (Fornace, A. J. et al., *Molec. Cell. Biol.* 9:4196–4203 (1989)). In all these cases, SDI-1 may act to maintain growth arrest after it has been initiated by another pathway.

EXAMPLE 18

Role of P53 in the SDI-1 Response to DNA Damage and Growth Arrest

As indicated, agents that cause growth arrest but do not damage DNA (heat shock, hydroxyurea, and prostagiandin $A_2$) were also examined (Table 10) and found to cause an increase in SDI-1 message levels. Heat shock and hydroxyurea treatments increased SDI-1 message (Table 10) though both have been shown not to increase p53 activity (Lu, X. et al., *Cell* 75:765–778 (1993); Zhan, Q. et al., *Molec. Cell. Biol.* 13:4242–4250 (1993)), indicating these agents may operate through a p53-independent mechanism.

In order to further investigate this possibility, the p53 status of various immortal cell lines was determined through immunoprecipitation studies and compared to the steady state level of SDI-1 mRNA in the same cell lines. For this purpose, cell lines were grown to approximately 70% confluence in 75 cm$^2$ flasks prior to being cultured for 1 hour in methionine-free modified Dulbecco's Eagle medium, and then labeled in methionine-free medium containing 10% dialyzed fetal bovine serum and 100 μCi/ml L-[$^{35}$S] methionine (TRAN35SLABEL; ICN). One flask was used per immunoprecipitation. After a 3 hour incubation in this labeling medium, the cells were placed on ice, washed with ice-cold phosphate buffered saline (PBS) and harvested in lysis buffer (20 mM Tris, pH 7.4, 150 mM NaCl, 0.5% NP-40, 1 mM EDTA, 50 μg/ml leupeptin, 30 μg/ml aprotinin). Lysates were scraped into microfuge tubes and sheared 3 times by passage through a 25 gauge needle. Phenylmethylsulfonyl fluoride was added to a final concentration of 1 mM and lysates centrifuged at 14,000 r.p.m. in an Eppendorf microfuge at 4° C. for 45 min. Supernatant volumes were adjusted to normalize for cell number, then precleared for 30 minutes at 4° C. for 45 min. Supernatant volumes were adjusted to normalize for cell number, then precleared for 30 minutes at 4° C. on a rotating wheel with approximately 40 μl packed volume of protein A-agarose (Pharmacia) that had been sequentially coated with rabbit anti-mouse IgG (ICN) and a mixture of two mouse IgG2a myeloma proteins (ICN). Lysates were then microfuged and each resulting supernatant was incubated with 50 μl packed volume of protein G PLUS/Protein A-agarose (Oncogene Science) coated with 4 μg of an appropriate p53-specific antibody or a nonspecific antibody of the same class and subclass. Specific antibodies were PAb421, which binds both wild-type and mutant forms of P53, PAb 240, which recognizes a subset of mutant forms, and PAb1620, which recognizes wild type p53 specifically. All p53 antibodies were obtained from Oncogene Science. Non-specific antibodies used were either a non-specific $IgG_1$ antibody to E. coli anthranilate syntheses protein or a mixture of two $IgG_{2a}$ myeloma proteins. Incubations were carried out for 2 hours at 4° C. on a rotating wheel. Samples were microfuged and pellets washed 4 times with ice-cold wash buffer (20 mM Tris, pH 7.5, 150 mM NaCl, 0.5% NP-40, and 0.1% SDS) then 2 times with PBS. Samples were resuspended in 2xloading buffer (4% SDS-polyacrylamide gel, pH 8.8. The gel was fixed, treated with Amplify (Amersham), dried and exposed to Kodak X-AR film for 20–28 hours at 80° C.

If p53 had been the only regulator of SDI-1 mRNA transcription, the absence of wild type p53 would have coincided with a low level of SDI-1 expression, whereas, the presence of functional p53 should have corresponded to a higher level of SDI-1 expression.

Evidence for a p53-independent mechanism of regulation of SDI-1 expression was obtained by exposing TE85 and MDAH 041 cells, which lack functional p53, to many of the agents described in Table 10 and determining changes in SDI-1 message levels. TE85 is an osteosarcoma derived line, which has been found, by imunoprecipitation, to express, only mutant p53. All treatments examined except γ-irradiation, which requires wt p53 for $G_1$ arrest (Kuerbitz, S. J. et al., *Proc. Natl. Acad. Sci. USA* 89 :7491–7495 (1989)), were able to increase SDI-1 message in the cell line TE85 (Table 11). The p53-independent upregulation of SDI-1 RNA level was confirmed in MDAH041 cells following hydrogen peroxide and hydroxyurea treatment (Table 11). The pattern of SDI-1 mRNA accumulation is therefore similar to that of GADD45. This gene also requires functional p53 for induction by γ-irradiation but not by most other agents (Zhan, Q. et al., *Molec. Cell. Biol.* 13:4242–4250 (1993)). GADD45 is a member of a family of genes that were identified based upon their induction by both growth arrest and DNA damage (Fornace, A. J. et al., *Molec. Cell. Biol.* 9:4196–4203 (1989)). These findings indicate that P53 is not the only regulator of SDI-1, and that additional regulators of SDI-1 exist. The above methods can be used to identifiy such additional regulators.

TABLE 11

| Agent | TE85 | MDAH 041 |
|---|---|---|
| Control | 1 | 1 |
| γ-rays | 1.3 | 1.1 |
| etoposide | 2.6 | |
| $H_2O_2$ | 4.0 | 3.3 |
| UV light | 3.0 | |
| MMS | 4.4 | |

TABLE 11-continued

| Agent | TE85 | MDAH 041 |
|---|---|---|
| MMC | 2.5 | |
| Hydroxyurea | 7.5 | 2.5 |

In summary, the above results demonstrate that: 1) a wide variety of agents that induce growth arrest, including those that damage DNA, elevate SDI-1 message level; 2) some agents can accomplish this in the absence of functional P53 and 3) this elevation follows two distinct temporal patterns. In one, a rise in p53 activity results in a parallel increase in SDI-1 mRNA. This occurs early enough to be causative of arrest. In the second, an inhibitor of growth causes arrest by a mechanism that does not depend entirely upon p53. This arrest is associated with a gradual accumulation of SDI-1 mRNA, perhaps due to an increase in message stability.

EXAMPLE 19

Production of Monoclonal Antibodies to SDI-1 Fusion Proteins

Anti-SDI-1 monoclonal antibodies were isolated as described above using the GST-SDI-1 fusion as an immunogen and using the $[His]_6$ fusion having the leader sequence of SEQ ID NO:4 in a screen for suitable hybridomas. All of the antibodies could immunoprecipitate both cellular and recombinant SDI-1 protein in addition to the GST-SDI-1 fusion protein.

The monoclonal antibodies were used to in an imunohistochemical evaluation of human tissue. Antibodies (10 μg/ml) from four hybridoma lines (18A10; C6B6; 8A8; 2G12), and from a mouse $IgG_{2b}$ control, were incubated with neat supernatant overnight at 4° C. Antibody was detected using the Vector Standard ABC kit with DAB as chromogen. Tissue from human tonsil (containing both a lymphoid and an epithelial cell component), adult human skin (containing both connective tissue and epithelial cell components) or adult human colon (containing connective tissue and glandular epithelial cell components) was evaluated. Staining was evaluated on a qualitative +/− scale. The control antibody failed to elicit staining on any tissue.

Monoclonal Antibody 18A10

Tonsil all epithelial cell layers, all lymphocytes and all stromal components did not stain.

Skin all upper layers and possibly the basal cell layer showed a trace to 1+ diffuse cytoplasmic staining. The connective tissue components did not stain.

Colon Epithelial cells did not stain. The mucous within the glands exhibited a trace to 1+ staining. The connective tissue components did not stain.

Monoclonal Antibody C6B6

Tonsil all epithelial cell layers, all lymphocytes and all stromal components did not stain.

Skin basal cell epithelial cells had a +/− to trace+ diffuse cytoplasmic staining. The connective tissue components did not stain.

Colon Individual cells among the epithelial cells showed a 3+ nuclear/cytoplasmic staining. The mucous within the glands did not stain. The connective tissue components did not stain.

Monoclonal Antibody 8A8

Tonsil all upper layer epithelial cell layers and possibly basal cells showed a +/− to trace+ diffuse cytoplasmic staining. Lymphocytes and all stromal components did not show immuno-reactivity.

Skin all upper epithelial cells showed a +/− to 1+ diffuse cytoplasmic staining. The connective tissue components did not stain.

Colon Areas of epithelial cells showed a 3+ nuclear/cytoplasmic staining. The mucous exhibited a +/− staining. The connective tissue components did not stain.

Monoclonal Antibody 2G12

Tonsil the basal cell epithelial layer showed a trace to 1+ staining. Some lymphocytes exhibited a trace membrane staining. The stromal components did not stain.

Skin the basal cell layer showed a trace to 1+ diffuse cytoplasmic staining. The upper cell layers did not appear to stain.

Colon Significant brown precipitated material was evident, suggesting that some ductal epithelail cells were exhibiting a strong nuclear stain. The mucous within the glands did not stain. The connective tissue components did not stain The experiment indicated that the monoclonal antibodies could distinguish between tissue types that expressed SDI-1 and those that did not express SDI-1. Moreover, it was possible to discern a differential pattern of staining in different cell types. The immunohistochemical evaluation could be performed on biopsied tissue. The detection of non-staining foci of cells within the tumor mass would be indicative of cells that no longer expressed SDI-1, and which therefore would warrant more aggressive antineoplastic and antimetastatic therapy.

EXAMPLE 20

Delivery of SDI-1 to Target Cells

The ability to deliver a, pharmacological agent to a cell constitutes a general problem in defining therapeutic protocols. In order to evaluate the role of the GST moiety in facilitating the cellular uptake of SDI-1, the drug-delivery capacity of two GST-SDI-1 constructs was evaluated.

Construction of the First GST-SDI-1 Fusion

The first of these fusions was the especially preferred *Schistosoma japonicum* GST-SDI-1 fusion (discussed above) that had been initially recognized as being capable of entering target cells. Remarkably, however, slight modifications in the structure of this fusion were found to substantially destroy its capacity to be taken up by target cells. Thus, the originally described *Schistosoma japonicum* GST-SDI-1 fusion had inherent and distinctive characteristics that were not previously fully recognized.

The especially, preferred *Schistosoma japonicum* GST-SDI-1 fusion was formed by cleaving plasmid pcDSRαΔ-SDI-1 with Acyl and EcoRI, thereby liberating an SDI-1-encoding fragment. Acyl cleaves the plasmid 4 nucleotides preceding the SDI-1 initiation codon; EcoRI cleaves the molecule at approximately position 1010 of SEQ ID NO:1. The fragment was then cloned between the Smal and EcoRI sites of plasmid pBS. This construct was then cleaved with BamHI and EcoRI to release an SDI-1-encoding fragment that contained the nucleotides: GGATCCCCCCGCC (SEQ ID NO:7) immediately preceding the SDI-1 ATG initiation codon. The distal terminus of the molecule was at approximately position 1010 of SEQ ID NO:1.

Plasmid pGEX2T, which contains the *Schistosoma japonicum* GST-encoding sequence was cleaved with BamHI and EcoRI. The BamHI enzyme cleaves the *Schistosoma japonicum* GST-encoding sequences at a site located at nucleotides 662–667 of the molecule (approximately at codon 226 of the molecule); the EcoRI enzyme cleaves the plasmid outside of the GST-encoding sequences. The dual enzymatic cleavage prevents religation of the plasmid, and ensures that the SDI-1 sequences will be introduced in the proper orientation.

The BamHI-EcoRI treated pGEX2T DNA was incubated with the above-described SDI-1-encoding fragment that contained, at one end the nucleotides: GGATCCCCCCGCC (SEQ ID NO:7) immediately preceding the SDI-1 ATG initiation codon, and at the other end an EcoRI cleavage site. Ligation of the two molecules produced a plasmid in which the SDI-1-encoding sequences were fused one nucleotide out of frame from the GST-encoding sequences. In order to restore reading frame, the plasmid was cleaved with BamHI, the staggered ends were filled in using Klenow DNA polymerase, and then ligated to a 10 base pair XhoI linker (Promega) having the sequence: CCCTCGAGGG (SEQ ID NO:8). Thus, the final construct contained sequences encoding amino acids 1–226 of GST fused to a 9 residue fragment that encoded Pro-Arg-Gly (residues 1–3 of SEQ ID NO:9) fused to a BamHI-filled linker (SEQ ID NO:7) that encoded Asp-Pro-Pro-Ala (residues 4–7 of SEQ ID NO:9) fused to the ATG initiation codon of SDI-1 and the remainder of the SDI-1-encoding sequence. The nucleotide sequence of the complete gene fusion is provided in SEQ ID NO:10; the amino acid sequence encoded by this gene fusion is provided in SEQ ID NO:11. An *E. coli* strain transformed with plasmid pAG20, containing the above-described first GST-SDI-1 gene fusion was deposited with the American Type Culture Collection (Rockville, Md., U.S.) under the terms of the Budapest Treaty governing microbial deposits. The deposit was made on Apr. 5, 1994, and was given the Deposit Accession Number ATCC 69597.

Construction of the Second GST-SDI-1 Fusion

The second SDI fusion was obtained by amplifing the SDI-1 coding region of plasmid pcDSRαΔ-SDI-1 using the polymerase chain reaction, and primers having the sequence:

Primer 12614 (SEQ ID NO:12) GGAGGATCCATGTCAGAAC-CGGCT

Primer 12615 (SEQ ID NO:13) GCAGAATTCCTGTGGGCG-GATTAG

These primers amplify a polynucleotide containing residues 77–587 of SEQ ID NO:1. Primer 12614 has a BamHI site immediately upstream of the ATG translation initiation site. Primer 12615 includes 14 nucleotides downstream of the translational stop site, and includes a partial EcoRI site.

The amplified product was cleaved with BamHI and EcoRI and cloned into the above-described BamHI/EcoRI treated pGEX2T plasmid. The resulting plasmid contained an in-frame fusion linking codon 226 of the GST sequence to codon 1 of SDI-1.

The two protein fusions thus, differ only in that the first fusion contains a “hinge region” consisting of the amino acids:

SEQ ID NO:9 Pro-Arg-Gly-Asp-Pro-Pro-Ala whereas the second region does not contain any hinge region.

When the first and second GST-SDI-1 fusions were provided to young cells, the first fusion protein was found to be detectable within the cells whereas the second fusion protein was not detected within the cells. These observations indicated that whereas the first GST-SDI-1 fusion had the capacity to bind to cells and to be incorporated into recipient cells, the second GST-SDI-1 fusion lacked this capability. Consistent with these observations, of young cells that had been exposed to either the first protein fusion or the second protein fusion, only cells exposed to the first protein fusion exhibited quiescence.

EXAMPLE 21

Deletion Analysis of SDI-1 Protein

In order to investigate the functional domains of the SDI-1 protein, several genetic constructs were prepared in which the CMV promoter was used to drive transcription of fragments of the SDI-1 cDNA sequence.

Specifically, SDI-1 polynucleotides were constructed that lacked codons for amino acids: 24–29 (designated as: SDI-$1_{1-23;25-164}$); 30–35 (designated as: SDI-$1_{1-29;36-164}$); 42–47 (designated as: SDI-$1_{1-41;48-164}$); 53–58 (designated as: SDI-$1_{1-52;59-164}$); 66–71 (designated as: SDI-$1_{1-65;72-164}$); 72–164 (designated as: SDI-$1_{1-71}$). In addition, an SDI-1 polynucleotide was constructed that had been treated to remove a Stu-Tth fragment that included codons 16–52 (designated as: SDI-$1_{Stu-Tth}$). These constructs, and an intact SDI-1-encoding construct (designated as: SDI-$1_{1-164}$) and a CMV control vector were co-transfected into MDAH 041 cells along with a vector that expressed β-galactosidase driven by the CMV promoter. The percent of growth inhibition was determined relative to cells that had been co-transfected with the CMV-β-gal and CMV vector. Experiments were done in triplicate. The percent inhibition obtained for each SDI-1 polynucleotide is shown in Table 12.

TABLE 12

| Construct | Amino Acids Deleted | Expt. 1 | Expt. 2 | Expt. 3 | Avg. |
|---|---|---|---|---|---|
| CMV-vector | none | 98 | 100 | 98 | 99 |
| SDI-$1_{1-23; 25-164}$ | 24–29 | 93 | 93 | 92 | 93 |
| SDI-$1_{1-29; 36-164}$ | 30–35 | 93 | 91 | 83 | 89 |
| SDI-$1_{1-41; 48-164}$ | 42–47 | 66 | 76 | 75 | 72 |
| SDI-$1_{1-52; 59-164}$ | 53–58 | 40 | 46 | 57 | 48 |
| SDI-$1_{1-65; 72-164}$ | 66–71 | 88 | 81 | 88 | 86 |
| SDI-$1_{Stu-Tth}$ | Stu–Tth | 11 | 36 | 13 | 20 |
| SDI-$1_{1-164}$ | 72–164 | 90 | 98 | 98 | 95 |

The results indicate that deletion of amino acids 42–47 caused a decrease in the efficiency and extent of inhibition. Deletion of amino acids 53–58 showed a major decrease in efficiency and extent of inhibition. Deletion of the carboxy terminal portion of the SDI-1 molecule (amino acids 72–164) did not significantly affect the extent of inhibition. Thus, active domains of SDI-1 are present within a peptide fragment containing amino acids 1–71, and amino acids 42–47 and 53–58 contain active SDI-1 domains. In sum, active domains of SDI-1 are contained between amino acids 42–58 of the SDI-1 protein.

EXAMPLE 22

The Identification of an Immunoreactive 23 kD Protein

As expected, all of the above-described monoclonal and polyclonal antibodies were found to be capable of immunoprecipitating a 21 kD protein ("p21") corresponding to SDI-1. Analysis of the protein immunoprecipitated by these antibodies revealed that, unexpectedly, the antibodies also precipitated a 23 kD protein that was present in cellular extracts. The fact that all of the anti-SDI-1 antibodies tested precipitated this 23 kD protein ("p23") indicates that SDI-1 and the 23 kD protein are structurally related and share multiple epitopes. The fact that the 21 kD SDI-1 protein expressed from the above-described cDNA vectors is biologically active, indicates that the 23 kD protein exhibits the characteristics of an inactive, phosphorylated precursor of the active 21 kD SDI-1 protein.

In possessing such a precursor, SDI-1 resembles the Rb protein which has been found to exhibit multiple phosphorylation states that have molecular weights of 110–114 kD; the dephosphorylated form has a molecular weight of 110 kD (Lee, W.-H. et al., In: *Tumor Suppressor Genes*, Klein, G. (ed.), Marcel Dekker, Inc., New York, pp. 169–200 (1990)).

The identification of an inactivated, phosphorylated form of SDI-1 would indicate that the biological activity of SDI-1 is both positively regulated by p53 induction of transcription and negatively regulated by a cellular kinase. The identification of such kinase(s) can be readily determined by screening a cDNA library for members that upon expression produce proteins that can increase the phosphorylation of dephosphorylated p21 SDI-1. Such conversion can be analyzed by conducting western blots of p21–p23 immunoprecipitated protein. Since such enzymes inactivate p21 SDI-1, they confer a proliferative capacity to the cell, and can be identified as molecules that overcome SDI-1 induced senescence. Such molecules can be employed in the same manner as SDI-1 antisense nucleic acids. Similarly, enzymes that dephosphorylate the p23 protein can be identified by screening for polynucleotides that, upon expression, form a protein that can convert the p23 form into the p21 form. Western blot methods can be used to identify such molecules. Since such enzymes convert the p23 molecule into the active p21 form, such enzymes confer a quiescent or anti-proliferative capacity to the cells. Such molecules can be employed in the same manner as SDI-1 or SDI-1 encoding nucleic acids.

EXAMPLE 23

Characterization of SDI-1 Fragments

As discussed above, the control of cell proliferation in eukaryotes from yeast to humans involves the regulated synthesis, activation, and degradation of a family of cyclins that act as the regulatory subunits of protein kinases termed cyclin-dependent inases (Cdks). The cdks are necessary for the start of S phase and mitosis. The mechanism of inhibition of DNA synthesis by the protein SDI-1 involves inhibition of a series of Cdk kinase activities (e.g., cdk1–cdk6)). Indeed, in vivo SDI-1 protein has been found to associate with several of these cdk-cyclin complex by immunoprecipitation with antibodies against the various cyclin antibody (see, Xiong, H. et al., *Cell* 71:505–514 (1992)). These complexes are disrupted upon cellular transformation with some DNA tumor viruses (PCT Patent Application WO94/09135; Waga, S. et al., *Nature* 369:574–578 (1994)), confirming the above-stated mechanism by which oncogenic proteins alter the cell cycle of transformed cells. In addition, a recent report has confirmed the above-described relationship between SDI-1 and p53, and has shown that wild type p53 directly transactivates SDI-1 (Harper, J. W. et al., *Cell* 75:805–816. (1993); El-Deiry, W. S. et al., *Cell* 75:817–825 (1993); Xiong, Y. et al., *Nature* 366:701–704 (1993); Dulic, V. et al., *Cell* 76:1013–1023 (1994)), thus confirming that it is the downstream effector of p53. These, results confirm that SDI-1 is not only a negative regulator during normal cell proliferation but also a tumor suppresser factor during carcinogenesis.

In order to determine the region(s) of the SDI1 molecule that was required to inhibit DNA synthesis, a series of plasmids was constructed in which various SDI-1 cDNAs, expressed from the CMV promoter, were progressively truncated from the 3' end of the coding region. The capacity of the deletion mutants to inhibit kinase activity and/or DNA synthesis was evaluated using a transient expression assay and biding assay with cdk2.

The plasmids were constructed by digesting the plasmid pCMVβ with NotI to remove the *E. coli* β-galactosidase gene. This site was blunted with Klenow and an SpeI linker was inserted in order to create pCMVSpeI. The full-length SDI-1 cDNA was digested with BamHI and DraI and cloned into a pBluescript vector. An SpeI linker was litigated into the Hinc II site of this vector to create SpeI ends for nucleotides 1–686 of the SDII cDNA [plasmid pBSsdil (1–686)SpeI]. The SpeI-bounded fragment of SDI-1 from this vector was then ligated into the pCMVSpeI vector to create pCMVsdil(1–686), containing the full 164 amino acid coding region (SEQ ID NO:2) for the wild-type SDI-1 cDNA sequence. A series of mutants encoding carboxy-terminal truncated versions of SDI-1 were generated using restriction enzymes that have unique sites within the SDI-1 coding sequence.

HCA2, the above-described normal human diploid fibroblasts derived from neonatal foreskin were employed in the mutational analysis. These cells achieve 80 population doublings (PD) before entering senescence and were used at PD of 20–30 in all experiments. Each construct was tested for the ability to inhibit the initiation of DNA synthesis when transfected into HCA2. Following transfection, the deletion constructs were tested for protein production by immunofluorescence using an anti-HA monoclonal antibody (12CA5, obtained from BabCO).

Transfection of the full length SDI1 coding region resulted in a 90% decrease in the percentage of cells incorporating tritiated thymidine. A truncated SDI-1 encoding only the amino terminal 71 amino acids was as effective as the full length 164 amino acid protein in blocking entry into S phase whereas, a more severely truncated form encoding only the first 52 amino acids was completely inactive (Table 13). This indicated that a critical region for the DNA synthesis inhibitory activity was located between amino acids 52 and 71. Thus, peptide fragments of SDI-1 having amino acid residues 52–71 comprise mimetics of SDI-1 protein. Similarly, molecules that mimic a reactive side group of SDI-1$_{52-71}$ comprise mimetics of SDI-1. The role of the amino terminal portion of the protein in inhibiting entry into S phase was further clarified when a construct with a deletion in amino acids 16–52 (plasmid "1–164 (Δ16–52)") was also found to have lost all DNA synthesis inhibitory activity.

TABLE 13

| Amino Acid Residues Present In SDI-1 protein fragment | % Inhibition of DNA Synthesis Relative to Control |
|---|---|
| 1–164 | 88% |
| 1–123 | 90% |
| 1–82 | 92% |
| 1–71 | 85% |
| 1–52 | 0% |

TABLE 13-continued

| Amino Acid Residues Present In SDI-1 protein fragment | % Inhibition of DNA Synthesis Relative to Control |
|---|---|
| 1–16 | 0% |
| 1–164 (Δ16–52) | 0% |

To more finely map the DNA synthesis inhibitory region of the molecule, small internal deletions (in which only 4 to 6 amino acids were removed and 3 amino acids (Pro-Arg-Gly) were substituted) were introduced into the amino terminal portion of the molecule that the large deletion constructs had indicated was necessary for the inhibitory activity. Deletions of six amino acids were constructed in the SDI-1 cDNA at amino acids 24–29, 30–35, 42–47, 53–58 and 66–71. These constructs were fused in frame with DNA encoding a portion of the hemagluttinin (HA) molecule to provide an in-frame hemagluttinin (HA) tag at the C-terminus of the full length SDI-1 protein. The HA tag provided a unique antigen for immunostaining, and permitted a determination of whether the protein products were expressed and where they were localized within the cell. To ensure that the HA tag did not interfere with the DNA synthesis inhibitory activity of SDI-1, the cDNAs encoding either the full length (164 amino acid) or the truncated (amino acids 1–71) species were also fused to the HA sequence at the carboxy terminus. The HA tag sequence was introduced by the polymerase chain reaction (PCR) using the primers:

SEQ ID NO:14 TCTAGGCCTGTACGGAAGTG (splice site in pCMV vector)

SEQ ID NO:15 TAGGAATTCACTAGTCTAAGCG-TAATCTGGAACATCGTATGGGTAGGGCTTCCTCTTGGA

The inhibitory activity of these cDNAs was the same as that of a constructs without the HA tag. Another control construct was deleted in amino acids 16–52 and had no inhibitory activity whether it was tagged or not. Interestingly, and in further support of the importance of the integrity of the amino terminal region of the molecule in growth inhibition, cDNAs tagged with HA at the amino terminus had no growth inhibitory activity.

Deletions were then introduced into the protein-coding region of the SDI-1 cDNA in plasmid pCMVsdil(1–686)HA by PCR. The tag allowed one to ascertain that the wild-type and mutated proteins were expressed in cells transfected with the various constructs and also to determine the localization of the mutant protein.

The following primer sets were used to introduce the indicated deletions (Table 14):

TABLE 14

| Amino Acids Deleted | Seq Id No | Nucleotide Sequence |
|---|---|---|
| 24–29 | 16 | TTCGGCCCTCGAGGCCTGAGCCGCGACTGT |
|  | 17 | GCTCAGGCCTCGAGGGCCGAAGAGGCGGCG |
| 30–35 | 18 | TTAGCGCGCCTCGAGGCTGCTCGCTGTCCAC |
|  | 19 | CGAGCAGCCTCGAGGCGCGCTAATGGCGGGC |

TABLE 14-continued

| Amino Acids Deleted | Seq Id No | Nucleotide Sequence |
|---|---|---|
| 42–47 | 20 | GGCTGCCCTCGAGGCCGATGGAACTTCGAC |
|  | 21 | CCATCGGCCTCGAGGGCAGCCCGCCATTAG |
| 49–53 | 22 | CGTGAGCGACCCCGGGCGTCACCGAGACACCACTG |
|  | 23 | CTCGGTGACGCCCCGGGGTCGCTCACGGGCCTCCTG |
| 53–58 | 24 | TTCGACCCTCGAGGCCTGGAGGGTGACTTC |
|  | 25 | CTCCAGGCCTCGAGGGTCGAAGTTCCATCG |
| 58–61 | 26 | ACCGAGACATCCCGGGCCGACTTCGCCTGGGAGCGT |
|  | 27 | GGCGAAGTCGGCCCGGGATGTCTCGGTGACAAAGTC |
| 61–66 | 28 | CCACTGGAGCCCCGGGGCCGTGTGCGGGCCTTGGC |
|  | 29 | CCGCACACGGCCCCGGGGCTCCAGTGGTGTCTCGGT |
| 66–71 | 30 | GCCTGGCCTCGAGGCGGCCTGCCCAAGCTC |
|  | 31 | CAGGCCGCCTCGAGGCCAGGCGAAGTCACC |
| 72–77 | 32 | CGGGGCCTTCCCCGGGGCCTTCCCACGGGGCCCCGGCGAGG |
|  | 33 | CGTGGGAAGGCCCCGGGGAAGGCCCCGCACACGCTCCCAG |

Each primer was used with a primer hybridizing within the vector to amplify a portion of the SDI-1 plasmid, the amplified materials from two reactions were pooled and permitted to anneal. Single-stranded regions were filled in with polymerase, and the fragments were then ligated together to produce the desired covalently closed circular vectors. The use of SEQ ID NO: 26–27 replaced SDI-1 amino acids 58–61 with the tripeptide "Ser-Arg-Ala." The truncated constructs thus encoded the amino terminal end of the protein up to amino acid 123, 82, 71, 52 and 16, respectively. All constructs were sequenced to verify that the desired deletions had been made, that the integrity of the HA tag was intact and to confirm that no additional mutations had been introduced into the constructs.

HCA2 and MDAH 041 cells were co-transfected with pCMVβ-gal and plasmids carrying the above-described SDI-1 mutated DNA using calcium phosphate precipitation. The MDAH 041 cell line was derived from a Li-Fraumeni syndrome patient, and does not synthesize p53 sinced a frame shift mutation causes premature termination in the amino terminal region of the p53 molecule. MDAH041 were the cells of choice for these transfections because they do not express detectable levels of SDI1. They, therefore, provided a more sensitive assay for small changes in DNA synthesis inhibitory activity that might be expected in the case of these minimally deleted mutant constructs.

One μCi/ml tritiated thymidine was added to the culture medium 24 hours after transfection and the cells were incubated for an additional 36 hours. The cells were fixed, stained for β-galactosidase activity, and processed for autoradiography to determine the percentage of β-galactosidase positive cells that had synthesized DNA. Percent inhibition was determined relative to control cells co-transfected with the pCMV vector and pCMVB-gal.

Deletion of amino acids 53–58 was found to result in the greatest loss of DNA synthesis inhibitory activity (which was about 50% that of the full length cDNA). Two other deletions (of amino acids 42–47 and of amino acids 66–71 of SEQ ID NO:2) also caused a decrease in activity, although of lesser extent. Since the possibility existed that a particular construct that was actually minimally inhibitory might exhibit greater inhibition if a larger amount of DNA were transfected, the amount of plasmid DNA was reduced to 200 ng per transfection. The results of transfection experiments using this lower amount of DNA confirmed that the deletion of amino acids 42–47 and 66–71 of SEQ ID NO:2 did indeed result in a loss of inhibitory activity, and that the deletion of amino acids 53–58 of SEQ ID NO:2 resulted in a significant loss in ability to inhibit DNA synthesis. Deletions 24–29, 30–35 had activity similar to that of wild type at both DNA concentrations. These results indicate that the critical region of the protein product of SDI1 must lie between amino acids 42 and 71. They therefore support the conclusion that peptides having the sequence of SEQ ID NO:$2_{42\text{-}71}$ and non-peptide molecules that mimic a reactive side group of SEQ ID NO:$2_{42\text{-}71}$ comprise mimetics of SDI-1. In particular, a preferred mimetic has the amino acid sequence SEQ ID NO:$2_{49\text{-}77}$. A particularly preferred peptide mimetic has a sequence (SEQ ID NO:34): WNFDFXXXXPLEGXXXWXXVXXXXLPXXY. Such a mimetic may be formed using the above-described methods and primers having the sequences:

SEQ ID NO:35 CAGAATCACAAGCCACTCGAGGGTAAG-TACGAGTGGGAGCGTGTGCGGGCCTT

SEQ ID NO:36 CTTACCCTCGAGTGGCTTGTGATTCT-GAAAGTCGAAGTTCCATCGCTC

A preferred nonpeptide mimetic has residues that mimic reactive side groups of SEQ ID NO:34.

To determine whether the DNA synthesis inhibition caused by these mutants was occurring through inhibition of cdk kinases, the binding of in vitro translated deletion mutant proteins products with purified cdk2protein was examined. Thus, the various deletion mutants of SDI-1 were translated in reticulocyte lysates (Promega) using pBluescript based plasmids as transcription templates for the T7 RNA polymerase. For in vitro binding, 45 μl of the translation product was added to 500 μl binding buffer (50 mM Tris/HCl, pH 7.5, 120 mM NaCl, 2 mM EDTA, 0.1% NP-40, 1 mM NaF, 0.1 m.M sodium vanidate, 5 μg/ml leupeptin, 5 μg/ml soybean trypsin inhibitor, 5 μg/ml aprotinin) containing 1 ug cdk2 protein purified from a bacculovirus expression system. The mixture was gently rocked for 1 hour at 4° C. and then 7.5 μg anti-cdk2 rabbit polyclonal antibody was added. Mixing was continued for 1 hour at 4° C. The immunocomplex was absorbed by incubation with 40 μl protein G plus A beads for 2 hr. The matrices were then washed three times with 0.5 ml of binding buffer prior to electrophoresis and autoradiography.

All the mutant constructs produced protein which had a molecular weight of approximately 23 kD. To verify that the proteins were indeed deleted SDI-1 products, they were immunoprecipitated using CA5 (a monoclonal antibody against the HA tag sequence) and all successfully precipitated the antibody. The wild type protein SDI-1 and the three deletions, 24–29, 30–35, 72–77, bound cdk2 protein efficiently, suggesting that the DNA synthesis inhibitory activity of these constructs was the result of binding to cdk2. In contrast, the mutants, 42–47, 53–58, and 66–71, which had decreased inhibitory activity did not bind cdk2.

Immunohistochemistry

The intracellular localization of SDI-1 has been reported to be nuclear and there is a putative nuclear translocation signal at the 3' end of the coding region of the gene.

However, as indicated above, a C-terminus-truncated protein (SDI-1$_{1-71}$), which lacks this putative nuclear translocation signal was found to have the same inhibitory activity as the wild type protein (Table 13). In order to determine the localization of the protein products of the various deletion mutant constructs of SDI-1 following their transfection into the MDAH 041 cells, immunostaining of the HA tag was conducted.

For immunostaining, cells were seeded onto glass coverslips at about 50% confluent density, and allowed to adhere overnight before transfection. Following transfection cells were incubated at 37° C. for 24 hours, then washed twice with phosphate buffered saline (PBS) and fixed in freshly prepared formaldehyde solution [4% (wt/vol) paraformaldehyde in PBS] for 15 min at room temperature. The fixed cell's were then washed in PBS and incubated in 50 mM glycine in PBS at room temperature for 10 min. Cells were again washed with PBS and permeabilized by incubation in 0.2% Triton-X100 in PBS, at room temperature, for 10 min. After additional washings with PBS immunostaining was performed according to the direction of the ABC kit (source). The primary antibody (12CA5) was diluted 1:1000 in the buffer available in the kit.

The deleted, but still growth inhibitory proteins were found to localize to the nucleus whereas a high percentage of cells expressing the inactive or less active mutant proteins exhibited cytoplasmic staining. These data, along with the cdk binding results, strongly indicate that translocation of SDI-1 into the nucleus is dependent on the formation of a SDI-1 cyclin-cdk complex.

Thus, truncation of the C terminal region of SDI-1 revealed that SDI-1 molecules having amino acids 1–71 of SEQ ID NO:2 exhibited almost the same capacity to inhibit DNA synthesis as the full length SDI-1 protein (SEQ ID NO:2). Fine deletion analysis showed that the amino acids in region 42–71 of SEQ ID NO:2 were crucial for both kinase inhibition and DNA synthesis inhibition. This result was also confirmed by results which showed that SDI-1 molecules having deletions of the amino acids in region 42–71 of SEQ ID NO:2 exhibited no binding activity.

From immunohistochemical analysis, most of the active mutant protein was found to be localized in the nucleus. In contrast, SDI-1 mutants that lacked activity were found to be localized in the cytoplasm, indicating that translocation of SDI-1 into the nucleus is mainly depend upon the ability of making the complexes with cdk-cyclins rather than upon the existence of nuclear translocation-like sequences on the C-terminus of the SDI-1 protein. Because of the significance of region 42–71 of SEQ ID NO:2 on kinase inhibition and DNA synthesis inhibition, this region was studied in great detail. This analysis clearly indicated that homology regions (49–53 and 58–61 of SEQ ID NO:2) provided a new inhibitory motif among cdk inhibitors (such as SDI-1 and p27).

The above results clearly implicate the amino terminal region of the SDI-1 protein as the area involved in inhibiting DNA synthesis. The fine mapping studies implicate the region between amino acids 48–65 as critical for the negative growth effects of the gene. The data also demonstrate that when the gene product is involved in active inhibition it localizes to the nucleus of the cell and that inactive forms of the protein remain in the cytoplasm. With respect to this latter observation, it is of interest to note that a putative nuclear localization signal exists in the carboxy terminal region of the protein. Nonetheless, the deletion of amino acids 72–164 which eliminates this signal sequence, is fully capable of inhibiting DNA synthesis and is expressed in the nucleus. This indicates that some other molecule(s), perhaps the complexes of cyclins, cdks and PCNA with which SDI-1 associates, tranports the SDI-1 protein the nucleus.

EXAMPLE 24

Liposome-Mediated Intracellular Delivery of SDI Molecules

The ability of liposomes to deliver SDI-1 molecules into recipient cells was demonstrated using the B16 murine melanoma cell line. Purified protein (25 µg) (either SDI-1 obtained as described above, or bovine serum albumin (BSA), used as a control) was incubated with 10 µg of commercially obtained Lipofectamine™ liposomes (Life Technologies, Inc.) [formed from a 3:1 (w/w) mixture of the polycationic lipid DOSPA and the neutral lipid DOPE]. The protein was incubated in the presence of the Lipofectamine™ for 15 minutes at room temperature. The incubation occurred in a final volume of 0.2 ml serum-free medium. Such incubation is sufficient to permit the desired association of SDI-1 protein and liposome.

After the incubation period, the reaction mixture was added to 0.8 ml of B19 cells, resuspended in serum-free medium. After 4–5 hours, the Lipofectamine™/protein was removed and the cell incubation was continued. Cells were evaluated at various times for (1) the presence and location of internalized SDI-1 (identified through the use of labeled anti-SDI-1 antibody), (2) their capacity to mediate the incorporation of tritiated thymidine into their DNA, (3) cellular proliferation and (4) changes in cellular morphology. Cells for cell counts and tritiated thymidine incorporation were trypsinized at 24 hours post lipofection and replated at 2,500 cells per well of a 96-well plate (for thymidine incorporation analysis) or 10,000 cells per well of a 24-well plate for cell number determinations. The results of this experiment are shown in Table 15. Cells were evaluated for the presence and location of the delivered protein. After 3–4 hours, SDI-1 could be detected in the nuclei of ½ of the cells that had received SDI-1. After 9 hours, SDI-1 could be detected in the nuclei of ⅓ of such cells. After 48 hours, SDI-1 was no longer differentially observed in the nuclei of such cells which exhibited a gray staining over the entire cell. SDI-1 was not detectable 72 hours after liposome treatment. SDI-1 could not be detected (at any time) in cells that had received the BSA control (or buffer alone). After 48 hours, cells that had received SDI-1 appeared larger than control cells; after 72 hours, such cells were much larger than control cells. In Table 15, "Protein Delivered" indicates whether the liposomes were associated with the BSA control, or with the SDI-1 protein; "SDI-1 Staining" indicates the observed presence, frequency and location of SDI-1 in the recipient cells; "Cell Number" provided the titer of cells±experimental error; "$^3$H-Tdr Uptake" denotes the extent of incorporation of tritiated thymidine into the cell's DNA.

TABLE 15

| | | | | Ratio of SDI-1 Treated to BSA Treated | |
|---|---|---|---|---|---|
| Protein Delivered | Time (hr) | Cell Number | $^3$H-Tdr Uptake | Cell No. | $^3$H-Tdr Uptake |
| SDI-1 | 48 | 7820 ± 141 | 2134 ± 294 | 0.29 | 0.34 |
| BSA | 48 | 26540 ± 2828 | 6187 ± 211 | | |
| Buffer | 48 | 16040 ± 226 | 4057 ± 28 | | |
| SDI-1 | 72 | 23710 ± 1485 | 8765 ± 533 | 0.28 | 0.3 |
| BSA | 72 | 85760 | 28773 ± 810 | | |

The above experiment demonstrated the capacity of the liposomes to mediate the delivery of SDI-1 into the melanoma cells. The SDI-1 was active in such cells, since the number of cells and the capacity of the cells to take up tritiated thymidine was markedly reduced, in comparison to BSA treated cells. The experiment further demonstrated the ability of the delivered SDI-1 protein to migrate to the nuclei of the melanoma cells, and to persist for a therapeutically effective period of time within the nucleus. As indicated in Table 15, a significant change in gross cellular morphology occurred.

EXAMPLE 25

Enhanced Chemotherapeutic Ability of SDI Molecules in Combination with Conventional Antineoplastic Agents The mechanism of action of an antineoplastic plant alkaloid, CPT, was explored in order to demonstrate the chemotherapeutic ability of SDI molecules, and in particular, the value of combining the administration of a chemotherapeutic antineoplastic agent with that of an SDI molecule.

The plant alkaloid CPT and its derivatives have demonstrated high antiproliferative and toxic activity against a wide variety of human tumor cells in vitro and in vivo (Slichenmyer, W. J. et al., *J. Natl. Canc. Inst.* 85:271–291 (1993)). The mechanism of action; of these compounds involves stabilization of the covalent adducts formed between DNA and the nuclear enzyme topoisomerase I, an event that leads to interference with the breakage-reunion process of DNA strands (Liu, L. F., *Ann. Rev. Biochem.* 58:351–375 (1989); Potmesil, M. et al., *Canc. Res.* 54:1431–1439 (1994)). Other events associated with formation of DNA-topo I-CPT complexes include inhibition of DNA replication, induction of expression of early-response genes, induction of differentiation, and internucleosomal DNA fragmentation (Aller, P. et al., *Canc. Res.* 52.1245–1251 (1992)), a characteristic feature of programmed cell death, or apoptosis (Umansky, S. R., In: *Apoptosis: The Molecular Basis of Cell Death*, Tomei, L. D. et al. (eds), Cold Spring Harbor Laboratory, Cold Spring, N.Y., pp. 193–208 (1991); Wyllie, A. H. et al., In: *Oxford Textbook of Pathology: Principles of Pathology*, McGee, J. O. D. et al. (eds.), Oxford University Press, pp. 141–157 (1992)).

The CPT derivative, 9NC, elicits perturbations in the cell cycle in vitro that correlate with the ability of these cells to induce tumors when xenografted in nude mice (Pantazis, P. et al., *Canc. Res.* 53:1577–1582 (1993); Pantazis, P. et al., *Intl. J Canc.* 53:863–871 (1993); Pantazis, P. et al., *Canc. Res.* 54:771–776 (1994)). Specifically, 9NC-treated tumorigenic breast, ovarian and malignant melanocytes die by apoptosis while traversing the S phase of the cell cycle (Pantazis, P. et al., *Canc. Res.* 53:1577–1582 (1993); Pantazis, P. et al., *Intl. J Canc.* 53:863–871 (1993); Pantazis, P. et al., *Canc. Res.* 54:771–776 (1994)). Further, it appears that induction of apoptosis is irreversible in 9NC-treated tumorigenic cells, that is the 9NC-treated cells die by apoptosis without requiring continuous presence of 9NC (Pantazis, P. et al., *Canc. Res.* 53:1577–1582 (1993); Pantazis, P. et al., *Canc. Res.* 54:771–776 (1994)). In comparison, non-tumorigenic breast and ovarian epithelial cells treated with 9NC accumulate at the S-$G_2$ boundary of the cell cycle and only a small number of cells dying by apoptosis. The extent of cell accumulation in S-$G_2$ boundary correlates with the length of 9NC treatment and/or 9NC concentration (Pantazis, P. et al., *Canc. Res.* 53:1577–1582 (1993); Pantazis, P. et al., *Intl. J Canc.* 53:863–871 (1993); Pantazis, P. et al., *Canc. Res.* 54:771–776 (1994)). The sensitivity of malignant cells to CPT and its derivatives has been correlated positively with topo I synthesis and activity, and/or drug-induced accumulation of DNA-topo I-CPT complexes (Liu, L. F., *Ann. Rev. Biochem.* 58:351–375 (1989); Potmesil, M. et al., *Canc. Res.* 54:1431–1439 (1994)).

Recent reports suggest that CPT may alter p34$^{cdc2}$/cyclin B complex regulation in HeLa cells (Tsao, Y. P. et al., *Canc. Res.* 52:1823–1829 (1992)) and induce wild type p53 protein in ML-1 myeloid leukemia cells and in LNCaP prostatic adenocarcinoma cells (Nelson, W. G. et al., *Molec. Cell. Biol.* 14:1815–1823 (1994)). Significantly, both events appear to require active DNA synthesis. In this context, it has been reported that p53 may activate wild type p53-activated fragment 1, SDI-1 (sometimes referred to as Waf-1) El-Deiry, W. S. et al., *Cell* 75:805–816 (1993)). As indicated above, SDI-1 plays a critical role in the regulation of cell growth in tumor and senescent cells by inhibiting cyclin-dependent kinases and by subsequently interrupting the cell division process. To expand these observations and to gain insight into the molecular mechanism of CPT-induced cytostasis, the expression of SDI-1 was evaluated in non-tumorigenic cells and the results were correlated with those from studies examining the effects of CPT on cell proliferation and metabolic activity, DNA synthesis, and perturbation in the cell cycle.

A. Characteristic Effects of 9NC

The effect of 9NC (5 to 80 nM) on cell proliferation and DNA synthesis was evaluated by the Cell Proliferation Kit-XTT (Boehringer Mannheim Corp., IN), a non-radioactive, calorimetric ELISA assay which reflects mitochondrial dehydrogenase activity. The assay is based on the cleavage of the yellow tetrazolium salt XTT to form an orange formazan dye by dehydrogenase activity in active mitochondria. This conversion occurs only in living cells and correlates with their overall metabolic activity.

Human hepatoblastoma cells, HepG2 cells were obtained from the American Type Culture Collection and maintained in RPMI-1640 medium (GIBCO, Grand Island, N.Y.) supplemented with 10% fetal bovine serum (GIBCO), 100 units/ml of penicillin, 1009 μg/ml of streptomycin, 250 mg/ml of amphotericin (Sigma Chemical Co.), and 4 mM L-glutamine (GIBCO). The cell cultures were incubated at 37° C. in a humidified $CO_2$ (5%) atmosphere. The cell number in untreated and 9NC-treated cultures was determined with the aid of cell counter (Coulter Electric, Inc., Hialeah, Fla.) and cell viability was monitored by trypan blue dye exclusion.

9NC was semisynthesized from CPT and purified as described by Wani, M. C. et al. (*J. Med. Chem.* 29:2358–2363 (1986)). A fine suspension of 9NC (10 μM) was prepared in polyethylene glycol (PEG 400; Aldrich, Milwaukee, Wis.), divided into small aliquots and stored at −80° C. until used. 9NC was always added 24 h after cell plating.

DNA synthesis was measured by 5-bromo-2'-deoxyuridine (BrdU) incorporation into cellular DNA following 24 h and 72 h. treatment with 9NC using the Cell Proliferation Assay Kit-BrdU/ELISA (Boehringer Mannheim Corp.). Inhibition of DNA synthesis correlated with the length of 9NC treatment and the concentration of 9NC in the cell culture. Importantly, whereas only moderate suppression of metabolic activity (approximately 20% was observed in 72 h cultures treated with 20 nM of 9NC, at least four-fold decrease in DNA synthesis was demonstrated in corresponding cultures. Furthermore, in accordance with previous observation that active DNA synthesis is required for 9NC-induced cell arrest, a more prominent inhibitory effect of 9NC was observed in cell cultures treated with 9NC for 72 h as compared to cultures treated for 24 h.

The inhibition of DNA synthesis correlated with at least a two-fold decrease in cell numbers following 72 h treatment at 20 nM concentration of 9NC. This inhibitory effect was not associated with cell death as assessed by trypan blue dye exclusion. Taken together, these results indicate that low doses of 9NC (20 nM) induce significant inhibition of cell proliferation and DNA synthesis without affecting metabolic activity of the cells.

Phase contrast microscopy of 9NC-treated cells revealed an increased cell size (2 to 5-fold) with prominent cytoplasmic compartment. After 3 to days of treatment the morphology of the cells remained stable with very little change during the three to four week culture period. Overall, cells appeared to be healthy and metabolically active, and resembled the morphology of primary human hepatocytes grown on plastic surfaces. Virtually no cell proliferation was observed following removal of 9NC and the cells maintained a differentiated phenotype without growth.

In addition, attempts to subculture the cells failed. Such an absence of substantial growth is a characteristic feature of senescent and/or highly differentiated cells.

The proportions of cells in the different phases of the cell cycle were investigated by monitoring changes in the relative DNA content of the cells using flow cytometry following the methodology of Pantazis, P. et al. (*Canc. Res.* 53:1577–1582 (1993); *Intl. J Canc.* 53:863–871 (1993)). The changes in the DNA content were monitored both as a function of treatment period and drug concentration and compared with the results obtained in untreated cultures. Untreated cell cultures contain a relative high percentage of cell fraction in $G_2$, and a small but detectable fraction of hyperdiploid cells. Overall, little change occurred in DNA content at different incubation periods and equal distributions of the cells in $G_1$ and $G_2$ phases of the cycle were observed. A 24 h treatment of the cells with increasing concentrations of 9NC resulted in a decrease in $G_1$-fraction, and a concomitant increase in the S+$G_2$ and hyperdiploid fraction. The histogram area on the left side of the $G_2$-peak indicates that more cells are arrested in and/or traverse the S phase as the 9NC concentration increases. Higher 9NC concentrations resulted in hyperdiploid cells that had a DNA content which was less than that of hyperdiploid cells generated by the presence of lower 9NC concentrations.

Like 24 h-treated cultures, cultures treated for 72 h and 120 h contained hyperdiploid cell fractions with decreasing DNA content as the 9NC-concentration increases. Further, a relative increase in the apoptotic fraction was observed that correlates with increases in duration of drug treatment and concentration. Removal of 9NC from cultures treated for 48 h or more did not significantly alter the results described above indicating that the effects of 9NC on the cells were irreversible. It should be noted that the findings described in this section were observed in cells attached on the plastic substrate that were trypsin-removed for studies.

B. The Antineoplastic Characteristics of 9NC Are Attributable to Its Induction of SDI-1

The preceding experiments determined that 9NC at low doses (up to 20 nM) induced cytostatic effect without associated cell death by apoptosis or necrosis. Therefore, initial studies to evaluate the levels of SDI-1 were performed with low doses of 9NC. Total RNA was isolated from HepG2 cells treated with 5 nM and 20 nM 9NC for 72 h and the levels of SDI-1 mRNAs expression in cells were examined by Northern blot hybridization analysis. Whereas no or little change was observed in the expression of GAPDH, Northern analysis demonstrated a dose dependent increase in SDI-1 expression in 9NC-treated cells. The relative amount of SDI-1 mRNA in each sample was calculated as the ratio of SDI-1/GAPDH. At least 3-fold increase in SDI-1 expression was observed when 20 nM of 9NC was used.

Caffeine abolishes $G_2$ cell cycle checkpoint induced by DNA-damaging agents (Traganos, F. et al., *Canc. Res.* 53:4613–4618 (1993); Lau, C. C. et al., *Proc. Natl. Acad. Sci. (U.S.A.)* 79:2942–2946 (1982)). To assess the specificity of SDI-1 induction by 9NC, the levels of SDI-1 expressions were evaluated via Northern blot analysis after simultaneous addition of caffeine (1 mM) and 9NC. Whereas simultaneous addition of caffeine and 9NC abrogated the 9NC-dependent induction of SDI-1 expression, caffeine alone, or addition of caffeine after 24 h incubation with 9NC had no appreciable effect (of 9NC) on SDI-1 expression. Further, no differences in the levels of SDI-1 expression were observed between 24 h and 72 h treatment with 9NC, suggesting that induction of SDI-1 is an early event. Likewise, no changes in the levels of SDI-1 were observed following removal of 9NC. These results correlated with data obtained using flow cytometry by monitoring changes in the relative DNA content of the cells treated in the same conditions. To establish the kinetics of 9NC-induced upregulation of SDI-1 gene, the cells cultured for 24 h in control medium were treated with 20 nM of 9NC for 0.5 h, 1.5 h, 3 h, 6 h, 12 h, and 24 h respectively. Gene expression increased gradually and reached maximum at 24 h. Little changes were observed in corresponding 0 h, 3 h, 6 h, and 24 h control cell cultures, although, gradual decreases in the levels of SDI-1 expression through the duration of the experiment were noted.

Treatment of non-tumorigenic hepatoblastoma cells with 9NC thus resulted in a dose-dependent inhibition of cell proliferation and DNA synthesis. This effect correlated with at least a two-fold decrease in cell numbers in 9NC-treated cultures when compared to cell numbers in untreated cultures and was not associated with cell death as assessed by trypan blue dye exclusion when low doses of 9NC were used. Significantly, only a moderate decrease in overall metabolic activity (approximately 20%) was observed when 20 nM of 9NC was used despite at least 2-fold decrease in cell numbers and at least 4-fold decrease in DNA synthesis. This result indicates that 20 nM of 9NC induces a cytostatic state without affecting the metabolic activity of the cells. Light and electron microscopy further confirmed these findings and revealed enlarged cells with prominent cytoplasmic compartments containing generous lysosomes, mitochondria and accumulation of lipid in the cytoplasm.

The data thus indicate that low doses of 9NC induce a cytostatic rather than cytotoxic effect. Furthermore, both morphological and growth characteristics such as decreased capability to divide even after removal of 9NC resembles growth characteristics of cultured primary hepatocytes and the phenomenon of cellular senescence. These results are consistent with recently published data that described CPT-induced differentiation and stimulation of the expression of differentiation-related genes in U-937 cells (Aller, P. et al., Canc. Res. 52:1245–1251 (1992)). Flow cytometry revealed that the majority of the cells were arrested in the $G_2$ phase of the cell cycle. Taken together, these results indicate that 9NC at low concentrations causes cell arrest in a hepatoblastoma cells in $G_2$ phase and induces morphologic and growth features of highly differentiated or senescent cells.

In sum, non-tumorigenic immortal hepatoblastoma cells, HepG2, arrested at the $G_2$ phase of the cell cycle by 9NC, exhibited morphologic, ultrastructural and growth characteristics of senescent cells and overexpressed SDI-1 mRNA. Induction of SDI-1 by 9NC demonstrates that SDI-1 can be overexpressed in the $G_2$ phase of the cell cycle and confirms the conclusion that genes upregulated in senescent cells are also induced in arrested cancer cells. The results further demonstrated that at least a three-fold increase in SDI-1 gene expression was induced by 20 nM 9NC in hepatoblastoma cells. Since a consequence of 9NC administration is the production of SDI-1, the co-administration of SDI-1 and 9NC would permit a therapeutic effect to be obtained using lower doses of 9NC. Thus, the results of the above example support the conclusion that the use of SDI molecules in combination with "standard" antineoplastic agents can increase the effectiveness of anticancer therapy.

EXAMPLE 26

Enhanced Chemotherapeutic Ability of SDI Molecules in Combination with Conventional Antineoplastic Agents SDI-1 appears to prevent the inactivation by phosphorylation of the rb gene product (pRb). One aspect of the present invention concerns the recognition that SDI-1 inhibits the activity of E2F, a growth-stimulatory transcription factor that is negatively regulated by unphosphorylated pRb.

pRb is underphosphorylated in quiescent cells, where it is thought to suppress growth. As cells approach S phase, pRb is progressively phosphorylated, at least in part by cdks, which inactivate its growth suppressive properties (Buchkovich, K. et al., Cell 58:1097–1105 (1989); Chen, P. L. et al., Cell 58:1193–1198 (1989); Mihara, K. et al., Science 246:1300–1303 (1989); DeCaprio, J. A. et al., Proc. Natl. Acad. Sci. (U.S.A.) 89:1795–1798 (1992)). Underphosphorylated pRb binds a variety of proteins. One of these is E2F (Chellappan, S. P. et al., Cell 65:1053–1061 (1991); Helin, K. et al., Cell 70:337–350 (1992); Kaelin, W. G. et al., Cell 70:351–364 (1992); Shan, B. et al., Molec. Cell. Biol. 12:5620–5631 (1992)), a transcription factor whose activity is required for the expression of several genes at the G1/S boundary (Farnham, P. J. et al., Biochim. Biophys. Acta 1155:125–131 (1993)). pRb phosphorylation in the late G1 is believed to release E2F, which is needed for activity). Thus, entry into S phase appears to be regulated by the sequential activation of cdks which lead to a progressive phosphorylation of pRb and release of E2F, which, in turn, stimulates the transcription of genes needed for DNA replication and mediates entry into S phase.

The effect of the human SDI-1 on transcription driven by two E2F-responsive promoters was determined. Proliferating A31 cells were transfected with an SDI-1 expression vector in which the SDI-1 cDNA was driven by the strong constitutive cytomegalovirus early promoter (CMV) together with a reporter vector in which the chloramphenicol acetyltransferase (CAT) gene was driven by either the hamster dihydrofolate reductase (DHFR) promoter or the human cdc2 promoter (cdc2-CAT). A31 cells are Balb/c murine 3T3 fibroblasts whose origin and growth properties have been described (Lu, K. et al., Molec. Cell. Biol. 9:3411–3417 (1989); Dimri, G. P et al., J. Biol. Chem. 269:16180–16186 (1994), herein incorporated by reference). Cells were transfected with 2 µg of expression vectors, reporters vectors (for transactivation) and the CMV-β-gal identification/normalization vector using Lipofectamine (Gibco-BRL), as described by Dimri, G. P et al. (J. Biol. Chem. 269:16180–16186 (1994), herein incorporated by reference), The vector backbone was added to the mixture as needed to equalize the amount of transfected DNA. Seventy-two hours later, the cells were lysed and assayed for chloramphenicol acetyl transferase (CAT) and β-galactosidase activity. Both DHFR and cdc2 were expressed by proliferating cells, largely due to E2F-mediated transcription that is dependent on E2F binding sites in the 5' regulatory regions of these genes (Slansky, J. E. et al., Molec. Cell. Biol. 13:1610–1618 (1993); Dalton, S., EMBO J. 11:1797–1804 (1992)).

The SDI-1 expression vector, CMV-SDI-1, but not the control vector, suppressed CAT activity driven by either the DHFR or cdc2 promoter (Table 16). CMV-SDI-1 was maximally inhibitory at above 2 µg of DNA under the assay conditions used. CAT activity in Table 16 is reported in counts per minute, normalized to the β-galactosidase activity. At this concentration, CMV-SDI-1 inhibited the DHFR promoter, which contains two strong E2F binding sites (Slansky, J. E. et al., Molec. Cell. Biol. 13:1610–1618 (1993)), somewhat more strongly than the cdc2 promoter, which contains a single E2F binding site (Dalton, S., EMBO J. 11:1797–1804 (1992)) (50–70% inhibition vs 40–50% inhibition). This difference in sensitivity is consistent with the finding that the DHFR promoter is somewhat more sensitive than the cdc2 promoter to stimulation by E2F1, a component of E2F (Dimri, G. P et al., J. Biol. Chem. 269:16180–16186 (1994)). At the concentrations used here, CMV-SDI-1 inhibited DHFR-CAT and cdc2-CAT expression to approximately the same extent that it inhibited DNA replication.

TABLE 16

| Report Vector | Expression Vector cDNA | Normalized CAT Activity | % Activity | % Inhibition |
|---|---|---|---|---|
| DHFR-CAT | None* | 9462 | 100 | 0 |
| | SDI-1 | 9155 | 97 | 4 |
| | 0.2 µg | | | |
| | 1.0 | 8196 | 87 | 13 |
| | 2.0 | 2613 | 28 | 72 |
| | 4.0 | 1757 | 19 | 81 |
| cdc2-CAT | None* | 3304 | 100 | 0 |
| | SDI-1 | 1664 | 50 | 50 |
| | 1.0 µg | | | |
| | 2.0 | 2000 | 60 | 40 |
| | 4.0 | 2008 | 61 | 39 |
| SV-CAT | None* | 3620 | 100 | 0 |
| | SDI-1 | 3743 | 103 | 0 |
| | 1.0 µg | | | |
| | 2.0 | 3828 | 106 | 0 |
| | 4.0 | 3366 | 93 | 7 |

TABLE 16-continued

| Report Vector | Expression Vector cDNA | Normalized CAT Activity | % Activity | % Inhibition |
|---|---|---|---|---|
| fos-CAT | None* | 16927 | 100 | 0 |
| | SDI-1 2.0 µg | 16273 | 96 | 4 |

In sharp contrast to the response of the DHFR and cdc2 promoters, CMV-SDI-1 had little or no effect on reporter activity driven by either the SV 40 early promoter (SV-CAT or the c-fos promoter (fos-CAT) (Table 16). Neither the SV40 early genes nor c-fos has been reported to be E2F-responsive.

To more critically ascertain whether the inhibition of transcription by SDI-1 was E2F-dependent, three E2F binding sites were inserted into the SV40 early promoter and the effect of CMV-SDI-1 on CAT activity driven by this modified promoter (SV/E2F) was determined. To construct SV/E2F-CAT and SV/E2Fm-CAT, three copies of the sequence encompassing the E2F binding site in the dihydrofolate, reductase promoter was inserted into the Bgl II site that is just upstream of the SV40 early promoter in SV-CAT. The E2F binding site was wild-type in SV/E2F-CAT, and carried a CGCGCC to CGATCC mutation within the 12 residue long binding site (Slansky, J. E. et al., *Molec. Cell. Biol.* 13:1610–1618 (1993); Nevins, J. R., *Science* 258:424–429 (1992)).

CMV-SDI-1 (2 µg) suppressed the activity of SV/E2F-CAT to about the same extent that it inhibited the activity of DHFR-CAT. By contrast, mutant E2F binding sites, similarly inserted into the SV40 promoter (SV/E2Fm-CAT), did not confer SDI-1-suppressible CAT activity. Thus SDI-1 can inhibit transcription that is dependent on a wild-type, but not mutant, E2F site.

Cotransfection of an E2F1 expression vector (CMV-E2F1) with CMV-SDI-1 almost completely reversed the inhibition of DNA synthesis. SDI-1-mediated suppression of DNA synthesis was also reversed by an SV40 large T antigen expression vector. SV 40 T antigen binds and inactivates both the p53 and pRb tumor suppressor proteins, as well as the pRb-related proteins p107 and p130 (Fanning, E. et al., *Ann. Rev. Biochem.* 61:55–85 (1992)). A mutant T antigen carrying a small deletion that inactivates the p53-binding function (T[p]) was about 70% as effective as wild-type T antigen in reversing growth inhibition by SDI-1. The T[p] expression vector was constructed by inserting into CMV1 the BamHI-Bgl II fragment of Td1434–444, which contains the SV40 early region bearing the deletion corresponding to amino acids 434–444 in large T antigen.

By contrast, a mutant T antigen carrying a point mutation that inactivated the pRb and pRb-related protein binding function (T[K]) failed to reverse SDI-1-mediated suppression of DNA synthesis. In addition to reversing SDI-1's antiproliferative effects, CMV-E2F1 also reversed SDI-1-dependent inhibition of E2F transaction, as judged by its effect on DHFR-CAT and cdc2-CAT expression. Taken together, the results indicate that SDI-1 is capable of inhibiting E2F transactivation activity, and that this inhibition appears to be important for SDI-1's antiproliferative effects.

To further demonstrate the conclusion that the ability of SDI-1 to inhibit growth was closely linked to its ability to inhibit E2F-dependent transcription, the inhibitory properties of several SDI-1 mutants were examined. These mutants included a naturally occurring SDI-1 variant (p21pm) in which the serine at amino acid 31 was replaced by an arginine. This polymorphism has been detected in approximately 10% of normal human cells thus far examined, and appears to result in a slight reduction in the antiproliferative properties of SDI-1 (Table 17). A SDI-1 expression vector for this allele (CMV-p21pm) was compared with CMV-SDI-1 for ability to inhibit DNA synthesis and E2F-mediated transactivation in proliferating A31 cells. Both SDI-1 and the SDI-1 polymorphic protein suppressed growth and transcription driven by the cdc2 and SV/E2F promoters, but not the SV/E2Fm promoter. In all cases, however, CMV-SDI-1pm was 5–10% less effective than CMV-SDI-1 at inhibiting both DNA synthesis and E2F-mediated transaction (Table 17).

Several SDI-1 deletion mutants were also tested for their ability to inhibit DNA synthesis and DHFR-driven CAT activity. Expression vectors encoding SDI-1 proteins carrying deletions in amino acids 24 to 29, 53 to 58, or 17 to 52 were introduced into proliferating A31 cells, and their ability to inhibit DNA synthesis and DHFR-driven CAT activity were compared. There was a good correspondence between the extents of deletion and the mutants' relative abilities to inhibit DNA synthesis and DHFR-driven transcription. In Table 17, "% LN" denotes the percentage of transfected (β-galactosidase positive) cells with radiolabeled nuclei; "SDI-1" denotes an expression vector that expresses the wild-type SDI-1 protein, "p21pm" denotes an expression vector that expresses the above-discussed SDI-1 polymorphic mutant protein.

TABLE 17

| Reporter Vector | Expression Vector cDNA | Transcription (Normalized) | | DNA Synthesis | |
|---|---|---|---|---|---|
| | | % Activity | % Inhibition | % LN | % Inhibition |
| SV/E2F-CAT | None | 100 | 0 | 68 | 0 |
| | SDI-1 | 50 | 50 | 17 | 75 |
| | p21pm | 53 | 47 | 25 | 63 |
| SV/E2Fm-CAT | None | 100 | 0 | | |
| | SDI-1 | 93 | 7 | | |
| | p21pm | 82 | 18 | | |
| cdc2-CAT | None | 100 | 0 | | |
| | SDI-1 | 52 | 48 | | |
| | p21pm | 62 | 38 | | |

Because SDI-1 inhibits the protein kinases that phosphorylate pRb, and unphosphorylated pRb is believed to negatively regulate E2F activity (Nevins, J. R., *Science* 258:424–429 (1992)), pRb is presumed to be a central mediator of SDI-1's effects. Since A31 cells express a normal Rb gene, the ability of SDI-1 to inhibit E2F activity, and possibly growth, in tumor cells that lack a functional pRb was tested. For this purpose, the ability of SDI-1 to inhibit DNA synthesis and E2F activity in C33A (HTB 31), a human cervical carcinoma cell line that does not express a functional pRb by virtue of a frameshift mutation was evaluated. C33A cells were obtained from the American Type Culture Collection (Rockville, Md.).

C33A cells were found to be clearly sensitive to both the growth inhibitory and transcription inhibitory properties of SDI-1. Indeed, SDI-1 had a substantial antiproliferative effect on C33A cells, although they were somewhat less sensitive than A31 cells (40–50% inhibition vs 65–75% inhibition). By contrast, C33A and A31 cells were equally sensitive to SDI-1 inhibition of E2F activity. Thus, CMV-SDI-1 reduced DHFR-, cdc2- and SV/E2F-driven CAT activity to approximately equal extents in C33A and A31 cells. As expected CMV-SDI-1 had no effect on SV/E2Fm-driven CAT activity in either cell line. Taken together, the results demonstrate that SDI-1 can act to inhibit DNA synthesis and E2F activity through cellular targets other than pRb.

E2F binding sites are occupied by protein complexes, whose composition—at least by in vitro analyses—depend on the cellular growth state and stage of the cell cycle (Chellappan, S. P. et al., *Cell* 65:1053–1061 (1991); Nevins, J. R., *Science* 258:424–429 (1992); Farnham, P. J. et al., *Biochim. Biophys. Acta* 1155:125–131 (1993)). To determine which if any of these complexes might be a target for SDI-1, the effect of recombinant SDI-1 protein on DNA-protein complexes that associate with an E2F binding site in vitro was determined Nuclear extracts from quiescent cells contain several E2F complexes, despite the fact that E2F1, the cell cycle regulated component of E2F that is a target for pRb binding (Helin, K. et al., *Cell* 70:337–350 (1992); Kaelin, W. G. et al., *Cell* 70:351–364 (1992); Shan, B. et al., *Molec. Cell. Biol.* 12:5620–5631 (1992)), is not expressed (Shan, B. et al., *Molec. Cell. Biol.* 12:5620–5631 (1992); Slansky, J. E. et al., *Molec. Cell. Biol.* 13:1610–1618 (1993); Dimri, G. P et al., *J. Biol. Chem.* 269:16180–16186 (1994)). Quiescent cell extracts contain only low levels of "free" E2F, the presumed active form of E2F, but also very little E2F in association with pRb. Rather, quiescent cells contain E2F components in association with the pRb-related protein p107, and/or in association with p130 (Cobrinik et al., *Genes Devel* 7:2392–2404 (1993)). None of the E2F complexes present in quiescent cell extracts were found to be affected the addition of SDI-1 protein. In addition, none of the E2F complexes in quiescent cells were disrupted or supershifted by a SDI-1 antibody.

E2F-1 is induced a few hours prior to S phase (Shan, B. et al., *Molec. Cell. Biol.* 12:5620–5631 (1992); Slansky, J. E. et al., *Molec. Cell. Biol.* 13:1610–1618 (1993); Dimri, G. P et al., *J. Biol. Chem.* 269:16180–16186 (1994)) at about which time nuclear extracts from cells in mid to late G1 contain increased levels of free E2F, E2F in association with pRb, and E2F in association with p107, cdk2 and cyclin E (mid-late G1-early S). Of the complexes present in extracts from cells in late G1, only the E2F/p107/cdk/cyclin complexes were disrupted by recombinant SDI-1.

In quiescent cells, SDI-1 expression is high; E2F activity is low, with low levels of free E2F and E2F/p107/cdk/cyc complex. Mitogens suppress SDI-1 expression, leading to induction of E2F1 mRNA; this in turn induces free E2F, E2F/p107/cdk/cycE, and ultimately DNA synthesis. The finding that SDI-1 does not affect complex formation in G0 may reflect either that, in G0, E2F/p107 is not associated with cyclin/cdk. Alternatively, the finding may indicate that all E2F activity in G0 is associated with p130, and that SDI-1 has no effect on p130/E2F with or without cyclins.

Antisense SDI-1 artificially lowers SDI-1 expression in Q cells, and this leads to induction of E2F1 expression, free E2F, E2F/p107/cdk/cyc complex, and DNA synthesis. Growing cells express high levels of SDI-1, E2F1 expression, E2F/p107/cdk/cyc complex, and E2F activity. Induction of SDI-1, as might occur in responded to damage or elevated p53, disrupts E2F/p107/cdk/cyc complexes, which may mediate rapid growth arrest. If SDI-1 levels remain high, E2F1 expression declines, followed by a decline in free E2F and establishment of quiescent state.

As indicated by the above experiments, SDI-1 was found to inhibit E2F-mediated transcription activation. Moreover, SDI-1 mutants that failed to inhibit E2F also failed to inhibit DNA replication, and E2F-1, the cell cycle regulated component of E2F, antagonized the inhibition of transaction and DNA replication by SDI-1. However, pRb was not essential for these effects: SDI-1 inhibited growth and E2F activity in pRb-deficient cells. SDI-1 selectively disrupted a DNA binding complex containing E2F, cdk2, cyclin E or A and the Rb-related protein p107 in vitro (and in cells, and in cells, SDI-1 downregulated the level of E2F1 mRNA). We conclude that SDI-1 inhibits growth at least in part by suppressing E2F activity, possibly by disrupting the E2F/cdk2/p107 complex to elicit a rapid growth arrest and, ultimately, causing a deficiency of E2F-1. The results also indicate pRb is not essential for growth suppression by SDI-1, and suggest that in Rb-deficient cells SDI-1 may act through pRb-related proteins such as p107 or p130.

The recognition of molecular mechanisms through which SDI-1 mediates its biological activity permits, the use of directed screening assays to identify mimetics and antagonists of SDI-1 and its binding partners. Such assays can be used to produce SDI molecules having more desired characteristics.

EXAMPLE 27

In vivo Ability to Deliver SDI-1 to Skin Cells: Ability of SDI-1 to Inhibit Hair Growth As indicated above, SDI-1 is capable of inhibiting cellular proliferation and of establishing a quiescent state when delivered to actively proliferating recipient cells. Conversely, the administration of an inhibitor of SDI-1 permits a quiescent cell to regain its proliferative capacity.

The ability of SDI-1 to prevent hair loss was determined by demonstrating the capacity of SDI-1 to be delivered to hair follicles and to mediate a change in the capacity of the hair follicles to form hair.

Hair growth was assayed using the Dermatek™ histoculture in vitro histoculture assay system (AntiCancer, San Diego, Calif.). The Dermatek™ histoculture assay system is described by Li, L. et al. (*In Vitro Cell Devel Biol.* 28A:479–481 (1992); *In Vitro Cell Devel Biol.* 28A:695–698 (1992), both references herein incorporated by reference).

The Dermatek™ system exploits the fact that the activity of hair follicles is governed by a continuous cycle composed of a telogen (no hair growth) phase, an anagen (hair growth phase) phase and a catagen phase, and a return to the telogen phase. Mice that are in the telogen phase are induced to enter the anagen phase by depilation. Since, in mice, all truncal melanocytes are confined to the hair follicles, the production of melanin is strictly coupled to the anagen phase of the follicular cycle. Thus, depilation permits one to synchronize the follicle cycle. By employing mice such as C57Bl6, the progression of the hair follicle into the anagen phase can be followed by monitoring the production of melanin. Thus, the skin of such mice change from white/pink (telogen), to gray (mid-anagen), to black (late anagen). In the Dermatek™ assay, biopsies of skin are suspended on collagen-containing sponge-gel supports and cultured under in vivo-like conditions. The assay thus provides large numbers of homogeneous, mature follicles of defined hair stage.

For such assays, SDI-1, prepared as described above, was incorporated (via sonication) into liposomes having a com position of phosphatidylcholine, cholesterol, and phosphatidylethanolamine (ratio of 5:3:2). The ratio of lipid to SDI-1 was 10:1.

C57BI6 mice were depilated with wax/rosin as described by Li, L. et al. (*In Vitro Cell Devel Biol.* 28A:479–481 (1992); *In Vitro Cell Devel Biol.* 28A:695–698 (1992)). Four days after depilation, 4 pieces of 4 mm acu-punched skin tissues were removed and placed into organ culture. Twenty-four hours later, a liposome preparation containing either 100 µg/ml, 50 µg/ml, or 30 µg/ml of SDI-1 was topically administered to the skin cultures. The ability of SDI-1 to inhibit melanin production and hair growth in skin areas that had received the liposome preparation was determined by photo-microscopy 24 and 48 hours after SDI-1 liposome administration.

Significant hair follicle development and melanin production was evident in the skin of the depilated animals 5 days after depilation. Melanin production was intense. Control animals evaluated 24 hours later exhibited even more substantial melanin production and hair follicle growth. Both the number and size of melanin-producing foci had increased. Melanin production appeared as intense foci adjacent to regions of less intense, more diffuse areas of pigmentation.

Twenty-four hours after being treated with the liposome preparation containing 30 µg/ml of SDI-1, the skin of C57BI6 mice exhibited a significant reduction in both the number of developing hair follicles and the extent of melanin production. Melanin production was not as intense as in the control animals, and some foci exhibited only minimal pigmentation.

C57BI6 mouse skin treated with the liposome preparation containing 50 µg/ml of SDI-1 exhibited (24 hours after treatment) an even more substantial decrease in follicle growth and melanin production than that exhibited by the mouse skin treated with 30 µg/ml SDI-1 liposomes. Only a small number of foci appeared to have any intensity of melanin production, and the exhibited production of such foci was markedly less than those of control or 30 µg/ml SDI treated animals. The majority of foci exhibited little or no follicle development, and minimal and diffuse melanin production.

A still greater decrease in follicle growth and melanin production was observed in the skin of C57BI6 mice treated with 100 µg/ml SDI-1 liposomes at 24 hours post treatment.

The responses were also found to persist over time. Thus, whereas control mice at day 7 (i.e. 48 hours after the experimental mice had received SDI-1 liposomes) exhibited pronounced intense melanin production and hair follicle development, mice that had received SDI-1 liposomes exhibited continued inhibition of melanin production and follicle growth.

Mouse skin that had received the liposome preparation containing 30 µg/ml of SDI-1, skin after 48 hours exhibited increased melanin production compared to 24 hours, thus indicating the transiency of the hair growth inhibition over time. Although the extent of melanin production after 48 hours for such mouse skin exceeded that observed after 24 hours, the amount of melanin produced was substantially less than that observed in the untreated controls.

Such transiency was not observed in mouse skin that had been treated with liposome preparations containing either 50 µg/ml of SDI-1 or 100 µg/ml of SDI-1, thus indicating that the levels of SDI-1 in the hair follicles of such animals had not yet decayed below a therapeutic level, or that the administration had a prolonged effect.

The experiment demonstrates several aspects of the present invention:

(1) It demonstrates the capacity to deliver SDI-1 to skin follicles via a liposome formulation.

(2) It demonstrates that the delivered SDI-1 was biologically active, and hence that the it was not merely delivered to cells, in vivo, but was moreover capable of migrating intracellularly to its appropriate target site.

(3) The experiment demonstrates the ability of SDI-1 to cause the actively proliferating cells of hair follicles to cease (in a dose responsive manner) producing products (hair and melanin) that are associated with such proliferation. Thus, the experiment demonstrates an in vivo ability of SDI-1 to induce quiescence in proliferating cells.

(4) The experiment indicates that SDI-1 would be an effective agent in the treatment of hair loss induced by chemotherapy. As indicated above, alopecia (hair loss) is an undesired side effect of chemotherapy. The hair loss reflects the damage or death of hair follicles due to the presence of the chemotherapeutic agent. The eventual restoration of hair production in patients who have undergone chemotherapy evidences the repair or replacement of such follicles. Since the above-described experiment demonstrates the ability of SDI-1 to induce the cells of hair follicles into a quiescent state, the administration of SDI-1 to the hair follicles of patients who are to undergo chemotherapy would be expected to minimize or prevent hair loss due to such chemotherapy. Such administration would be expected to transiently prevent new hair growth (as indicated in the experiment) while simultaneously inhibiting DNA synthesis. The inhibition of DNA synthesis permits DNA repair processes to repair or rescue cells of the hair follicles that have been damaged by the chemotherapeutic agent. Upon recovery from the SDI-1 administration, the cells of the hair follicles (which are also no longer being exposed to the chemotherapeutic agent) reinitiate the synthesis of hair. Thus, overall, the patient experiences a transient cessation of new hair growth, but does not experience the hair loss previously associated with such chemotherapy.

(5) The experiment demonstrates that the administration of SDI-1 provides a reversible transient therapy whose therapeutic effect may be sustained by either increasing the dose of administered SDI-1, or by providing additional doses.

(6) The experiment demonstrates the capacity of SDI-1 to retard and/or transiently prevent hair growth, and thus indicates the ability of SDI-1 to be used to prevent undesired (facial, leg, etc.) hair growth or to treat hirsutism.

While the invention has been described in connection with specific embodiments thereof, it will be understood that it is capable of further modifications and this Application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. An antibody to a senescent cell-derived inhibitor, SDI-1, which antibody specifically binds to an SDI-1 fusion protein, which protein comprises (i) an SDI-1 protein or fragment thereof and (ii) a hinge region of at least the amino acids depicted in SEQ ID NO:9, which fusion protein is capable of inhibiting DNA synthesis in a recipient cell.

2. An antibody to a senescent cell-derived inhibitor, SDI-1, which antibody specifically binds to an SDI-1 fusion protein having the coding sequence of the cDNA insert of the plasmid contained in ATCC Deposit 69597.

3. An antibody to a senescent cell-derived inhibitor, SDI-1, which antibody specifically binds to an SDI-1 fusion protein comprising the amino acid sequence depicted in SEQ ID NO:11.

4. An antibody to a senescent cell-derived inhibitor, SDI-1, which antibody specifically binds to the SDI-1 protein encoded by SEQ ID NO: 2.

5. An antibody to a senescent cell-derived inhibitor, SDI-1, which antibody specifically binds to an SDI-1 protein having the coding sequence of the cDNA insert of the plasmid contained in ATCC Deposit 69081.

6. A monoclonal antibody to a senescent cell-derived inhibitor, SDI-1, which antibody specifically binds to a protein or a fusion protein comprising at least the amino acid sequence of SEQ ID NO: 2.

7. A monoclonal antibody to a senescent cell-derived inhibitor, SDI-1, which antibody specifically binds to:

a) a protein comprising the coding sequence of the cDNA insert of the plasmid contained in ATCC Deposit 69081;

b) a fusion protein comprising at least the coding sequence of the cDNA insert of the plasmid contained in ATCC Deposit 69081;

c) a fusion protein consisting of the amino acid sequence depicted in SEQ ID No. 11; or d) a fusion protein consisting of the coding sequence of the cDNA insert of the plasmid contained in ATCC Deposit 69597.

8. An antibody to a senescent cell-derived inhibitor, SDI-1, which specifically binds to an SDI-1 fragment comprising in the fragment at least amino acids 1 to 71, 1 to 82, 1 to 123, 16 to 52, 42 to 47, 42 to 58, 42 to 71, 48 to 65, 49 to 53, 52 to 71, 53 to 58 58 to 61, or 66 to 71 as depicted in SEQ ID NO: 2.

9. The SDI-1 antibody of claim 8, wherein the SDI-1 fragment comprises in the fragment amino acids 42 to 47, 42 to 58, 52 to 71, or 53 to 58.

10. A continuous cell line prepared by fusing a tumor cell with an antibody-producing cell derived from a mouse immunized with a protein which is a senescent cell-derived inhibitor, SDI-1, or a fragment thereof.

11. A continuous cell line which produces a monoclonal antibody specific for a protein which is a senescent cell derived inhibitor, SDI-1, or a fragment thereof, wherein the continuous cell line is prepared by fusing a myeloma or plasmacytoma cell with a splenic leukocyte or splenocyte derived from a mouse immunized with an SDI-1 protein or fragment thereof.

12. The cell line of claim 11, wherein the cell line is prepared by fusing the myeloma cell with the splenic leukocyte.

13. The cell line of claim 11, wherein the cell line is prepared by fusing the myeloma cell with the splenocyte.

14. The cell line of claim 11, wherein the cell line is prepared by fusing the plasmacytoma cell with the splenic leukocyte.

15. The continuous cell line of claim 11, wherein the hybridoma cell line is prepared by fusing the plasmacytoma cell with the splenocyte.

16. A pharmaceutical composition which comprises the SDI-1 antibody of claim 1, 2, 3, 4, 5, 8 or 9.

17. A pharmaceutical composition which comprises the SDI-1 monoclonal antibody of claim 6 or 7.

18. A process for detecting the presence of a protein which is a senescent cell-derived inhibitor, SDI-1, or a fragment thereof, which process comprises the steps of:

(a) contacting a sample with a soluble antibody to the SDI-1 protein or fragment thereof; and (b) detecting the presence of the SDI-1 protein, or fragment thereof, bound to the antibody.

* * * * *

SEQUENCE LISTING (1) GENERAL INFORMATION:

(iii) NUMBER OF SEQUENCES: 36

(2) INFORMATION FOR SEQ ID NO:1:

(i) SEQUENCE CHARACTERISTICS:
       (A) LENGTH: 2106 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (vi) ORIGINAL SOURCE:
       (A) ORGANISM: Homo sapiens
       (G) CELL TYPE: SENESCENT HUMAN CELLS (vii) IMMEDIATE SOURCE:
       (A) LIBRARY: SENESCENT CELL DERIVED cDNA LIBRARY
       (B) CLONE: SDI-1

(xi) SEQUENCE DESCRIPTION: SEQ ID NO:1:

```
CCTGCCGAAG TCAGTTCCTT GTGGAGCCGG AGCTGGGCGC GGATTCGCCG AGGCACCGAG      60
GCACTCAGAG GAGGCGCCAT GTCAGAACCG GCTGGGGATG TCCGTCAGAA CCCATGCGGC     120
AGCAAGGCCT GCCGCCGCCT CTTCGGCCCA GTGGACAGCG AGCAGCTGAG CCGCGACTGT     180
GATGCGCTAA TGGCGGGCTG CATCCAGGAG GCCCGTGAGC GATGGAACTT CGACTTTGTC     240
ACCGAGACAC CACTGGAGGG TGACTTCGCC TGGGAGCGTG TGCGGGGCCT TGGCCTGCCC     300
AAGCTCTACC TTCCCACGGG GCCCCGGCGA GGCGGGATG AGTTGGGAGG AGGCAGGCGG      360
CCTGGCACCT CACCTGCTCT GCTGCAGGGG ACAGCAGAGG AAGACCATGT GGACCTGTCA     420
CTGTCTTGTA CCCTTGTGCC TCGCTCAGGG GAGCAGGCTG AAGGGTCCCC AGGTGGACCT     480
GGAGACTCTC AGGGTCGAAA ACGGCGGCAG ACCAGCATGA CAGATTTCTA CCACTCCAAA     540
CGCCGGCTGA TCTTCTCCAA GAGGAAGCCC TAATCCGCCC ACAGGAAGCC TGCAGTCCTG     600
GAAGCGCGAG GGCCTCAAAG GCCCGCTCTA CATCTTCTGC CTTAGTCTCA GTTTGTGTGT     660
CTTAATTATT ATTTGTGTTT TAATTTAAAC ACCTCCTCAT GTACATACCC TGGCCGCCCC     720
CTGCCCCCCA GCCTCTGGCA TTAGAATTAT TTAAACAAAA ACTAGGCGGT TGAATGAGAG     780
GTTCCTAAGA GTGCTGGGCA TTTTTATTTT ATGAAATACT ATTTAAAGCC TCCTCATCCC     840
GTGTTCTCCT TTTCCTCTCT CCCGGAGGTT GGGTGGGCCG GCTTCATGCC AGCTACTTCC     900
TCCTCCCCAC TTGTCCGCTG GGTGGTACCC TCTGGAGGGG TGTGGCTCCT TCCCATCGCT     960
GTCACAGGCG GTTATGAAAT TCACCCCCTT TCCTGGACAC TCAGACCTGA ATTCTTTTTC    1020
ATTTGAGAAG TAAACAGATG GCACTTTGAA GGGGCCTCAC CGAGTGGGGG CATCATCAAA    1080
AACTTTGGAG TCCCCTCACC TCCTCTAAGG TTGGGCAGGG TGACCCTGAA GTGAGCACAG    1140
CCTAGGGCTG AGCTGGGGAC CTGGTACCCT CCTGGCTCTT GATACCCCCC TCTGTCTTGT    1200
GAAGGCAGGG GGAAGGTGGG GTCCTGGAGC AGACCACCCC GCCTGCCCTC ATGGCCCCTC    1260
TGACCTGCAC TGGGGAGCCC GTCTCAGTGT TGAGCCTTTT CCCTCTTTGG CTCCCCTGTA    1320
CCTTTTGAGG AGCCCCAGCT ACCCTTCTTC TCCAGCTGGG CTCTGCAATT CCCCTCTGCT    1380
GCTGTCCCTC CCCCTTGTCC TTTCCCTTCA GTACCCTCTC AGCTCCAGGT GGCTCTGAGG    1440
```

-continued

```
TGCCTGTCCC ACCCCCACCC CCAGCTCAAT GGACTGGAAG GGGAAGGGAC ACACAAGAAG    1500

AAGGGCACCC TAGTTCTACC TCAGGCAGCT CAAGCAGCGA CCGCCCCCTC CTCTAGCTGT    1560

GGGGGTGAGG GTCCCATGTG GTGGCACAGG CCCCCTTGAG TGGGGTTATC TCTGTGTTAG    1620

GGGTATATGA TGGGGGAGTA GATCTTTCTA GGAGGGAGAC ACTGGCCCCT CAAATCGTCC    1680

AGCGACCTTC CTCATCCACC CCATCCCTCC CCAGTTCATT GCACTTTGAT TAGCAGCGGA    1740

ACAAGGAGTC AGACATTTTA AGATGGTGGC AGTAGAGGCT ATGGACAGGG CATGCCACGT    1800

GGGCTCATAT GGGGCTGGGA GTAGTTGTCT TTCCTGGCAC TAACGTTGAG CCCCTGGAGG    1860

CACTGAAGTG CTTAGTGTAC TTGGAGTATT GGGGTCTGAC CCCAAACACC TTCCAGCTCC    1920

TGTAACATAC TGGCCTGGAC TGTTTTCTCT CGGCTCCCCA TGTGTCCTGG TTCCCGTTTC    1980

TCCACCTAGA CTGTAAACCT CTCGAGGGCA GGGACCACAC CCTGTACTGT TCTGTGTCTT    2040

TCACAGCTCC TCCCACAATG CTGATATACA GCAGGTGCTC AATAAACGAT TCTTAGTGAA    2100

AAAAAA                                                               2106
```

(2) INFORMATION FOR SEQ ID NO:2:

(i) SEQUENCE CHARACTERISTICS:
        (A) LENGTH: 164 amino acids
        (B) TYPE: amino acid
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: HOMO SAPIENS
        (B) STRAIN: SDI-1

(vii) IMMEDIATE SOURCE:
        (A) LIBRARY: Senescent cell derived cDNA library (xi) SEQUENCE DESCRIPTION: SEQ ID NO:2:

```
Met Ser Glu Pro Ala Gly Asp Val Arg Gln Asn Pro Cys Gly Ser Lys
1               5                   10                  15

Ala Cys Arg Arg Leu Phe Gly Pro Val Asp Ser Glu Gln Leu Ser Arg
            20                  25                  30

Asp Cys Asp Ala Leu Met Ala Gly Cys Ile Gln Glu Ala Arg Glu Arg
        35                  40                  45

Trp Asn Phe Asp Phe Val Thr Glu Thr Pro Leu Glu Gly Asp Phe Ala
    50                  55                  60

Trp Glu Arg Val Arg Gly Leu Gly Leu Pro Lys Leu Tyr Leu Pro Thr
65                  70                  75                  80

Gly Pro Arg Arg Gly Arg Asp Glu Leu Gly Gly Gly Arg Arg Pro Gly
                85                  90                  95

Thr Ser Pro Ala Leu Leu Gln Gly Thr Ala Glu Glu Asp His Val Asp
            100                 105                 110

Leu Ser Leu Ser Cys Thr Leu Val Pro Arg Ser Gly Glu Gln Ala Glu
        115                 120                 125

Gly Ser Pro Gly Gly Pro Gly Asp Ser Gln Gly Arg Lys Arg Arg Gln
    130                 135                 140

Thr Ser Met Thr Asp Phe Tyr His Ser Lys Arg Arg Leu Ile Phe Ser
145                 150                 155                 160

Lys Arg Lys Pro
```

(2) INFORMATION FOR SEQ ID NO:3:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (vi) ORIGINAL SOURCE:
        (A) ORGANISM: HOMO SAPIENS (xi) SEQUENCE DESCRIPTION: SEQ ID NO:3:

```
AGCCGGTTCT GACATGGCG                                             19
```

(2) INFORMATION FOR SEQ ID NO:4:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (iii) HYPOTHETICAL: NO (v) FRAGMENT TYPE: N-terminal (vii) IMMEDIATE SOURCE:
        (B) CLONE: [His]6 leader peptide (xi) SEQUENCE DESCRIPTION: SEQ ID NO:4:

```
Met Arg Gly Ser His His His His His His Gly Ala
 1               5                  10
```

(2) INFORMATION FOR SEQ ID NO:5:

(i) SEQUENCE CHARACTERISTICS:
        (A) LENGTH: 699 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Schistosoma japonicum (vii) IMMEDIATE SOURCE:
        (B) CLONE: GST (xi) SEQUENCE DESCRIPTION: SEQ ID NO:5:

```
ATGTCCCCTA TACTAGGTTA TTGGAAAATT AAGGGCCTTG TGCAACCCAC TCGACTTCTT     60

TTGGAATATC TTGAAGAAAA ATATGAAGAG CATTTGTATG AGCGCGATGA AGGTGATAAA    120

TGGCGAAACA AAAGTTTGA ATTGGGTTTG GAGTTTCCCA ATCTTCCTTA TTATATTGAT     180

GGTGATGTTA AATTAACACA GTCTATGGCC ATCATACGTT ATATAGCTGA CAAGCACAAC    240

ATGTTGGGTG GTTGTCCAAA AGAGCGTGCA GAGATTTCAA TGCTTGAAGG AGCGGTTTTG    300

GATATTAGAT ACGGTGTTTC GAGAATTGCA TATAGTAAAG ACTTTGAAAC TCTCAAAGTT    360
```

```
GATTTTCTTA GCAAGCTACC TGAAATGCTG AAAATGTTCG AAGATCGTTT ATGTCATAAA    420

ACATATTTAA ATGGTGATCA TGTAACCCAT CCTGACTTCA TGTTGTATGA CGCTCTTGAT    480

GTTGTTTTAT ACATGGACCC AATGTGCCTG GATGCGTTCC CAAAATTAGT TTGTTTTAAA    540

AAACGTATTG AAGCTATCCC ACAAATTGAT AAGTACTTGA AATCCAGCAA GTATATAGCA    600

TGGCCTTTGC AGGGCTGGCA AGCCACGTTT GGTGGTGGCG ACCATCCTCC AAAATCGGAT    660

CTGGTTCCGC GTGGATCCCC GGGAATTCAT CGTGACTGA                          699
```

(2) INFORMATION FOR SEQ ID NO:6:

(i) SEQUENCE CHARACTERISTICS:
        (A) LENGTH: 232 amino acids
        (B) TYPE: amino acid
        (D) TOPOLOGY: linear (ii) MOLECULE TYPE: protein (iii) HYPOTHETICAL: NO (vi) ORIGINAL SOURCE:
        (A) ORGANISM: Schistosoma japonicum (vii) IMMEDIATE SOURCE:
        (B) CLONE: GST (xi) SEQUENCE DESCRIPTION: SEQ ID NO:6:

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95 ly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Leu Val Pro Arg
    210                 215                 220

Gly Ser Pro Gly Ile His Arg Asp
225                 230
```

(2) INFORMATION FOR SEQ ID NO:7:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: linker fragment for GST-SDI-1 gene fusion (xi) SEQUENCE DESCRIPTION: SEQ ID NO:7:

GGATCCCCCC GCC                                                          13

(2) INFORMATION FOR SEQ ID NO:8:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: linker fragment for GST-SDI-1 gene fusion (xi) SEQUENCE DESCRIPTION: SEQ ID NO:8:

CCCTCGAGGG                                                              10

(2) INFORMATION FOR SEQ ID NO:9:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (iii) HYPOTHETICAL: NO (v) FRAGMENT TYPE: internal (vii) IMMEDIATE SOURCE:
        (B) CLONE: hinge region of GST-SDI-1 fusion protein (xi) SEQUENCE DESCRIPTION: SEQ ID NO:9:

Pro Arg Gly Asp Pro Pro Ala
  1               5

(2) INFORMATION FOR SEQ ID NO:10:

(i) SEQUENCE CHARACTERISTICS:
        (A) LENGTH: 1194 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO -continued

```
    (vii) IMMEDIATE SOURCE:
          (B) CLONE: GST-SDI-1 gene fusion (xi) SEQUENCE DESCRIPTION: SEQ ID NO:10:

ATGTCCCCTA TACTAGGTTA TTGGAAAATT AAGGGCCTTG TGCAACCCAC TCGACTTCTT      60

TTGAATATC  TTGAAGAAAA ATATGAAGAG CATTTGTATG AGCGCGATGA AGGTGATAAA     120

TGGCGAAACA AAAAGTTTGA ATTGGGTTTG GAGTTTCCCA ATCTTCCTTA TTATATTGAT     180

GGTGATGTTA AATTAACACA GTCTATGGCC ATCATACGTT ATATAGCTGA CAAGCACAAC     240

ATGTTGGGTG GTTGTCCAAA AGAGCGTGCA GAGATTTCAA TGCTTGAAGG AGCGGTTTTG     300

GATATTAGAT ACGGTGTTTC GAGAATTGCA TATAGTAAAG ACTTTGAAAC TCTCAAAGTT     360

GATTTTCTTA GCAAGCTACC TGAAATGCTG AAAATGTTCG AAGATCGTTT ATGTCATAAA     420

ACATATTTAA ATGGTGATCA TGTAACCCAT CCTGACTTCA TGTTGTATGA CGCTCTTGAT     480

GTTGTTTTAT ACATGGACCC AATGTGCCTG GATGCGTTCC CAAAATTAGT TTGTTTTAAA     540

AAACGTATTG AAGCTATCCC ACAAATTGAT AAGTACTTGA ATCCAGCAA GTATATAGCA     600

TGGCCTTTGC AGGGCTGGCA AGCCACGTTT GGTGGTGGCG ACCATCCTCC AAAATCGGAT     660

CTGGTTCCGC GTGGATCCCC TCGAGGGGAT CCCCCCGCCA TGTCAGAACC GGCTGGGGAT     720

GTCCGTCAGA ACCCATGCGG CAGCAAGGCC TGCCGCCGCC TCTTCGGCCC AGTGGACAGC     780

GAGCAGCTGA GCCGCGACTG TGATGCGCTA ATGGCGGGCT GCATCCAGGA GGCCCGTGAG     840

CGATGGAACT TCGACTTTGT CACCGAGACA CCACTGGAGG GTGACTTCGC CTGGGAGCGT     900

GTGCGGGGCC TTGGCCTGCC CAAGCTCTAC CTTCCCACGG GGCCCCGGCG AGGCCGGGAT     960

GAGTTGGGAG GAGGCAGGCG GCCTGGCACC TCACCTGCTC TGCTGCAGGG GACAGCAGAG    1020

GAAGACCATG TGGACCTGTC ACTGTCTTGT ACCCTTGTGC CTCGCTCAGG GGAGCAGGCT    1080

GAAGGGTCCC CAGGTGGACC TGGAGACTCT CAGGGTCGAA ACGGCGGCA GACCAGCATG    1140

ACAGATTTCT ACCACTCCAA ACGCCGGCTG ATCTTCTCCA AGAGGAAGCC CTAA          1194

(2) INFORMATION FOR SEQ ID NO:11:

(i) SEQUENCE CHARACTERISTICS:
         (A) LENGTH: 397 amino acids
         (B) TYPE: amino acid
         (D) TOPOLOGY: linear (ii) MOLECULE TYPE: protein (iii) HYPOTHETICAL: NO (vii) IMMEDIATE SOURCE:
          (B) CLONE: GST-SDI-1 fusion protein (xi) SEQUENCE DESCRIPTION: SEQ ID NO:11:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
```

-continued

```
                    85                  90                  95
Gly Ala Val Leu Asp Ile Arg Tyr Gly Val Ser Arg Ile Ala Tyr Ser
                   100                 105                 110
Lys Asp Phe Glu Thr Leu Lys Val Asp Phe Leu Ser Lys Leu Pro Glu
               115                 120                 125
Met Leu Lys Met Phe Glu Asp Arg Leu Cys His Lys Thr Tyr Leu Asn
           130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
               165                 170                 175
Val Cys Phe Lys Lys Arg Ile Glu Ala Ile Pro Gln Ile Asp Lys Tyr
           180                 185                 190
Leu Lys Ser Ser Lys Tyr Ile Ala Trp Pro Leu Gln Gly Trp Gln Ala
       195                 200                 205
Thr Phe Gly Gly Gly Asp His Pro Pro Lys Ser Asp Leu Val Pro Arg
   210                 215                 220
Gly Ser Pro Arg Gly Asp Pro Ala Met Ser Glu Pro Ala Gly Asp
225                 230                 235                 240
Val Arg Gln Asn Pro Cys Gly Ser Lys Ala Cys Arg Arg Leu Phe Gly
               245                 250                 255
Pro Val Asp Ser Glu Gln Leu Ser Arg Asp Cys Asp Ala Leu Met Ala
           260                 265                 270
Gly Cys Ile Gln Glu Ala Arg Glu Arg Trp Asn Phe Asp Phe Val Thr
       275                 280                 285
Glu Thr Pro Leu Glu Gly Asp Phe Ala Trp Glu Arg Val Arg Gly Leu
   290                 295                 300
Gly Leu Pro Lys Leu Tyr Leu Pro Thr Gly Pro Arg Arg Gly Arg Asp
305                 310                 315                 320
Glu Leu Gly Gly Gly Arg Arg Pro Gly Thr Ser Pro Ala Leu Leu Gln
               325                 330                 335
Gly Thr Ala Glu Glu Asp His Val Asp Leu Ser Leu Ser Cys Thr Leu
           340                 345                 350
Val Pro Arg Ser Gly Glu Gln Ala Glu Gly Ser Pro Gly Gly Pro Gly
       355                 360                 365
Asp Ser Gln Gly Arg Lys Arg Arg Gln Thr Ser Met Thr Asp Phe Tyr
   370                 375                 380
His Ser Lys Arg Arg Leu Ile Phe Ser Lys Arg Lys Pro
385                 390                 395
```

(2) INFORMATION FOR SEQ ID NO:12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: Primer 12614

(xi) SEQUENCE DESCRIPTION: SEQ ID NO:12:

```
GGAGGATCCA TGTCAGAACC GGCT                                          24
```

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: Primer 12615

(xi) SEQUENCE DESCRIPTION: SEQ ID NO:13:

```
GCAGAATTCC TGTGGGCGGA TTAG                                          24
```

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: Primer (xi) SEQUENCE DESCRIPTION: SEQ ID NO:14:

```
TCTAGGCCTG TACGGAAGTG                                               20
```

(2) INFORMATION FOR SEQ ID NO:15:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: Primer (xi) SEQUENCE DESCRIPTION: SEQ ID NO:15:

```
TAGGAATTCA CTAGTCTAAG CGTAATCTGG AACATCGTAT GGGTAGGGCT TCCTCTTGGA   60
```

(2) INFORMATION FOR SEQ ID NO:16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
                 (B) CLONE: Primer (xi) SEQUENCE DESCRIPTION: SEQ ID NO:16:

TTCGGCCCTC GAGGCCTGAG CCGCGACTGT                                                30

(2) INFORMATION FOR SEQ ID NO:17:

(i) SEQUENCE CHARACTERISTICS:
                 (A) LENGTH: 30 base pairs
                 (B) TYPE: nucleic acid
                 (C) STRANDEDNESS: single
                 (D) TOPOLOGY: linear (ii) MOLECULE TYPE: cDNA (iii) HYPOTHETICAL: NO (iv) ANTI-SENSE: NO (vii) IMMEDIATE SOURCE:
                 (B) CLONE: Primer (xi) SEQUENCE DESCRIPTION: SEQ ID NO:17:

GCTCAGGCCT CGAGGGCCGA AGAAGCGGCG                                                30

(2) INFORMATION FOR SEQ ID NO:18:

(i) SEQUENCE CHARACTERISTICS:
                 (A) LENGTH: 31 base pairs
                 (B) TYPE: nucleic acid
                 (C) STRANDEDNESS: single
                 (D) TOPOLOGY: linear (ii) MOLECULE TYPE: cDNA (iii) HYPOTHETICAL: NO (iv) ANTI-SENSE: NO (vii) IMMEDIATE SOURCE:
                 (B) CLONE: Primer (xi) SEQUENCE DESCRIPTION: SEQ ID NO:18:

TTAGCGCGCC TCGAGGCTGC TCGCTGTCCA C                                              31

(2) INFORMATION FOR SEQ ID NO:19:

(i) SEQUENCE CHARACTERISTICS:
                 (A) LENGTH: 31 base pairs
                 (B) TYPE: nucleic acid
                 (C) STRANDEDNESS: single
                 (D) TOPOLOGY: linear (ii) MOLECULE TYPE: cDNA (iii) HYPOTHETICAL: NO (iv) ANTI-SENSE: NO (vii) IMMEDIATE SOURCE:
                 (B) CLONE: Primer (xi) SEQUENCE DESCRIPTION: SEQ ID NO:19:

CGAGCAGCCT CGAGGCGCGC TAATGGCGGG C                                              31

(2) INFORMATION FOR SEQ ID NO:20:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (vii) IMMEDIATE SOURCE:
            (B) CLONE: Primer (xi) SEQUENCE DESCRIPTION: SEQ ID NO:20:

GGCTGCCCTC GAGGCCGATG GAACTTCGAC                                              30

(2) INFORMATION FOR SEQ ID NO:21:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (vii) IMMEDIATE SOURCE:
            (B) CLONE: Primer (xi) SEQUENCE DESCRIPTION: SEQ ID NO:21:

CCATCGGCCT CGAGGGCAGC CCGCCATTAG                                              30

(2) INFORMATION FOR SEQ ID NO:22:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (vii) IMMEDIATE SOURCE:
            (B) CLONE: Primer (xi) SEQUENCE DESCRIPTION: SEQ ID NO:22:

CGTGAGCGAC CCCGGGGCGT CACCGAGACA CCACTG                                       36

(2) INFORMATION FOR SEQ ID NO:23:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO

```
        (vii) IMMEDIATE SOURCE:
              (B) CLONE: Primer (xi) SEQUENCE DESCRIPTION: SEQ ID NO:23:

CTCGGTGACG CCCCGGGGTC GCTCACGGGC CTCCTG                                      36

(2) INFORMATION FOR SEQ ID NO:24:

(i) SEQUENCE CHARACTERISTICS:
              (A) LENGTH: 30 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (vii) IMMEDIATE SOURCE:
              (B) CLONE: Primer (xi) SEQUENCE DESCRIPTION: SEQ ID NO:24:

TTCGACCCTC GAGGCCTGGA GGGTGACTTC                                             30

(2) INFORMATION FOR SEQ ID NO:25:

(i) SEQUENCE CHARACTERISTICS:
              (A) LENGTH: 30 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (vii) IMMEDIATE SOURCE:
              (B) CLONE: Primer (xi) SEQUENCE DESCRIPTION: SEQ ID NO:25:

CTCCAGGCCT CGAGGGTCGA AGTTCCATCG                                             30

(2) INFORMATION FOR SEQ ID NO:26:

(i) SEQUENCE CHARACTERISTICS:
              (A) LENGTH: 36 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (vii) IMMEDIATE SOURCE:
              (B) CLONE: Primer (xi) SEQUENCE DESCRIPTION: SEQ ID NO:26:

ACCGAGACAT CCCGGGCCGA CTTCGCCTGG GAGCGT                                      36

(2) INFORMATION FOR SEQ ID NO:27:

(i) SEQUENCE CHARACTERISTICS:
              (A) LENGTH: 36 base pairs
              (B) TYPE: nucleic acid
```

```
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: Primer (xi) SEQUENCE DESCRIPTION: SEQ ID NO:27:

GGCGAAGTCG GCCCGGGATG TCTCGGTGAC AAAGTC                    36

(2) INFORMATION FOR SEQ ID NO:28:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: Primer (xi) SEQUENCE DESCRIPTION: SEQ ID NO:28:

CCACTGGAGC CCCGGGGCCG TGTGCGGGGC CTTGGC                    36

(2) INFORMATION FOR SEQ ID NO:29:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: Primer (xi) SEQUENCE DESCRIPTION: SEQ ID NO:29:

CCGCACACGG CCCCGGGGCT CCAGTGGTGT CTCGGT                    36

(2) INFORMATION FOR SEQ ID NO:30:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: Primer (xi) SEQUENCE DESCRIPTION: SEQ ID NO:30:
```

```
GCCTGGCCTC GAGGCGGCCT GCCCAAGCTC                                             30

(2) INFORMATION FOR SEQ ID NO:31:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
         (B) CLONE: Primer (xi) SEQUENCE DESCRIPTION: SEQ ID NO:31:

CAGGCCGCCT CGAGGCCAGG CGAAGTCACC                                             30

(2) INFORMATION FOR SEQ ID NO:32:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
         (B) CLONE: Primer (xi) SEQUENCE DESCRIPTION: SEQ ID NO:32:

CGGGGCCTTC CCCGGGGCCT TCCCACGGGG CCCCGGCGAG G                                41

(2) INFORMATION FOR SEQ ID NO:33:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
         (B) CLONE: Primer (xi) SEQUENCE DESCRIPTION: SEQ ID NO:33:

CGTGGGAAGG CCCCGGGGAA GGCCCCGCAC ACGCTCCCAG                                  40

(2) INFORMATION FOR SEQ ID NO:34:

(i) SEQUENCE CHARACTERISTICS:
        (A) LENGTH: 29 amino acids
        (B) TYPE: amino acid
        (D) TOPOLOGY: linear (ii) MOLECULE TYPE: peptide
```

-continued

```
    (iii) HYPOTHETICAL: NO (v) FRAGMENT TYPE: internal (vii) IMMEDIATE SOURCE:
         (B) CLONE: peptide mimetic fragment (xi) SEQUENCE DESCRIPTION: SEQ ID NO:34:

Trp Asn Phe Asp Phe Xaa Xaa Xaa Xaa Pro Leu Glu Gly Xaa Xaa Xaa
1               5                   10                  15

Trp Xaa Xaa Val Xaa Xaa Xaa Xaa Leu Pro Xaa Xaa Tyr
 20              25

(2) INFORMATION FOR SEQ ID NO:35:

(i) SEQUENCE CHARACTERISTICS:
         (A) LENGTH: 54 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (vii) IMMEDIATE SOURCE:
         (B) CLONE: Primer (xi) SEQUENCE DESCRIPTION: SEQ ID NO:35:

CAGAATCACA AGCCACTCGA GGGTAAGTAC GAGTGGGAGC GTGTGCGGGG CCTT            54

(2) INFORMATION FOR SEQ ID NO:36:

(i) SEQUENCE CHARACTERISTICS:
         (A) LENGTH: 48 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (vii) IMMEDIATE SOURCE:
         (B) CLONE: Primer (xi) SEQUENCE DESCRIPTION: SEQ ID NO:36:

CTTACCCTCG AGTGGCTTGT GATTCTGAAA GTCGAAGTTC CATCGCTC                  48
```